(12) United States Patent
Sharp et al.

(10) Patent No.: US 8,734,402 B2
(45) Date of Patent: May 27, 2014

(54) INJECTION DEVICE

(75) Inventors: Robert Sharp, The Oxford Science Park (GB); Kevin Stamp, Sheffield (GB); Eliot Clare, The Oxford Science Park (GB); Rupert Hosking, The Oxford Science Park (GB)

(73) Assignee: Future Injection Technologies Limited (GB)

( * ) Notice: Subject to any disclaimer, the term of this patent is extended or adjusted under 35 U.S.C. 154(b) by 745 days.

(21) Appl. No.: 12/690,644

(22) Filed: Jan. 20, 2010

(65) Prior Publication Data

US 2010/0185178 A1 Jul. 22, 2010

Related U.S. Application Data

(60) Provisional application No. 61/145,908, filed on Jan. 20, 2009.

(30) Foreign Application Priority Data

Jan. 20, 2009 (GB) .................................. 0900930.9

(51) Int. Cl.
*A61M 5/32* (2006.01)

(52) U.S. Cl.
USPC .......................................... 604/198; 604/223

(58) Field of Classification Search
USPC ........................ 604/110, 192, 197, 198, 223
See application file for complete search history.

(56) References Cited

U.S. PATENT DOCUMENTS

| | | |
|---|---|---|
| 3,182,660 A | 5/1965 | Weydanz |
| 4,312,343 A | 1/1982 | LeVeen et al. |
| 4,565,543 A | 1/1986 | Bekkering et al. ............ 604/135 |
| 4,617,016 A | 10/1986 | Blomberg |
| 4,689,042 A | 8/1987 | Sarnoff et al. ................... 604/89 |
| 4,717,383 A | 1/1988 | Phillips et al. |

(Continued)

FOREIGN PATENT DOCUMENTS

| | | |
|---|---|---|
| DE | 19532410 | 3/1997 |
| DE | 20013579 | 3/2001 |

(Continued)

OTHER PUBLICATIONS

Examination Report issued on May 4, 2011 for UK Pat. App. No. GB1000938.9, filed Jan. 20, 2010 (Inventor—Sharp; Applicant—Future Injection Technologies Ltd.).

(Continued)

*Primary Examiner* — Kevin C Sirmons
*Assistant Examiner* — Deanna K Hall
(74) *Attorney, Agent, or Firm* — Ballard Spahr LLP

(57) ABSTRACT

An injection device including a syringe having a needle, a barrel and a plunger. The device is configured to provide an automatic injection cycle and includes a drive coupling arrangement between a driving spring and the syringe. In operation, a drive force can be selectively transmitted between the respective first and second parts of the drive coupling arrangement depending upon their relative rotational positions such that, when the first and second parts are in a first relative rotational position during the dispensing stage, a driving force is transmitted to the plunger to drive the plunger into the barrel, and, when the first and second parts are in a second relative rotational position during the retraction stage, no force is transmitted to the plunger to allow the plunger and the syringe to retract.

36 Claims, 21 Drawing Sheets

(56) References Cited

U.S. PATENT DOCUMENTS

| | | | |
|---|---|---|---|
| 4,822,340 A | 4/1989 | Kamstra | 604/135 |
| 4,902,279 A | 2/1990 | Schmidtz et al. | 604/134 |
| 4,968,302 A | 11/1990 | Schluter et al. | 604/135 |
| 4,983,164 A | 1/1991 | Hook et al. | 604/87 |
| 5,084,017 A | 1/1992 | Maffetone | 604/110 |
| 5,092,842 A | 3/1992 | Bechtold et al. | 604/135 |
| 5,092,843 A | 3/1992 | Monroe et al. | 604/138 |
| 5,114,404 A | 5/1992 | Paxton et al. | |
| 5,114,406 A | 5/1992 | Gabriel et al. | 604/136 |
| 5,120,310 A | 6/1992 | Shaw | 604/110 |
| 5,137,516 A | 8/1992 | Rand et al. | 604/136 |
| 5,147,327 A | 9/1992 | Johnson | |
| 5,167,632 A | 12/1992 | Eid et al. | 604/136 |
| 5,167,641 A | 12/1992 | Schmitz | 604/196 |
| 5,201,710 A | 4/1993 | Caselli | 604/110 |
| 5,267,963 A | 12/1993 | Bachynsky | 604/134 |
| 5,273,544 A | 12/1993 | van der Wal | 604/134 |
| 5,295,965 A | 3/1994 | Wilmot | 604/136 |
| 5,300,029 A | 4/1994 | Denance | |
| 5,300,030 A | 4/1994 | Crossman et al. | 604/136 |
| 5,320,609 A | 6/1994 | Haber et al. | 604/135 |
| 5,385,551 A | 1/1995 | Shaw | 604/110 |
| 5,407,436 A | 4/1995 | Toft et al. | 604/195 |
| 5,425,715 A | 6/1995 | Dalling et al. | 604/136 |
| 5,478,316 A | 12/1995 | Bitdinger et al. | 604/135 |
| 5,480,381 A | 1/1996 | Weston | |
| 5,487,732 A | 1/1996 | Jeffrey | 604/110 |
| 5,514,097 A | 5/1996 | Knauer | 604/136 |
| 5,620,421 A | 4/1997 | Schmitz | 604/135 |
| 5,626,566 A | 5/1997 | Petersen et al. | |
| 5,643,214 A | 7/1997 | Marshall et al. | 604/134 |
| 5,658,259 A | 8/1997 | Pearson et al. | 604/232 |
| 5,681,291 A | 10/1997 | Galli | 604/192 |
| 5,681,292 A | 10/1997 | Tober et al. | 604/195 |
| 5,709,662 A | 1/1998 | Olive et al. | 604/135 |
| 5,769,822 A | 6/1998 | McGary et al. | 604/110 |
| 5,779,677 A | 7/1998 | Frezza | 604/134 |
| 5,843,036 A | 12/1998 | Olive et al. | 604/136 |
| 5,971,953 A | 10/1999 | Bachynsky | 604/90 |
| 6,015,396 A | 1/2000 | Buttgen et al. | 604/192 |
| 6,077,247 A | 6/2000 | Marshall et al. | 604/156 |
| 6,099,503 A | 8/2000 | Stradella | 604/135 |
| 6,159,181 A | 12/2000 | Crossman et al. | 604/157 |
| 6,203,530 B1 | 3/2001 | Stewart, Sr. | 604/207 |
| 6,210,369 B1 | 4/2001 | Wilmot et al. | 604/157 |
| 6,221,044 B1 | 4/2001 | Greco | 604/134 |
| 6,270,479 B1 | 8/2001 | Bergens et al. | 604/156 |
| 6,280,421 B1 | 8/2001 | Kirchhofer et al. | 604/218 |
| 6,454,743 B1 | 9/2002 | Weber | 604/131 |
| 6,544,234 B1 | 4/2003 | Gabriel | 604/207 |
| 6,575,939 B1 | 6/2003 | Brunel | 604/187 |
| 6,585,698 B1 | 7/2003 | Packman et al. | 604/207 |
| 6,589,210 B1 | 7/2003 | Rolfe | 604/157 |
| 6,599,272 B1 | 7/2003 | Hjertman et al. | 604/209 |
| 6,656,163 B1 | 12/2003 | Marshall et al. | 604/198 |
| 6,692,469 B1 | 2/2004 | Weekes et al. | 604/197 |
| 6,743,203 B1 | 6/2004 | Pickhard | 604/139 |
| 6,767,336 B1 | 7/2004 | Kaplan | 604/136 |
| 6,890,319 B1 | 5/2005 | Crocker | 604/131 |
| 6,932,793 B1 | 8/2005 | Marshall et al. | 604/135 |
| 7,635,356 B2 | 12/2009 | Stamp | |
| 7,645,265 B2 | 1/2010 | Stamp | |
| 8,187,226 B2 | 5/2012 | Stamp et al. | |
| 8,308,697 B2 | 11/2012 | Stamp et al. | |
| 2001/0005781 A1 | 6/2001 | Bergens et al. | 604/208 |
| 2001/0044847 A1 | 11/2001 | Kirchhofer et al. | 709/227 |
| 2001/0049496 A1 | 12/2001 | Kirchhofer et al. | 604/154 |
| 2002/0004279 A1 | 1/2002 | Ljunggreen et al. | 604/218 |
| 2002/0010456 A1 | 1/2002 | Sadowski et al. | 604/511 |
| 2002/0016563 A1 | 2/2002 | Hill et al. | 604/85 |
| 2002/0042592 A1 | 4/2002 | Wilmot et al. | 604/92 |
| 2002/0120235 A1 | 8/2002 | Enggaard | 604/135 |
| 2002/0161339 A1 | 10/2002 | Rolfe | 604/209 |
| 2002/0165500 A1 | 11/2002 | Bechtold et al. | 604/209 |
| 2002/0183690 A1 | 12/2002 | Arnisolle | 604/83 |
| 2003/0023205 A1 | 1/2003 | Botich et al. | 604/110 |
| 2003/0028151 A1 | 2/2003 | Righi et al. | 604/218 |
| 2003/0050601 A1 | 3/2003 | Righi et al. | 604/110 |
| 2003/0093036 A1 | 5/2003 | Crossman et al. | 604/197 |
| 2003/0199833 A1 | 10/2003 | Barker et al. | 604/197 |
| 2004/0019326 A1 | 1/2004 | Gilbert et al. | 604/135 |
| 2004/0024367 A1 | 2/2004 | Gilbert | 604/198 |
| 2004/0039336 A1 | 2/2004 | Amark et al. | 604/136 |
| 2004/0054327 A1 | 3/2004 | Gillespie, III | 604/135 |
| 2004/0064106 A1 | 4/2004 | Pressly et al. | 604/231 |
| 2004/0111063 A1 | 6/2004 | Botich et al. | 604/195 |
| 2004/0133159 A1 | 7/2004 | Haider et al. | 604/110 |
| 2004/0215151 A1 | 10/2004 | Marshall et al. | 604/198 |
| 2004/0215152 A1 | 10/2004 | Kirchhofer et al. | 604/211 |
| 2004/0225262 A1 | 11/2004 | Fathallah et al. | 604/198 |
| 2005/0165360 A1 | 7/2005 | Stamp | 604/187 |
| 2005/0171477 A1 | 8/2005 | Rubin et al. | 604/156 |
| 2005/0203466 A1 | 9/2005 | Hommann et al. | 604/240 |
| 2005/0261634 A1 | 11/2005 | Karlsson | 604/197 |
| 2005/0277885 A1 | 12/2005 | Scherer | 604/136 |
| 2005/0288633 A1 | 12/2005 | Jeffrey | 604/110 |
| 2006/0030819 A1 | 2/2006 | Young et al. | 604/187 |
| 2006/0069348 A1 | 3/2006 | Parker et al. | 604/110 |
| 2006/0111666 A1 | 5/2006 | Hommann et al. | |
| 2006/0167410 A1 | 7/2006 | Zeoli et al. | 604/110 |
| 2006/0167412 A1 | 7/2006 | Marshall | 604/110 |
| 2006/0178630 A1 | 8/2006 | Bostrom et al. | 604/135 |
| 2006/0178641 A1 | 8/2006 | Reynolds | |
| 2006/0184117 A1 | 8/2006 | Knight et al. | 604/135 |
| 2006/0224117 A1 | 10/2006 | Hommann et al. | 604/136 |
| 2006/0253074 A1 | 11/2006 | Thayer | 604/110 |
| 2006/0276753 A1 | 12/2006 | Kronestedt et al. | 604/186 |
| 2007/0005021 A1 | 1/2007 | Kohlbrenner et al. | 604/208 |
| 2007/0021720 A1 | 1/2007 | Guillermo | 604/187 |
| 2007/0027430 A1 | 2/2007 | Hommann | 604/207 |
| 2007/0088290 A1 | 4/2007 | Heiniger et al. | 604/218 |
| 2008/0009807 A1 | 1/2008 | Hommann | 604/207 |
| 2008/0077084 A1 | 3/2008 | Hommann | 604/93.01 |
| 2008/0188798 A1 | 8/2008 | Weber | 604/82 |
| 2008/0195057 A1 | 8/2008 | Graf et al. | 604/218 |
| 2008/0312591 A1 | 12/2008 | Harrison | 604/135 |
| 2008/0312592 A1 | 12/2008 | Barrow-Williams et al. | 604/136 |
| 2009/0012470 A1 | 1/2009 | Barrow-Williams | 604/136 |
| 2009/0012471 A1 | 1/2009 | Harrison | 604/136 |
| 2009/0030442 A1 | 1/2009 | Potter et al. | 606/182 |
| 2009/0157039 A1 | 6/2009 | Lenzner et al. | 604/500 |
| 2009/0192486 A1 | 7/2009 | Wilmot et al. | 604/506 |
| 2009/0227955 A1 | 9/2009 | Hirschel et al. | 604/187 |
| 2010/0049125 A1* | 2/2010 | James et al. | 604/110 |
| 2010/0312195 A1 | 12/2010 | Johansen et al. | |

FOREIGN PATENT DOCUMENTS

| | | |
|---|---|---|
| DE | 202004016789 | 12/2004 |
| DE | 202004016790 | 12/2004 |
| DE | 202004016791 | 12/2004 |
| EP | 0302278 A1 | 2/1989 |
| EP | 0709106 | 1/1996 |
| EP | 1743666 A1 | 1/2007 |
| EP | 1927372 | 6/2008 |
| ES | 2070782 A1 | 6/1995 |
| ES | 2107382 A1 | 11/1997 |
| FR | 2741810 | 6/1997 |
| GB | 2414403 A | 11/2005 |
| GB | 2410188 | 1/2006 |
| GB | 2438591 | 12/2007 |
| GB | 2447339 | 9/2008 |
| GB | 2451662 | 2/2009 |
| GB | 1000938.9 | 1/2010 |
| GB | 2467420 | 4/2010 |
| WO | WO93/20867 | 10/1993 |
| WO | WO-96/07443 A1 | 3/1996 |
| WO | WO9922789 | 5/1999 |
| WO | WO01/19428 | 3/2001 |
| WO | WO0141838 | 6/2001 |
| WO | WO 01/72361 | 10/2001 |
| WO | 02/17996 A1 | 3/2002 |
| WO | 2004/011065 A1 | 2/2004 |
| WO | WO2004054645 | 7/2004 |

(56) References Cited

FOREIGN PATENT DOCUMENTS

| WO | WO2004108194 | 12/2004 |
|----|---|---|
| WO | WO2005025636 | 3/2005 |
| WO | WO2005113039 | 12/2005 |
| WO | WO2005115506 | 12/2005 |
| WO | WO2005115509 | 12/2005 |
| WO | WO2005115516 | 12/2005 |
| WO | WO 2006/057604 | 6/2006 |
| WO | WO2006106291 | 10/2006 |
| WO | WO2007/020239 | 2/2007 |
| WO | WO2007020090 | 2/2007 |
| WO | WO2007083115 | 7/2007 |
| WO | WO2008029280 | 3/2008 |
| WO | WO 2008/059385 | 5/2008 |
| WO | WO2008112472 | 9/2008 |
| WO | WO2009006985 | 1/2009 |
| WO | WO2009/153132 | 12/2009 |
| WO | PCT/GB2010/000078 | 1/2010 |
| WO | WO2010/033778 | 3/2010 |

OTHER PUBLICATIONS

First Office Action Issued by State Intellectual Property Office of China on Dec. 31, 2012 (Application No. 201080013003.9; Applicant—Future Injection Technologies Limited; Title—Injection Device.).

International Search Report and Written Opinion for International Application No. PCT/GB2011/001082 (mailed Dec. 2, 2011).

International Search Report for International Application No. GB1112465.8 (mailed Oct. 25, 2011).

* cited by examiner

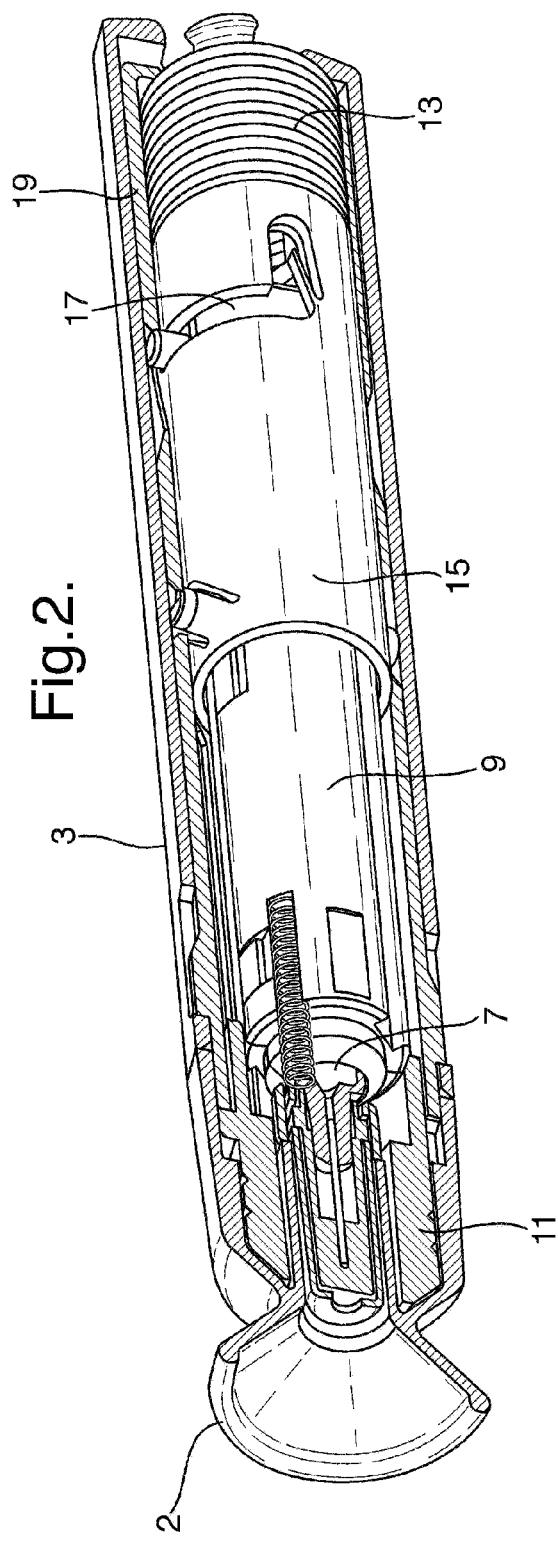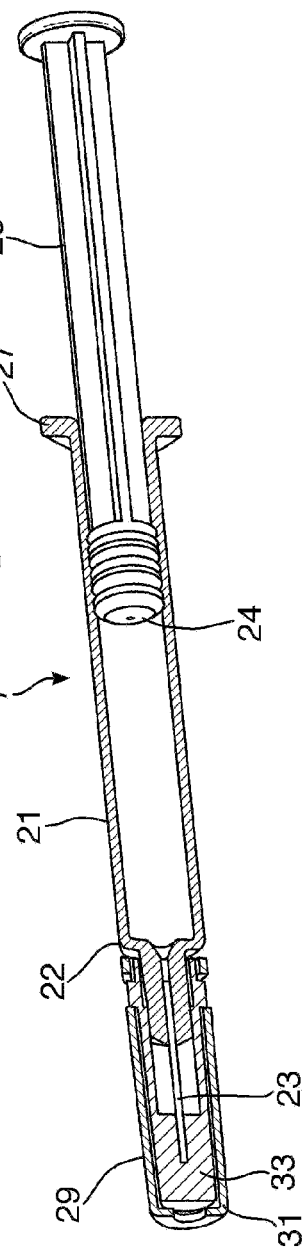

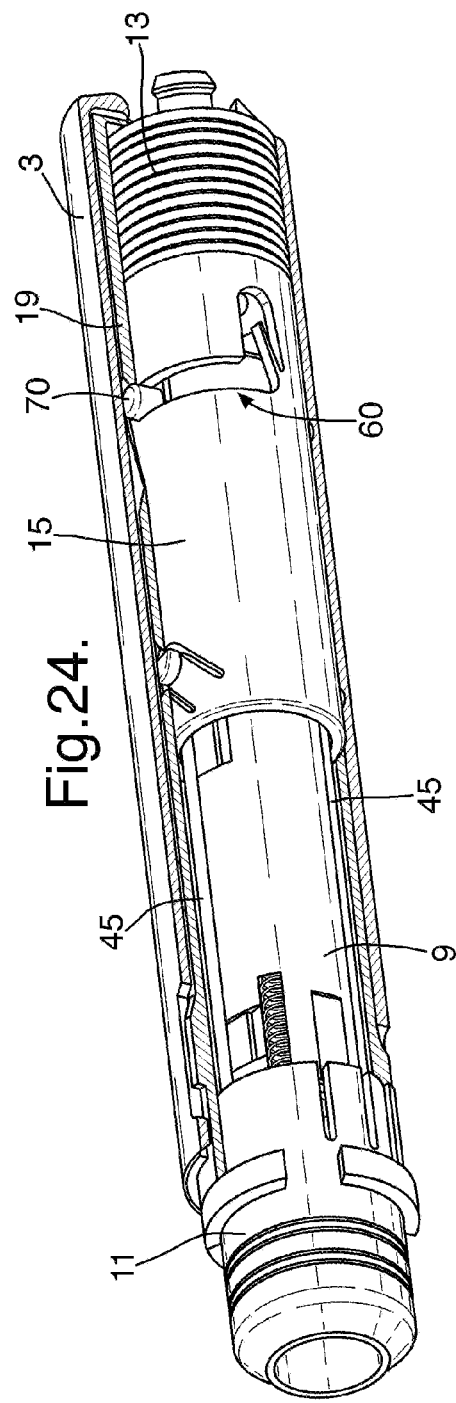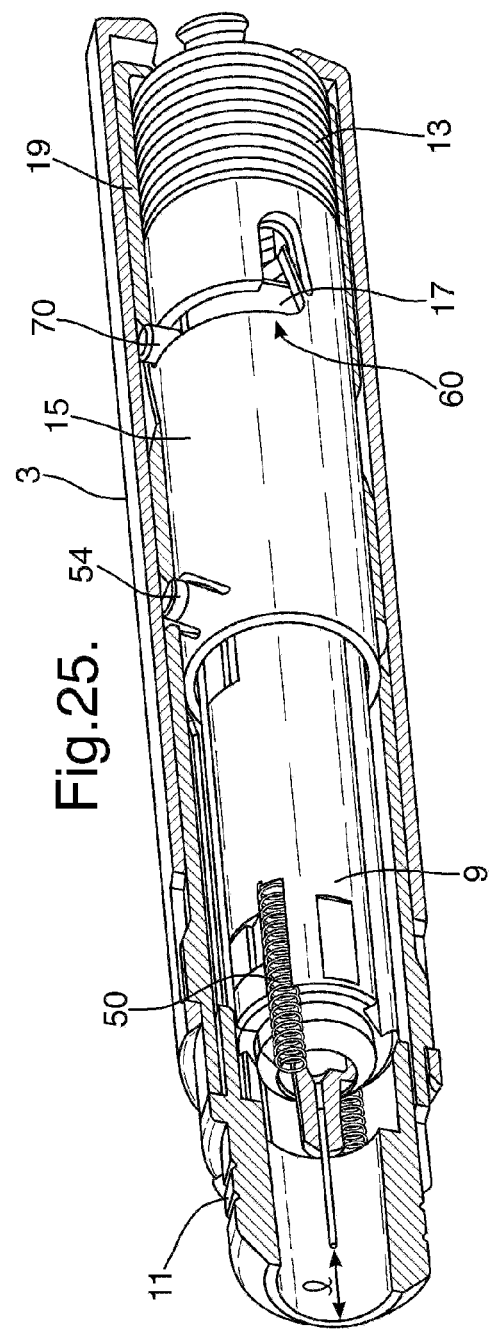

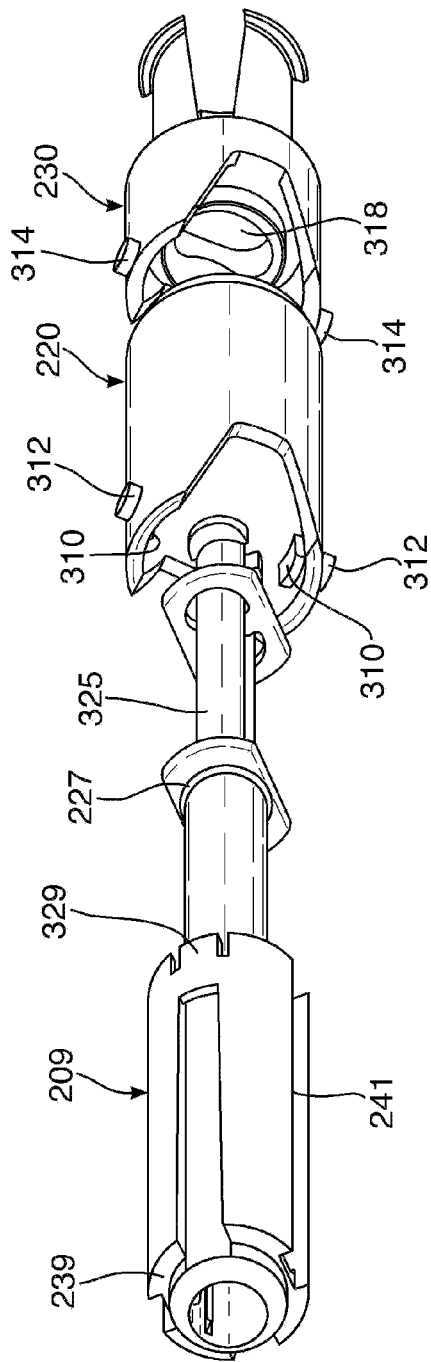
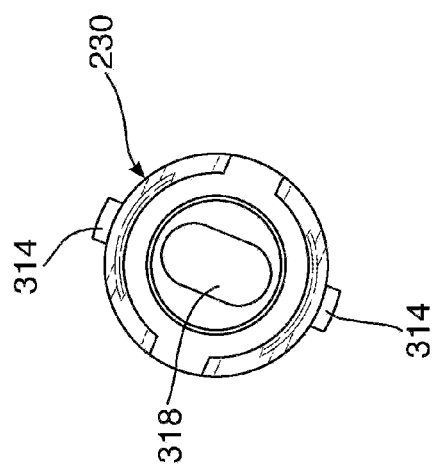
Fig.31.
Fig.31A.

INJECTION DEVICE

CROSS-REFERENCE TO RELATED APPLICATIONS

This application claims priority to U.S. Provisional Patent Application Ser. No. 61/145,908, filed Jan. 20, 2009, and UK Patent Application No. GB 0900930.9, filed Jan. 20, 2009, both of which are hereby incorporated by reference in their entireties.

BACKGROUND OF THE INVENTION

1. Technical Field

The present invention relates to injection devices for the dispensing of liquids, and more particularly to automatic injection devices (so called "auto-injectors").

2. Technical Background

Automatic injection devices are typically configured such that when activated by a user, e.g. by pressing a button etc., an injection is automatically delivered. In order to automatically deliver an injection, such devices may be configured to automatically advance the needle of a syringe for insertion into the body of a user, depress the plunger to dispense liquid from the syringe barrel, and retract the needle. It will be appreciated that automatic injection devices in accordance with the present invention may be used in conjunction with veterinary applications, as well as applications to the human body, and thus references herein to the "body", or such like, may refer to the human or animal body.

Certain issues need to be considered when designing an automatic injection device. Syringes are subject to strict regulations. In order to gain acceptance, an injection device should be compatible with existing syringes which have already been granted regulatory approval. This avoids the need to seek further regulatory approval which would otherwise be required if any modification of the syringe were required to cooperate with the remainder of the device. The injection device must also comply with ever increasing regulations aimed at reducing risk of needle stick injuries.

Further considerations are involved in avoiding breakage or damage to the syringe incorporated in the device during actuation. It is often necessary to drive the plunger of the syringe forward with considerable force to ensure that an intended dose is dispensed, and to force it through the tissues of the body to the desired delivery depth, particularly when the liquid to be dispensed is relatively viscous, or if it is to be injected to a greater depth. Forces exerted on the plunger may be transmitted to the syringe body via the relatively incompressible liquid disposed in the syringe, and may result in breakage or damage to the syringe, particularly to the syringe barrel, which is often formed of glass.

One automatic injection device is disclosed in GB 2410188. The Applicant has realised that this arrangement suffers from certain disadvantages. For example, this arrangement relies upon the radial tags of an inner housing engaging with the plunger and barrel, or plunger only, or, to transmit a driving force to the plunger and barrel, or plunger at the appropriate times during the actuation cycle. This causes axial movement of the plunger and barrel, or plunger relative to the outer housing during the needle advancing and dispensing stages respectively. These radial tags also engage the inner wall of the outer housing. As the inner housing moves axially within the outer housing, the tags scrape along the inner wall of the outer housing, creating friction opposing the axial movement of the plunger and/or barrel. This may in turn mean that a greater force must be exerted to drive the inner housing forward and overcome the frictional forces generated, especially when the liquid to be dispensed is a more viscous liquid. Further frictional forces may arise in these arrangements in the axial direction as the radial tags slide out of contact with the plunger and barrel.

Another problem which the Applicant has identified may arise with the arrangement of GB 2410188 relates to the way in which the radial tags of the inner housing engage the rear flange of the syringe barrel to drive it forward. This rear flange is often referred to as the "finger flange" because, when a manual injection is delivered using a syringe, the user's fingers rest in front of the flange to provide the necessary resistance to allow depression of the plunger using the thumb. The rear flange is a particularly delicate part of the syringe, which is often subject to manufacturing flaws, and is therefore susceptible to breakage. By driving the barrel forward by direct contact between the radial tags and the rear flange, a significant risk of breakage may arise as a result of the large forces which may be required to drive the barrel forward into the skin, and overcome the frictional resistance to the movement of the radial tags, especially for deeper injections.

In practice, this problem is compounded, as the forward radial tags may not abut the rear flange prior to activation of the device. Some clearance between the finger flange and the tags prior to activation may be present to introduce tolerance with respect to the axial position of the syringe relative to the inner and outer housing, and ensure that the flange will abut the radial tags once the inner housing moves forward. Variation in the axial position of the syringe with respect to the inner and outer housing in devices of the type shown in GB2410188 may be introduced during manufacture, or for example, if the device is dropped or held in certain orientations, or due to variations in atmospheric pressure or the way in which the device is filled with liquid prior to use. Variation may also arise if the device is used in conjunction with different sizes of syringe. It is then necessary to design the device to accommodate the largest size of syringe which may be used, such that a significant gap may exist between the radial tags and flanges of a syringe unless it is at the upper end of the possible size range. Such variation in the axial position of the syringe relative to the housing may cause variation of the dose delivered, or in extreme cases, the radial tags may even come to rest forward of the finger flange resulting in failure of the device to operate. Clearance between the finger flange and the tags may therefore be introduced in an attempt to accommodate any such variation. For example, GB 2447339 discloses modifications of the arrangements in GB2410188 including means to bias the barrel forward of the tags which act on the finger flange to try to ensure that the tags will engage the finger flange once driven forward. The Applicant has realised that when the radial tags must be driven forward through the air in a gap between the tags and the flange to engage the finger flange in this way, a greater driving force must be used to be sufficient to overcome the inertia of the finger flange and cause it to start moving with the inner housing. The stationary syringe finger flange will experience significant forces upon impact with the radial tags, which will already be moving forward axially at speed, increasing further the risk of damage to the flange and/or syringe barrel.

SUMMARY OF THE INVENTION

The present invention is directed to an improved injection device.

In accordance with one aspect of the present invention there is provided an automatic injection device comprising a syringe, the syringe comprising a needle, a plunger, and a barrel having a rear flange; wherein the barrel and the rear flange are immobilised in a syringe housing such that they can be moved within the device by a force applied to the syringe housing.

The invention in accordance with this aspect may incorporate any or all of the features described in respect of the other aspects and embodiments of the invention.

By locating the barrel and rear flange of the syringe in a housing in this way, such that the barrel and rear flange are immobilised by the housing, driving forces transmitted to the barrel and flange in use can be more evenly distributed. In particular the force on the plunger necessary to drive it into the barrel does not need to be borne solely by the flange. Indeed the syringe housing allows force exerted on the plunger to be transmitted to and carried by the barrel, bypassing the flange. Since in use the housing immobilizes the barrel, the syringe housing and barrel are therefore coupled to one another, and move together as one. The syringe does not move relative to the housing.

Preferably the syringe housing clamps on to the syringe barrel.

In accordance with a further aspect of the invention there is provided an automatic injection device comprising a syringe, the syringe comprising a needle, a plunger, and a barrel having a rear flange; wherein the barrel and the rear flange are immobilised in a syringe housing such that they can be moved within the device by a force applied to the syringe housing, wherein the syringe housing clamps on to the syringe barrel.

The invention in accordance with this aspect may incorporate any or all of the features described in respect of the other aspects and embodiments of the invention.

As described above, in conventional arrangements, when the plunger of a syringe is driven axially forward to dispense liquid from the barrel in use, considerable forces may be transmitted to the syringe barrel itself via the relatively incompressible liquid disposed in the barrel. These problems are compounded when the liquid is relatively viscous and/or if the liquid is to be injected into a person at a greater depth. In these situations, greater forces are required to expel the liquid from the barrel during dispensing, and force it through the skin into the body. There is consequently a risk that that the syringe may be damaged or even break, such that the intended dose of liquid may not be dispensed, at least fully, and that the user may be subjected to undesirable trauma, for example if they are unsure whether the device has operated, or if the needle fails to retract. Embodiments of the present invention address these problems.

The syringe housing of the present invention in any of its aspects and embodiments advantageously extends over the rear flange to protect the flange. As mentioned above, the rear flange of the barrel is one of the most delicate parts of a syringe, and may be more commonly subject to flaws during manufacture than other parts of the syringe. This part of the syringe is also subjected to some of the greatest forces in use as the plunger is driven into the barrel. The syringe housing of the present invention reduces the level of forces experienced by this more delicate part of the syringe, and ensure that no forces are exerted directly on it in use. The housing may be configured effectively to isolate the rear flange from axial forces applied to the plunger in use.

By reducing the level of forces transmitted to the syringe barrel, in particular its rear flange in this way, the syringe housing of the present invention makes it possible to exert greater forces on the plunger in use without modifying or strengthening the syringe itself. This may allow more viscous liquids to be dispensed and/or liquids to be dispensed to a greater depth in the body. As the housing is clamped on to the syringe body, the syringe housing may also result in the barrel being placed in compression rather than tension use. This may further reduce the likelihood of breakage or damage to the barrel, which is commonly made of glass, as glass is stronger under compression than tension.

It will be appreciated that the syringe housing provides a path whereby axial forces may be transmitted to the syringe barrel in a manner which bypasses the flange. This is counter intuitive, in that it was previously believed that driving the plunger into the barrel of an automatic injection device must involve pushing against the rear flange in the same manner as when actuating a conventional manually operated device. In preferred embodiments the housing is configured such that no axial forces are applied to the rear flange when the plunger is driven into the barrel in use. Preferably the housing is configured such that when the plunger is driven into the barrel in use, no axial force is transmitted to the barrel of the syringe through the rear flange.

This concept is novel and inventive in its own right and so in accordance with a further aspect of the invention, there is provided an automatic injection device comprising a syringe, the syringe comprising a needle, a plunger, and a barrel having a rear flange; wherein the syringe is received in a housing configured such that when the plunger is driven into the barrel in use, no axial force is transmitted to the barrel of the syringe through the rear flange.

The invention in accordance with this further aspect may incorporate any or all of the features described in respect of the other aspects and embodiments of the invention. Preferably therefore the barrel and the rear flange are immobilised in the syringe housing such that they can be moved within the device by a force applied to the housing, and preferably the syringe housing clamps on to the syringe barrel.

In accordance with the invention in any of its aspects and embodiments, the housing may be any suitable arrangement which may immobilise the body of the syringe, such that the body will move as a unit with the housing, and in preferred embodiments clamps around the syringe barrel. For example, the housing may be in the form of a frame. However, in preferred embodiments the barrel including the rear flange is encased by the housing. In these embodiments, the housing circumferentially surrounds the barrel including its rear flange, and provides a protective shell for the syringe barrel and flange.

In preferred embodiments the syringe housing extends over the entire length of the barrel. This may further enhance the ability of the housing to distribute forces applied to the syringe body. In some sets of embodiments the front end of the housing engages over the front shoulder or cone of the syringe and the rear end of the housing extends behind the rear flange of the barrel. The needle of the syringe extends beyond the front end of the syringe housing.

It will be appreciated that the rear flange of the barrel may act as a stop to prevent axial movement of the housing relative to the barrel in the forward direction. By extending over the rear flange, the housing may provide a route allowing axial forces applied e.g. via the plunger, to be transmitted to the barrel body via the housing such that they bypass the rear flange. In some sets of embodiments of the invention, the syringe housing extends over the end of the rear flange, between the rear flange and the free end of the plunger. The rear end of the housing may be configured to hook over i.e. behind the rear flange. The housing may comprise a rear flange for this purpose.

In some embodiments the interior of the syringe housing comprises means for locating the rear flange of the barrel. For example, such means may comprise a groove or any other suitable formation.

In some preferred embodiments the syringe housing does not directly contact the rear, i.e. plunger-facing, surface of the rear flange. This may improve isolation of the flange from forces applied to the plunger. In some sets of embodiments the rear end of the syringe housing extends behind the rear surface of the rear flange, and is axially spaced therefrom. For example, an air gap may be located between the flange and the end of the housing.

The part of the plunger which is not disposed in the barrel extends beyond the rear end of the syringe housing. The syringe housing should be configured such that it does not interfere with operation of the plunger in use. In embodiments, the syringe housing only extends axially beyond the rear end of the barrel a sufficient distance to secure the housing over the rear flange.

The syringe housing may be formed of any suitable material or materials. The syringe housing should be a rigid to allow forces to be distributed within the body of the housing. In preferred embodiments the syringe housing is a plastic housing. For example, the housing may be formed of a polymeric material, e.g. polyethylene. The housing may be injection moulded.

In some sets of embodiments the interior of the syringe housing comprises means for gripping the barrel of the syringe. In these embodiments, the syringe housing may define a rigid outer shell, and inner gripping means. The gripping means preferably directly contacts the syringe barrel. In embodiments the gripping means may comprise compressible material, e.g. positioned between the outer shell of the syringe housing and the barrel. The compressible material may be a resiliently compressible material, such as synthetic rubber. This may further reduce the risk of damage to the syringe body, damping the effect of any forces present in the syringe housing, and avoiding damage to the syringe barrel during and after assembly as a result of contact between the rigid syringe housing and the barrel.

Any arrangement may be used which results in some gripping of the syringe barrel and/or flange in use. Any combination of the arrangements described below may be used. The gripping means may extend axially and/or circumferentially between the syringe housing and the barrel. In embodiments, the gripping means is configured to clamp around the barrel. The gripping means may provide a continuous lining for the outer shell of the syringe housing, or may be provided in one or more discrete regions. The gripping means may comprise one or more compressible members, which may be in the form of rings, or elongate members.

In some sets of embodiments the gripping means comprises at least one ring of compressible material extending around the syringe barrel between the outer shell of the syringe housing and the barrel. It will be appreciated that more than one such ring may be provided, and rings may be provided at intervals along the length of the barrel. The rings may fully or partially surround the barrel, and may, for example, be O-rings. In some embodiments of the invention, the syringe housing comprises a ring of compressible material in the region of each axial end for this purpose.

In some sets of embodiments the interior surface of the outer shell of the syringe housing comprises locating means for the gripping means. For example, in some embodiments the inner surface comprises one or more grooves for this purpose. In an exemplary embodiment the inner surface comprises a ring shaped groove in the region of each axial end for locating the gripping means.

In some embodiments, gripping means is provided between at least one axial end of the barrel and the syringe housing. In preferred embodiments gripping means is provided between the front surface of the rear flange of the barrel and the syringe housing. In these embodiments the gripping means is preferably in the form of a ring, e.g. an O-ring. This may dampen the effect of any forces exerted on the rear end of the syringe housing, reducing the level of forces which may be indirectly transmitted from the housing to the rear flange.

In accordance with any of the aspects or embodiments of the invention, the syringe housing may comprise a viewing window to enable viewing of the plunger within the syringe barrel. The viewing window may enable the user to view the position of the plunger before and after actuation of the device. This may enable a user to check that a dose of liquid has been fully dispensed by looking at the position of the plunger in the barrel, and/or the amount of liquid visible in the barrel. The viewing window preferably extends axially along the syringe housing a distance sufficient to enable viewing of the plunger in its most fully retracted position expected prior to dispensing of a dose of liquid, and its most fully extended position expected after dispensing of the dose of liquid. The viewing window preferably extends axially over the full intended distance of travel of at least the front end of the plunger.

In some embodiments a rear end of the syringe housing cooperates with the plunger to constrain the plunger against rotation relative to the syringe barrel as it is driven into the syringe barrel in use. Thus the syringe housing may be configured to cooperate with the syringe plunger to maintain a rotational alignment of the plunger relative to the barrel as the plunger is driven into the barrel in use. This may help resist twisting of the plunger as it is driven into the barrel in use, which may be particularly advantageous when the syringe is used in conjunction with certain drive mechanisms as described below. In some embodiments the plunger comprises axially extending guide means which cooperates with the syringe housing to guide movement of the plunger into the barrel. For example this may be achieved using a pin in slot arrangement or similar. The axially extending guide may be in the form of a slot or track.

In embodiments an edge of the opening at the rear of the syringe housing through which the plunger extends cooperates with the plunger to constrain the plunger against rotation relative to the syringe barrel. In embodiments the plunger comprises at least one axially extending guide which cooperates with the edge of the opening at the rear of the syringe housing through which the plunger extends for guiding movement of the plunger into the barrel. The guide means is preferably an axially extending slot. The edge of the opening may be shaped appropriately to achieve this. For example, the edge may comprise one or more radially inwardly directed formations e.g. lugs which cooperate with the guide means of the plunger.

In accordance with the present invention in any of its aspects and embodiments, preferably the syringe housing is free from formations extending radially outwardly from its walls. This may enable the syringe and syringe housing to move freely in the axial direction during actuation, reducing frictional forces resisting motion of the syringe housing in use.

The syringe housing may be of any suitable form, and may be assembled with the syringe in any suitable manner.

In some embodiments, the syringe housing comprises first and second sections which are closed around the syringe to provide the housing. In this manner, the syringe housing may clamp around the syringe barrel as it is closed around the barrel. In these embodiments, the syringe may be located in position relative to one section of the housing, and the other section or sections closed around the syringe to secure it in place relative to the housing. The first and second sections are preferably connected to one another along their opposed longitudinal edges.

The first and second sections may be discrete pieces which are joined to one another. In these embodiments the first and second sections may be configured to clip together, and may comprise suitable interlocking formations for this purpose. In other embodiments, the syringe housing is a single piece housing. In these embodiments, the first and second sections may be connected to one another via a hinge, preferably a living hinge, along one set of the opposed longitudinal edges. This may enable the sections to be formed as a single piece with the hinge using an injection moulding technique. The (other) set of opposed edges may be joined together in any suitable manner, for example by a resilient fit or clip arrangement as described in relation to embodiments in which the first and second sections are discrete sections.

In embodiments in which the syringe housing comprises first and second sections, the sections are preferably matching sections, and most preferably the housing comprises matching halves.

In embodiments in which first and second longitudinally extending sections of the housing are closed around the syringe, it is preferred that any gripping means extends at least in the circumferential direction to facilitate clamping to the syringe barrel.

In these embodiments in which the syringe housing comprises first and second sections, the rear end of the sections may be configured appropriately to fit around or over the rear flange, and/or constrain the rotational movement of the plunger as described above.

In some sets of embodiments, the syringe housing may comprise a sleeve which receives the syringe barrel and a rear end cover which cooperates with the sleeve to retain the syringe in the housing.

In accordance with a further aspect of the present invention there is provided an automatic injection device comprising a syringe, the syringe comprising a needle, a plunger, and a barrel having a rear flange; wherein the barrel and the rear flange are immobilised in a syringe housing such that they can be moved within the device by a force applied to the syringe housing, wherein the syringe housing comprises a sleeve which receives the syringe barrel and a rear end cover which cooperates with the sleeve to retain the syringe in the housing.

The invention in accordance with this further aspect may incorporate any or all of the features described in respect of the other aspects and embodiments of the invention.

It will be appreciated that the syringe housing may snugly fit around the barrel of the syringe to immobilise it. As in the earlier aspects and embodiments of the invention, preferably the housing is configured such that when the plunger is driven into the barrel in use, no axial force is transmitted to the barrel of the syringe through the rear flange.

In these further aspects and embodiments of the invention in which the syringe housing comprises a sleeve and a rear end cover, the sleeve and the rear end cover are separately formed pieces. In these embodiments, the sleeve is preferably a single piece sleeve. The syringe may then be dropped into the sleeve from the rear end, and the rear end cover located in place to retain the syringe within the housing. This may facilitate assembly, allowing the front portion of the device to be assembled before the syringe is inserted. It will be appreciated that the rear end cover comprises an opening through which the syringe plunger extends. Preferably the rear end cover is a rear end plate. The rear end cover need not cover the entire open area at the end of the sleeve provided that it at least retains the syringe within the syringe housing once the device is assembled. In embodiments, the rear end cover is located over the rear flange of the syringe to retain the syringe in the housing. Thus, the rear end cover is located behind the rear flange. The rear end cover will then be located between the rear flange and the rear free end of the plunger.

Preferably the rear end cover is located at least partially within the rear end of the sleeve.

In embodiments in which the syringe housing comprises a sleeve and a rear end cover, the rear end of the sleeve preferably comprises means for locating the rear end cover. For example, such means may comprise a groove or similar, in the same manner as discussed in relation to locating the rear flange of the syringe. The rear end of the sleeve may comprise resilient means e.g. tabs which deflect to allow the rear end cover to be inserted into the rear end of the sleeve. The resilient means may then retain the cover in place when the device is assembled.

The sleeve may comprise gripping means or any of the other features described above to allow it to snugly engage around the syringe barrel. If gripping means is provided, it preferably extends at least in the longitudinal direction. In embodiments in which gripping means are provided, the syringe may need to be pressed home into the syringe housing when dropped in through the open end of the sleeve.

In embodiments in which the syringe housing comprises a sleeve and a rear end cover, the rear end cover may cooperate with the plunger to constrain the plunger against rotation relative to the syringe barrel. Thus, the rear end cover may act to rotationally align the syringe plunger relative to the barrel as the plunger is driven into the barrel in use.

As discussed above, in these embodiments, the rear end cover of the syringe housing defines the opening through which the plunger extends. Thus, in embodiments the rear end cover is a rear end plate located over the rear flange of the syringe, and defining an opening through which the plunger extends. In these embodiments an edge of the opening may cooperate with the plunger to constrain the plunger against rotation relative to the syringe barrel as the plunger is driven into the barrel. This may be achieved in any of the manners discussed more generally above in relation to the syringe housing. In some embodiments therefore the plunger comprises axially extending guide means which cooperate with an edge of the opening in the end plate to guide movement of the plunger into the barrel. In embodiments the guide means comprises an axially extending track or slot. This may cooperate with the edge of the opening in any suitable manner. For example, the edge may comprise one or more radially inwardly directed formations which cooperate with the guide means of the plunger.

Preferably the end cover is configured such that it may be fitted over the rear end of the plunger after the plunger has been assembled with the barrel. In these embodiments the opening in the rear end cover should be of a suitable configuration to enable the cover to be passed over the plunger, e.g. the plunger rear flange, when suitably aligned therewith.

It will be appreciated that in order for the end cover to cooperate with the plunger as described in certain embodiments above to maintain rotational alignment of the plunger and/or enable the end cover to be fitted over the end of the plunger, it may be necessary to use a modified plunger, of a configuration designed to cooperate with the end cover. The syringe "pre-pack" which is subjected to regulatory approval does not include the plunger, and thus in certain applications the plunger which acts on a piston in the syringe barrel may be inserted into the syringe barrel subsequent to production of the approved pre-pack without the need to obtain reapproval. Thus, the pre-pack may be supplied without a plunger, allowing subsequent addition of a plunger, or may be supplied with a plunger which may be replaced with another plunger prior to use of the syringe. This may allow the use of customized plungers, for example which cooperate with the activation mechanism as described herein.

In any of its aspects or embodiments, it will be appreciated that the syringe housing forms part of an injection device for automatically delivering an injection. In embodiments of the invention, the syringe housing does not form part of the exterior of the device. The syringe housing is disposed within an outer housing of the syringe. The syringe housing is movable relative to the outer housing to advance or retract the syringe in use. The outer housing may be defined by one or more components. There may be one or more intermediate components disposed between the outer housing of the device and the syringe housing. In embodiments, the syringe housing is not exposed at any stage during activation of the device.

The syringe housing may comprise features to enable it to be interconnected with, and interact with other parts of the mechanism of the injection device during dispensing of the liquid.

In some embodiments the syringe housing may comprise at least one slot extending axially from the rear end of the housing. The slot may cooperate with an overlying part of the mechanism of the device in use as described below. In some embodiments the slot extends at least 50%, or at least 75% along the length of the housing from the rear end. In embodiments in which the syringe housing comprises first and second sections, each section may comprise such a slot.

In some sets of embodiments, the front end of the syringe housing is coupled to a front housing for protecting the needle. The front housing is preferably a separate component attached to the syringe housing. The front housing may protect the needle and guard against accidental needle stick injuries. The front housing is that part of the device which is intended to be located against the skin of the user in use. The needle is advanced and retracted relative to the front end of the front housing in use to deliver an injection. It is desirable that the user does not see the needle, with the needle only being advanced and retracted during operation of the device when it is pressed against the skin. This is also desirable for hygiene reasons.

In embodiments including a front housing, preferably the syringe housing is axially movable relative to the front housing. For example, the syringe housing may be configured to slide relatively into and out of the front housing. Preferably the syringe housing is not movable circumferentially relative to the front housing. In accordance with the invention, as the syringe housing is not movable relative to the syringe, movement of the syringe housing relative to the front housing will then result in a corresponding movement of the syringe relative to the front housing. In this manner, advancing and retracting of the needle relative to the front housing may be achieved by advancing or retracting the syringe housing relative to the front housing.

In embodiments, the syringe housing is axially movable relative to the front housing between a first retracted position and a second extended position corresponding to concealed and exposed positions of the needle. Preferably the first and second positions are predetermined positions. This may provide more reliable operation of the device, and reduce the risk of accidental contact with the needle. The first and second positions may be chosen as desired for a given device to result in the needle extending an appropriate distance from the front housing for insertion into a person in use, while being retracted from the end of the front housing an appropriate distance at other times. The distances may be selected taking into account factors such as e.g. the intended application of the device, type of liquid to be dispensed, relevant regulations, the distance through which the needle might accidentally travel relative to the front housing etc. For example, in embodiments the needle is spaced by around 3 mm from the front end of the front housing when in the retracted position. This has been found to be a suitable distance to meet legislation regarding avoidance of needle stick injuries. When the needle is to be used for a subcutaneous injection, it may be advanced to extend 6 mm beyond the front end of the font housing in use, while for intramuscular injections the needle may extend 9 mm beyond the front end of the front housing. Thus, in these cases, the total axial distance travelled by the needle will be 9 mm or 12 mm respectively, and the syringe housing is configured to travel a corresponding axial distance between its retracted and extended positions relative to the front housing.

In embodiments, therefore the front end of the syringe housing is coupled to a front housing for protecting the needle, the front housing being intended to be located against the skin of a user in use, wherein the syringe housing is axially movable relative to the front housing between a first retracted position and a second extended position corresponding to concealed and exposed positions of the needle.

To reduce the likelihood of needle stick incidents, to comply with regulations, and avoid injury to the user in attempting to remove the needle from the body, it is preferable that the needle, and hence the syringe housing, is configured to return to the retracted position automatically in use. In this way, the needle may be exposed only during actuation of the device to deliver an injection, and is located in a retracted position relative to the front end of the front housing before and after delivery of the injection. Preferably the syringe housing is biased toward the second retracted position relative to the front housing. This may be achieved in any suitable manner. In some sets of embodiments resilient means, such as a coil spring, is located between the front housing and the syringe housing to bias the syringe housing toward the retracted position. The syringe housing may comprise one or more axially extending bores for receiving the spring or springs. The front housing may then comprise corresponding locating means for the front end or ends of the springs. Such locating means may be provided by an end of the front housing, or suitable formations in the body of the front housing.

The syringe housing may comprise guide means for guiding the housing as it moves axially relative to the front housing. Such guide means may be of any suitable construction, and may comprise cooperating a pin and slot etc. In some embodiments, the syringe housing comprises a track, e.g. slot extending axially rearwardly from its front end which cooperates with a radially extending formation of the front housing to guide the syringe housing. In embodiments the radially extending formation is provided on a resilient leg.

Means may be provided to limit the degree of relative axial movement available between the front housing and the syringe housing. This may avoid the front housing and syringe housing becoming detached from one another. For example, such limiting means may comprise cooperating flanges, a flange and groove, or any suitable arrangement. In embodiments comprising guide means for guiding the movement of the syringe housing relative to the front housing, the guide means may comprise limiting means for this purpose.

In accordance with some sets of embodiments, the injection device comprising the syringe housing is configured to perform an automatic actuation cycle in use comprising the steps of; advancing the needle of the syringe for insertion, driving the plunger into the barrel for dispensing a liquid contained in the barrel, and retracting the needle.

The injection device may be configured to perform such an actuation cycle in any manner, and may be configured to operate in accordance with any conventional arrangement or in accordance with any of the further aspects and embodiments of the invention described below.

From a further aspect the present invention provides an automatic injection device comprising: a syringe having a needle, a barrel and a plunger; and driving means for driving the plunger into the barrel. In one aspect, the injection device is configured to perform an automatic actuation cycle in use comprising the stages of advancing the needle of the syringe for insertion, driving the plunger into the barrel for dispensing a liquid contained in the barrel, and retracting the needle. In one aspect, the device is configured such that during operation of the device, a driving force is transmitted from the driving means to the plunger during the dispensing stage, and such that a driving force is not transmitted to the plunger during the retraction stage to allow retraction of the needle. In a further aspect, the automatic injection device comprises a drive coupling arrangement between said driving means and said syringe. In one aspect, said drive coupling arrangement comprises a drive coupling part selectively transmitting or not transmitting force from the driving means to the plunger depending upon the rotational position of the coupling part. In another aspect, the device is configured such that, depending upon a configuration of the drive coupling arrangement, the syringe is driven forward during the needle advancement stage and the plunger is driven into the barrel during the dispensing stage for dispensing a liquid contained in the barrel.

The invention in accordance with this further aspect may incorporate any or all of the features described in respect of the other described aspects and embodiments of the invention. In particular, the device preferably comprises a syringe housing in accordance with any of the embodiments previously described. Any references to the syringe barrel may therefore be understood to apply equally to the syringe housing, within which, in these preferred embodiments, the syringe barrel is immobilised, unless the context demands otherwise. The injection device in accordance with the previous aspects of the invention in accordance with any of the embodiments described may conversely further comprise any of the features described in respect of the further aspects of the invention in any of their embodiments.

In accordance with the aspect of the invention set out above, a drive coupling arrangement is positioned between the syringe and driving means, such that in use, a driving force is selectively transmitted or not transmitted to the plunger depending upon the rotational position of a drive coupling part of the drive coupling arrangement. The rotational position of the drive coupling part determines whether or not the driving force is transmitted to the plunger. In this way, a driving force may be transmitted to the plunger during the dispensing stage, but not during the needle retraction stage depending upon the position of the drive coupling part. Additionally, in accordance with the invention, the drive coupling arrangement is configured such that during an initial needle advancement stage the syringe is driven forward to advance the needle, while in the subsequent dispensing stage the plunger is driven into the barrel. The present invention may thus provide more defined needle advancing, dispensing and retraction stages, as the stages are defined by the arrangement of an intermediate drive coupling arrangement.

The use of an intermediate coupling arrangement provides greater ability to control how and when a driving force is applied to the plunger by configuring the part or parts of the drive coupling arrangement appropriately. The device of the present invention may be used in conjunction with many different standard syringes. The use of the drive coupling arrangement avoids the need to adapt the design of the device to a specific syringe type, and facilitates greater accommodation of differences in the type or size of syringe, or the relative position of the syringe in the device, which may arise from slightly differing designs (e.g. as between differing manufacturers) or from manufacturing tolerances. This is particularly useful in allowing the device to cooperate with a range of standard regulatory approved syringes without requiring modification of the basic regulated syringe pre-pack.

Avoiding the need to rely on the plunger interacting directly with other parts of the device to control whether a driving force is applied or not applied to it is an improvement over known arrangements such as taught in GB 2410188 which inherently relies on small radial tags hooking onto and unhooking from the plunger whilst under tension.

The present invention may also overcome the problems associated with arrangements such of GB 2410188, in which considerable frictional forces may be generated between the plunger and barrel of the syringe and the housing as it moves, due to the scraping of the tags along the walls of the housing, and also as a result of the axial movement of the tags over the end of the plunger or barrel out of engagement therewith at certain points. By relying instead on the rotational position of a drive coupling part configured between the plunger and driving means to selectively transmit a driving force to the plunger, the mechanism does not require the use of radially movable elements to transmit forces to the plunger, and may avoid creating any additional frictional resistance opposing movement of the plunger or other parts of the syringe in use, allowing a reduction in the driving force necessary to drive the plunger into the barrel to be achieved. The present invention may also avoid the problems discussed above which may arise with arrangements such as those of GB 2410188 in which there is some clearance between the engaging parts prior to operation of the device, such that they may need to be driven into one another with considerable force to overcome the air gap, and the inertia of the stationary part, to cause movement to commence.

The device is therefore configured such that a driving force is applied to the plunger during a selected part or parts of the dispensing cycle and not during another part or parts by arranging the drive coupling arrangement such that the driving force is transmitted or not transmitted to the plunger during the respective parts of the cycle. In a dispensing cycle, it is necessary to retract the needle of the syringe after dispensing of liquid. In embodiments of the invention, the needle may only retract once the drive coupling part has rotated to a position which determines that the driving force is no longer transmitted to the plunger. By relying upon the position of the drive coupling part to control when the driving force is no longer applied to the plunger to permit needle retraction, the present invention provides the ability to more precisely define the start of the needle retraction stage, avoiding the risk of prematurely retracting the needle before dispensing has been completed.

The drive coupling arrangement may be provided in any manner, and may comprise one or more parts, provided that it includes a part wherein a driving force is selectively transmitted to the plunger depending upon the rotational position of the part, and wherein the needle is advanced or the plunger driven into the barrel for dispensing liquid depending upon the state of the drive coupling arrangement.

In accordance with the invention, the drive coupling part may be acted upon directly or indirectly, by the driving means. In some embodiments described below, the driving means may act on the drive coupling part via an intermediate part of the drive coupling arrangement. The drive coupling part preferably acts, directly or indirectly on the plunger. In some embodiments the drive coupling part acts on the plunger via an intermediate part of the drive coupling arrangement. In embodiments of the invention the drive coupling part rotates under the action of the driving force. In embodiments the drive coupling part moves axially as it rotates, preferably until it reaches a rotational position such that the driving force is no longer transmitted to the plunger. In embodiments of the invention the drive coupling part may rotate under the action of the driving force during the syringe advancing stage and during the dispensing stage.

The drive coupling part may be configured to rotate through any angle which determines that the drive force is no longer transmitted to the plunger. In embodiments the angle is less than 360 degrees, and preferably less than 180 degrees. Preferably the angle is at least 20 degrees, and preferably at least 40 degrees. In embodiments the angle may lie in the range of from 30 to 135 degrees, or from 60 to 135 degrees. In preferred embodiments wherein the drive coupling arrangement comprises first and second parts as described below, either of the first and second parts may rotate through an angle in any of the above ranges.

It will be appreciated that references to rotation herein, unless the context demands otherwise, refer to rotation about an axis parallel to the longitudinal axis of the device. Thus the rotation is about an axis parallel to the direction in which the driving force acts in use.

In embodiments the device is configured such that once the driving force ceases to be transmitted to the plunger, the barrel and plunger are free to move rearwardly thereby retracting the needle. In embodiments the needle may not retract until the driving force ceases to be transmitted to the plunger dependent upon the rotational position of the drive coupling part. The rotational position of the drive coupling part determines whether or not the driving force is transmitted to the plunger and whether or not the needle is able to retract. Thus, the rotation such that the driving force is no longer transmitted enables needle retraction to occur.

In embodiments guide means are provided to influence the movement of the drive coupling part. Preferably the guide means is located radially outwardly of the drive coupling part. Such guide means may be of any suitable form. In embodiments the movement of the part is guided by the travel of a pin in a slot. In some embodiments the device comprises a guide cylinder which cooperates with the part for guiding the part. The guide cylinder may be located radially outwardly of the coupling part. It will be appreciated that any guide arrangement may be used to result in appropriate movement of the coupling part.

The drive coupling part may be of any configuration. In embodiments the coupling part is at least part cylindrical.

In some sets of embodiments, the drive coupling arrangement comprises at least first and second parts which are configurable such that a driving force can be selectively transmitted or not transmitted between them in use depending upon the relative rotational positions of the parts, wherein the first and second parts are configured such that during operation of the device, a driving force is transmitted between the first and second parts during the dispensing stage for applying a driving force to the plunger, and such that a driving force is not transmitted between the first and second parts during the retraction stage to allow retraction of the needle.

In these embodiments, the drive coupling part provides one of said first and second parts.

In some embodiments, the injection device comprises driving means, a first part which is directly driven by the driving means, and a second part which contacts the plunger, the first and second parts being configured such that a driving force is selectively transmitted or not transmitted between the parts in use.

In accordance with a further aspect of the invention there is provided an automatic injection device comprising: a syringe having a needle, a barrel and a plunger; driving means for driving the plunger into the barrel; and a drive coupling arrangement between said driving means and said plunger. In one aspect, said drive coupling arrangement comprising at least first and second parts which are configurable such that a driving force can be selectively transmitted or not transmitted between them in use. In a further aspect, the first and second parts are configured such that during operation of the device, a driving force is transmitted between the first and second parts during a first stage corresponding to a dispensing stage for applying a driving force to the plunger, and such that a driving force is not transmitted between the first and second parts during a subsequent second stage corresponding to a retraction stage to allow retraction of the needle. In yet another aspect, the first and second parts are configured such that the driving force is selectively transmitted or not transmitted between the first and second parts depending upon the relative rotational positions of the parts.

Thus, the driving force applied to the first part of the coupling arrangement is selectively transmitted or not transmitted to the second part in use. In this manner, the two parts may selectively transmit or not transmit the driving force to the plunger in use.

This further aspect of the invention may include any or all of the features described in relation to the other aspects and embodiments of the invention to the extent it is not inconsistent therewith.

In this further aspect of the invention the device is preferably configured such that a driving force transmitted from the first part to the second part is selectively effective to drive the plunger into the barrel of the syringe depending upon the rotational position of the first part.

The invention in accordance with this further aspect may incorporate any or all of the features described in respect of the other aspects and embodiments of the invention described.

In accordance with these aspects and embodiments of the invention wherein the drive coupling arrangement comprises first and second parts, the first part is preferably acted upon, directly or indirectly, by the driving means, The second part preferably acts, directly or indirectly on the plunger. In some sets of embodiments the second part directly contacts the plunger. The first part may directly contact the driving means. In some sets of embodiments the first part directly contacts the second part to transmit a driving force thereto.

In accordance with the invention at least one of the first and second parts rotates to selectively transmit or not transmit the driving force to the plunger. In accordance with the invention in any of its embodiments, it will be appreciated that one or both of the first and second parts may rotate during operation of the device. In some embodiments the second part is configured to be rotatable under the action of the driving force transmitted thereto, and the first part is configured to rotate in an opposite sense to the second part under the action of the driving force.

In some sets of embodiments the second part is provided as part of the plunger of the syringe, and is preferably provided by a rear end part thereof, preferably the rear flange. In these embodiments the second part is not movable relative to the plunger. The second part is attached to the remainder of the plunger, and may or may not be integrally formed therewith. It will be appreciated that in accordance with the invention in any of its aspects the plunger need not resemble the plunger of a traditional manual syringe; it might simply be a member acting on a piston in the barrel to expel fluid. The second part referred to herein could then be provided as part of a member on the syringe resembling a conventional plunger. For example, the second part may be provided by replacing a conventional syringe plunger with a modified plunger, or fitting a modified end flange to a conventional plunger, or plunger member e.g. plunger rod. In these embodiments, the drive coupling part whose rotational position determines whether the driving force is transmitted to the plunger may provide the first part of the first and second parts, the second part being provided by a part of the plunger.

In other sets of embodiments the second part does not form part of the plunger. The second part is then provided as a separate part from said plunger. In these embodiments the second part is movable relative to the syringe plunger. The second part may move independently of the plunger. In embodiments the second part may rotate relative to the plunger. In preferred embodiments the second part comprises a member adapted to engage a syringe plunger handle. The plunger handle may be a conventional plunger handle. In some preferred embodiments the second part is in the form of a cup for receiving the end-flange of the plunger handle. By cupping around the end of the plunger, more reliable transmission of forces to the plunger may be achieved, even as the second part rotates. The second part preferably comprises a bearing surface for contacting the end of the plunger. In a preferred example the bearing surface comprises a part-spherical or otherwise rounded surface to reduce friction during relative rotation. For example, the plunger-facing surface of the second part may comprise a pip for contacting the plunger. In these embodiments the drive coupling part whose position determines whether a drive force is transmitted to the plunger in use may be provided by the second' part of said first and second parts. These embodiments may be used where it is desired to be able to use the device in conjunction with a standard syringe, including a plunger, without having to modify the plunger.

Where the second part is a separate part to the plunger, intended to contact the plunger, it may not do so initially, instead moving into contact with the plunger when a driving force is applied thereto by the first part. However, preferably the second part contacts the plunger before the first part transmits a driving force thereto. This may avoid additional forces being exerted on the plunger as a result of initial impact with the second part.

In some sets of embodiments, whether or not the second part forms part of the plunger, the first and second parts are configured such that when they are in a first rotational position relative to one another a driving force may be transmitted from the first part to the second part, and when they are in a second rotational position relative to one another no driving force may be transmitted from the first part to the second part in use. It will be appreciated that the driving force may be transmitted between the first and second parts over a range of relative rotational positions between the first and second rotational positions. In accordance with any of the embodiments of the invention, the first and second rotational positions are preferably predetermined positions.

In embodiments the first and second rotational positions may be separated from one another by a rotational angle in the range of, at least 60 degrees, or more preferably at least 80 degrees. The first and second rotational positions are separated from one another by less than 360 degrees. In some exemplary embodiments, the first and second parts move relative to one another through an angle of around 90 degrees from an initial relative rotational position to decouple from each other. In accordance with preferred embodiments the first and second parts are therefore selectively rotatably coupled to one another.

In some sets of embodiments, the first and second parts are configured to be selectively coupled or not coupled to one another to selectively transmit or not transmit the driving force therebetween. As used herein, parts are considered to be "coupled" to one another if an axial force may be transmitted from one part to the other. The parts may remain in engagement with one another when decoupled provided that an axial force may no longer be transmitted between the parts. In preferred embodiments, the first and second parts are configured to be coupled for transmitting, a driving force from the first part to the second part, and to be decoupled from one another to prevent transmission of a driving force from the first part to the second part. Preferably the first and second parts may therefore move between a first position relative to one another in which they are coupled to one another and a second position in which they are not coupled to one another.

Preferably the device is configured such that the second part may move axially with respect to the first part once the first part ceases to transmit the driving force to the second part. Preferably the second part may not move axially relative to the first part while the first part transmits the driving force thereto.

In some embodiments in which the drive coupling arrangement comprises first and second parts which are rotatable relative to one another, the second part rotates relative to the first part under the action of the driving force transmitted thereto by the first part. The second part preferably rotates into a given rotational position relative to the first part in which the driving force is no longer transmitted between the first and second parts. In some embodiments the second part is configured to rotate under the action of the driving force applied thereto by the first part between an initial rotational position relative to the first part in which the second part is coupled to the first part and a second rotational position in which the second part is decoupled from the first part. In embodiments in which the second part rotates, the second part preferably rotates during the needle advancing stage and the dispensing stage, preferably throughout each stage. In any of the embodiments in which the second part rotates, it preferably moves axially as it rotates. Thus the second part may move in a helical path.

In other embodiments the first part rotates under the action of the driving force relative to the second part into a given rotational position relative to the second part in which the driving force is no longer transmitted between the first and second parts. In such embodiments, the second part need not be capable of rotating. These embodiments may include those in which the second part forms a part of the plunger. In these embodiments, the first part preferably rotates during the needle advancing stage and the dispensing stage, preferably throughout each stage. The first part preferably moves axially as it rotates.

In some embodiments of the invention in any of its aspects wherein the device includes first and second parts, the first part is configured to move axially under the action of the driving means. Preferably the second part is configured to move axially with the first part under the action of the driving force transmitted by the first part while the first part transmits the force thereto. The first part drives the second part axially relative to the syringe, barrel during at least a part of a period in which it transmits the driving force to the second part. This enables the second part to drive the plunger into the barrel for dispensing liquid.

In embodiments of the invention the distance by which the first part travels axially before the driving force ceases to be transmitted to the second part and/or the distance that the first or second part travels relative to the other of the first and second parts before the driving force ceases to be transmitted to the second part, e.g. an azimuthal distance corresponding to an amount by which the parts rotate relative to one another, may used to control the distance that the plunger may be driven into the barrel, and hence the amount of liquid dispensed in use.

In some embodiments the second part is configured to rotate under the action of the driving force transmitted thereto by the first part as it moves axially with the first part. Thus, in embodiments, the second part may follow a helical path as it moves under the action of the driving force transmitted thereto by the first part. This enables the second part to rotate towards a position in which the first part no longer transmits a force thereto, but is also advantageous as by rotating while contacting the plunger to drive the plunger into the barrel, the forces applied to the plunger may be further reduced. In preferred embodiments the device is configured so as to permit relative rotational movement of the first and second parts when the first part transmits the driving force to the second part while preventing relative linear movement between the parts. In these embodiments the second part does not form part of the plunger, to enable it to rotate relative to the plunger.

In some sets of embodiments, whether or not the second part forms part of the plunger, the device is configured such that once the driving force is no longer transmitted from the first part to the second part, it continues to be applied to the first part but is no longer effective in driving the first part axially. In some embodiments the first part may reach an end stop preventing further axial movement of the first part relative to the barrel. For example, the first part may run out of travel in an axial slot which permits it to move axially relative to the barrel during driving of the plunger into the barrel. In preferred embodiments the device is configured such that once the driving force ceases to be transmitted from the first part to the second part, the barrel and plunger are free to move rearwardly thereby retracting the needle. The device is configured such that the needle is positively retracted relative to a front end of the device. This is in contrast to some arrangements in which a needle sheath is advanced relative to the needle after dispensing has occurred.

In embodiments the needle is not able to retract until the driving force ceases to be transmitted from the first part to the second part dependent upon the relative rotation of the parts. The relative rotational positions of the first and second parts determine whether or not the driving force is transmitted to the plunger and determine whether or not the needle is able to retract. Thus, the rotation which determines that the driving force is no longer transmitted enables needle retraction to occur. The plunger and barrel can move together as a unit. In embodiments the plunger and barrel move rearwardly relative to the first part. This may then allow the plunger and barrel of the syringe to also retract relative to the first part. In some sets of embodiments, the second part is configured to retract relative to the first part when the first part ceases to transmit a driving force thereto. The second part may be driven rearwardly by the movement of the plunger as it retracts.

The barrel and plunger may be configured to retract in any manner. As described above, in preferred embodiments the syringe barrel is biased towards a retracted position. Thus, in the absence of a forward driving force being exerted on the plunger the syringe barrel automatically returns towards the retracted position under the action of the biasing means. The retraction may occur under the action of a return spring or springs. It will be appreciated that the return spring or springs need only be able to produce a relatively small driving force relative to the main driving force, as there is limited resistance to the retraction of the syringe as a whole, in comparison to the significant forces to be overcome when driving the needle into the body, and forcing liquid through the needle via the plunger. A relatively small return force is all that is required to drive the plunger rearwardly, as it is no longer subject to the forward driving force.

In preferred embodiments, the needle retracts into a concealed position, preferably within a front housing of the device.

The device should be configured such that the plunger may move rearwardly a sufficient distance to enable the needle of the syringe to retract into a concealed position. For example such a distance may be such as to enable the needle to be pulled back out of the body and into a front housing. This retraction distance may correspond to the total distance travelled by the needle during insertion.

In preferred embodiments means is provided to disable the device after operation i.e. once the needle has been retracted. Any one or more of a number of arrangements may be used to disable the device. This may be achieved by arranging the drive coupling arrangement such that it may not transmit a driving force to the plunger again once the needle has been retracted. In some embodiments the device comprises means for retaining the second part in a position relative to the first part in which the first part may not transmit a driving force thereto. In preferred embodiments, therefore, the device comprises means for retaining the second part in a decoupled position relative to the first part.

In some sets of embodiments in which the second part retracts relative to the first part, the device comprises means for restraining the second part against movement forward in the axial direction from its retracted position. This may prevent the second part from being effective in urging the plunger, and hence needle and barrel of the syringe forward, thus avoiding the possibility that the needle might be advanced and exposed once more. This reduces any risk that the device could be handled in a manner which might cause the second part to move forward axially along the path that it had earlier retracted to push the plunger and needle forward. While the return springs should bias the needle rearwardly and oppose any movement of the plunger in the forward direction, this arrangement provides greater protection against the remote possibility that the device could be handled in a manner such that the relatively small return spring force could be overcome. Any suitable restraining arrangement may be used to achieve this, such as a barb, hook etc. In some embodiments restraining means comprises hook means, preferably resilient hook means. Preferably the first part comprises the restraining means. The restraining means may be configured to permit the second part to move past the restraining means in the rearward direction and not to allow the second part to move past the restraining means in the forward direction. This may enable the second part to retract as the plunger retracts, but not to move forward once more after the plunger has retracted a given distance. The first and second parts may cooperate with one another in any suitable manner to provide the appropriate relative motion therebetween to result in the driving force being selectively transmitted therebetween. In some embodiments guide means are provided to influence the movement of the first and/or second parts under the action of the driving force. In embodiments guide means are provided to influence the relative movement of the first and second parts.

In some sets of embodiments, in which the device comprises guide means for guiding the relative movement of the first and second parts, the guide means may be provided separately from the first and second parts. In some embodiments the first and second parts both move, and preferably rotate. In these embodiments the first and second parts may comprise cooperating parts for this purpose. For example, they may be connected by a cam arrangement, or by engaging lugs and tracks etc. However, in preferred embodiments the relative movement of the first and second parts is determined by the travel of a protrusion such as a pin or lug, in a slot. In embodiments, the second part comprises the protrusion and the first part comprises the slot. In these embodiments the slot should be configured as appropriate to guide the intended rotational and/or linear motion of the first and second parts relative to one another. In embodiments the slot comprises a first portion for retaining the first and second parts coupled to one another, and a second portion enabling the first and second parts to decouple from one another, i.e. move independently of one another. The first portion is preferably configured to allow relative rotational movement of the first and second parts and prevent relative axial movement between the parts. The second portion is preferably configured to allow relative linear movement and prevent relative rotational movement between the parts.

In embodiments the first portion is a circumferentially extending portion and the second portion is a linear portion. The linear portion preferably extends rearwardly from the first portion to enable the second portion to move rearwardly relative to the first portion as it decouples therefrom. In some embodiments the slot is an L shaped slot. In some embodiments in which the second part is guided by a rear leg of a slot in the first part, the slot comprises the means for restraining the second part e.g. hook means.

As described above, as well as moving relative to one another, in embodiments the first and second parts also move together under the action of the driving force in the axial direction. In preferred embodiments the device further comprises guide means for guiding the movement of the first part and/or the second part under the action of the driving force. The guide means may be of any suitable type, and may be of a similar type as described with respect to the guide means for guiding movement of the first part relative to the second part, e.g. a protrusion-slot arrangement. The same guide means may guide both the first and second parts and so might also influence their relative movement, or different guide means may be provided. In embodiments in which the second part is provided as part of the plunger, only guide means for influencing the movement of the first part need be provided.

In some embodiments, the guide means comprises respective slots which cooperate with protrusions of the first and second parts. The use of a protrusion and slot arrangement is advantageous as it reduces the level of frictional force generated opposing movement of the first and second parts relative to one another and the remainder of the device as they move under the action of the driving force. In some embodiments, the only radial contact between axially moving parts may be provided at the points where protrusions associated with the first and second parts respectively contact slots on the first part and guide means respectively.

In some sets of embodiments, the guide means comprises a slot comprising at least a helical portion for guiding the second part. This may cause the second part to rotate relative to the first part as it moves axially under the action of the driving force. The guide means should be configured to allow linear movement of the second part in embodiments in which there is relative linear movement of the second part relative to the first part when the force is no longer transmitted to the second part. In embodiments, the slot further comprises a linear portion connected to a front end of the helical portion. The linear portion may provide a rear leg to the slot. In embodiments the guide means comprises a slot comprising at least a linear portion for guiding the first part. In some preferred embodiments, the slot may also comprise a rear inclined portion for purposes described below.

In some sets of embodiments the first part is configured to rotate under the action of the driving force relative to the second part to bring at least a portion of the first part into a rotational alignment with at least a portion of the second part such that a driving force is no longer transmitted to the second part.

In accordance with a further aspect of the invention there is provided an automatic injection device. In one aspect, the automatic injection device comprises a syringe having a needle, a barrel and a plunger. In another aspect, the automatic injection device comprises driving means for driving the plunger into the barrel. In one aspect, the injection device is configured to perform an automatic actuation cycle in use comprising the stages of; advancing the needle of the syringe for insertion, driving the plunger into the barrel for dispensing a liquid contained in the barrel, and retracting the needle. In a further aspect, the device further comprises a drive coupling arrangement between said driving means and said syringe. In one aspect, said drive coupling arrangement comprises at least first and second parts which are configurable such that a driving force can be selectively transmitted or not transmitted between them in use. In an additional aspect, the first and second parts are configured such that during operation of the device, a driving force is transmitted between the first and second parts during the dispensing stage for applying a driving force to the plunger, and such that a driving force is not transmitted between the first and second parts during the retraction stage to allow retraction of the needle. In another aspect, the first and second parts are configured such that the driving force is selectively transmitted or not transmitted between the first and second parts depending upon the relative rotational positions of the parts. In still a further aspect, the first part is configured to rotate relative to the second part under the action of the driving force to bring at least a portion of the first part into a rotational alignment with at least a portion of the second part such that a driving force is no longer transmitted to the second part.

This further aspect of the invention may include any or all of the features described in relation to the other aspects and embodiments of the invention to the extent it is not inconsistent therewith.

In these further aspects and embodiments of the invention, the device is preferably configured such that, depending upon a configuration of the drive coupling arrangement, the syringe is driven forward during the needle advancement stage and the plunger is driven into the barrel during the dispensing stage for dispensing a liquid contained in the barrel.

In these aspects and embodiments of the invention the first part preferably rotates and the second part does not rotate. The first part may rotate into a position to enable the first and second parts to decouple from one another.

These embodiments are particularly applicable to arrangements in which the second part forms a part of the plunger. In embodiments the portion of the second part is provided by a part of the plunger, preferably by a rear flange thereof.

In these embodiments the device preferably comprises means for constraining the second part and plunger against rotation as the plunger is driven into the barrel in use. This may help maintain precision in operation, and ensure that the driving force ceases to be transmitted at the expected point as a result of rotational alignment between the first and second parts. Such restraining means may be provided by cooperation between the plunger and a rear part of a syringe housing as described above. In preferred embodiments the plunger comprises axially extending guide means which cooperates with an opening at the rear end of the housing to constrain the plunger against rotation as it is driven into the barrel in use. The first and second parts move axially under the action of the driving force as the first part rotates relative to the second part.

In preferred embodiments the portion of the first part rotates into a rotational alignment with the second part such that a surface of the first part no longer bears against a surface of the second part for transmitting a driving force thereto. In some embodiments the first part rotates such that at least a portion thereof is brought into a rotational alignment with at least a portion of the second part to enable at least a portion of the second part to move out of axial engagement with the first part.

In embodiments, the first part rotates into a position which permits relative axial movement between the first and second parts. In these embodiments the portion of the second part may have a configuration which enables the second part to move out of axial engagement with the first part only when the portion is in a given rotational alignment with a portion of the second part. The second part may then move rearwardly relative to the first part for retracting the needle.

The portions of the first and second parts may be configured in any suitable manner such that a driving force is no longer transmitted between the parts when the portions reach a given relative rotational alignment. For example, one portion might rotate into alignment with a track in the other portion to permit relative axial movement etc.

In preferred embodiments the portion of the first part comprises an opening which rotates into alignment with the portion of the second part. When the opening is brought into alignment with the second part, the first part is no longer able to exert a driving force on the second part. In embodiments the opening and said second part are configured such that said second part may pass through said opening only when the opening has rotated into said rotational alignment therewith.

In embodiments in which the first part comprises an opening, preferably the opening is a central opening in the first part. By central it is meant that the opening is radially central. Preferably the opening is centred around the longitudinal axis of the device. In preferred embodiments in which the second part is provided by a rear end or flange of the plunger, the opening is configured such that the rear end of the plunger may pass through the opening when the opening has rotated into rotational alignment with said portion of said second part.

In embodiments the opening defines a rotationally asymmetric shape. In embodiments the portion of the second part is of a shape such that the second part may only pass through the opening when the portions of the first and second parts are in the given rotational alignment. The opening may have a shape corresponding to the shape of the portion of the second part, and in preferred embodiments, to the shape of the rear end of the plunger which provides the second part. The opening may then act as a slot for the key provided by the second part. The opening and the portion of the second part are appropriately shaped to enable the second part to pass through the opening when the first part is suitably aligned therewith. In embodiments the shape of the parts is a transverse shape, and the opening is a transversely extending opening.

In some embodiments the first part rotates into a position enabling the second part to retract through said portion of the first part when the driving force is no longer transmitted to the second part. Thus, the second part (and the plunger) may retract through the first part during the needle retraction stage. In these embodiments, the driving means will be prevented from acting again on the plunger via the first part on retraction of the second part with the plunger.

In these embodiments wherein a portion of the first part is brought into rotational alignment with a portion of the second part the device comprises guide means for influencing the movement of the first part. In these embodiments movement of the first part may be guided in any suitable manner, e.g. using a pin and slot arrangement as discussed above. For example, a guide cylinder may be provided.

It will be appreciated that in accordance with the invention in any of the aspects in which the drive coupling arrangement comprises first and second parts, in some embodiments at least the first part, and in certain embodiments, both the first and second parts are cylindrical. In embodiments the second part is disposed radially inwardly of the first part. The parts may be of any suitable cross sectional shape, and may or may not be circular cylindrical.

In some embodiments in which guide means are provided for guiding the movement of the first and/or second parts under the action of the driving force, the guide means comprises a guide member, preferably a guide cylinder. Preferably the guide means is disposed radially outwardly of the first and second parts. In any embodiment in which first and second parts are provided, preferably the movement of the first and/or second parts and/or the relative movement of the first and second parts is influenced by the travel of a pin in a slot.

Prior to dispensing of liquid it is necessary to advance the needle. During an actuation cycle, it is desirable that a driving force is not transmitted to the plunger to drive the plunger into the barrel until the needle has been advanced to enable it to be inserted in the skin to the intended delivery depth. Otherwise liquid may prematurely leak from the device, failing to enter the skin at all, or at least to reach the target depth at which it is most effective. This is a problem that may occur with certain prior art arrangements which apply a force only to the plunger during the needle advancement stage, relying upon the initial resistance of the liquid in the barrel to resist movement of the plunger into the barrel initially. In practice, it is not possible to always avoid liquid being prematurely dispensed in such arrangements and whether or not this occurs may depend upon operating conditions as well as the construction of the syringe, nature of the liquid etc, making operation unpredictable.

As discussed above, in embodiments of the invention, the device is configured such that the drive coupling arrangement results in the syringe being driven forward to advance the needle in a needle advancing stage, and to drive the plunger into the barrel during a subsequent dispensing stage.

In embodiments of the invention, whether or not the drive coupling arrangement comprises first and second parts, the device is configured such that the syringe is driven forward to advance the needle during the needle advancement stage and the plunger driven into the barrel for dispensing liquid in the dispensing stage depending upon the arrangement of the drive coupling arrangement. In this manner, the device may be configured such that there is no resultant axial force on the plunger during the needle advancing stage. Thus distinct needle advancement and dispensing stages are provided depending upon the state of the drive coupling arrangement. The needle advancing and dispensing stages are controlled by the drive coupling arrangement, and the drive coupling arrangement controls the transition between these stages.

In some sets of embodiments the drive coupling arrangement is configured such that a driving force transmitted to the plunger is selectively effective to drive the plunger into the barrel wherein during the needle advancement stage the syringe is driven forward to advance the needle and wherein during the dispensing stage the plunger is driven into the barrel to dispense liquid.

In embodiments a driving force is transmitted to the barrel during a needle advancement stage for driving the needle forward, and to the plunger and not the barrel during a subsequent dispensing stage for driving the plunger into the barrel. The driving force may be transmitted to the plunger and barrel during the needle advancement stage or to the barrel and not the plunger. It will be appreciated that the syringe is preferably immobilized in a syringe housing, and the driving force is then transmitted to the barrel via the syringe housing. Thus the drive coupling arrangement will act on the barrel via the syringe housing.

In some sets of embodiments the transition between the needle advancing and dispensing stages is controlled by the movement of a part of the drive coupling arrangement, preferably by the rotation of the part. In embodiments the part is a different part to the coupling part whose rotational position controls whether a driving force is transmitted to the plunger during the dispensing and retraction stages. In these embodiments the part is configured to move under the action of the driving force from a first position wherein the driving force is effective to drive forward the syringe for advancing the needle to a second position wherein the driving force is effective to drive the plunger into the barrel to dispense liquid. In embodiments, the part may thus move from a first position in which the driving force is transmitted to the plunger and the syringe barrel to a second position wherein the driving force is transmitted to the plunger and not the syringe barrel. In some sets of embodiments the part of the drive coupling arrangement is coupled to the syringe barrel and plunger during the needle advancing stage and to the plunger and not the syringe barrel during the dispensing stage.

In some embodiments, the driving force transmitted to the plunger is not effective to drive the plunger into the barrel when the said drive coupling part (whose rotational position controls whether a driving force is transmitted to the plunger or not in the dispensing and retraction stages) is in a first rotational position and is effective to drive the plunger into the barrel when the drive coupling part has rotated into a second rotational position.

In preferred embodiments the needle is driven forward from a retracted concealed position during the needle advancement stage. Preferably the device is configured such that the needle is advanced by a predetermined axial distance before the plunger is driven into the barrel to dispense liquid.

In some embodiments in which the drive coupling arrangement comprises first and second parts, the force transmitted from the first part to the second parts is selectively effective to drive the plunger into the barrel of the syringe. In embodiments the force transmitted to the second part by the first part is not effective to drive the plunger into the barrel during a first part of a period in which the force is transmitted to the second part. This may be achieved by arranging the device such that there is initially no resultant axial force on the plunger.

In embodiments, the device is configured such that there is no relative axial movement between the plunger and barrel during a first part of period during which the first part transmits a driving force to the second part, and such that there is relative axial movement between the plunger and barrel during a second period during which the first part transmits a driving force to the second part. In this way, initially the plunger and barrel do not move axially relative to one another to advance the needle, and then the plunger moves axially relative to the barrel to drive the plunger into the barrel. This is achieved using the drive coupling arrangement.

In preferred embodiments the needle is driven forward from a retracted concealed position to an exposed position for insertion of the needle into the patients during the first period during which a driving force is transmitted to the plunger, or during which, in embodiments, the first part transmits a driving force to the second part. Preferably the device is configured such that the needle is advanced by a predetermined axial distance before the plunger is driven into the barrel to dispense liquid.

Any suitable arrangement may be used to result in the force transmitted to the plunger resulting or not resulting in relative axial movement of the plunger and barrel. In embodiments relative axial movement between the plunger and barrel is provided selectively depending upon the position of the first part. In some embodiments the first part is configured to move a predetermined distance in the axial direction before relative movement between the plunger and barrel is possible. This may allow the first part to advance the plunger and barrel, and provide control over the distance the needle is advanced before dispensing commences. The position of the first part may be used to directly or indirectly determine whether the force transmitted to the plunger results in relative axial movement between the plunger and barrel.

In some sets of embodiments the first part is initially not movable axially relative to the barrel of the syringe, and moves to a position in which it is movable axially relative to the barrel of the syringe to drive the plunger into the barrel. In embodiments in which the barrel is located in a syringe housing, the first part may move into alignment with an axial slot in the housing. The first part may initially engage the syringe barrel, or a syringe housing in embodiments having such a housing, to prevent relative axial movement between the first part and the barrel.

Preferably the positions of the first part are relative rotational positions. In preferred embodiments, the first part rotates into a position under the action of the driving force enabling relative axial movement of the barrel and first part for driving the plunger into the barrel. The first part may rotate in the opposite sense to the second part under the action of the driving force in embodiments in which the second part rotates under the action of the force transmitted thereto. For example, the first part may rotate into alignment with a slot to permit the relative movement. Rotational arrangements are advantageous in avoiding frictional effects associated with prior art arrangements relying e.g. on radial tags etc. As the first part moves axially during this period to drive the barrel and plunger forward for needle insertion, the first part may follow a helical path.

In accordance with preferred embodiments, therefore, the driving force transmitted from the first part to the second part in use is selectively effective in driving the plunger into the barrel in use depending upon the rotational position of the first part.

In accordance with the invention in any of its aspects and embodiments, movement of the first part to result in the plunger being selectively driven into the barrel may be guided in any suitable manner. This may be accomplished by the same guide means as used to guide the axial movement of the first part under the action of the driving force. In preferred embodiments the movement is guided by the travel of a pin or other protrusion in a slot. In embodiments in which the first part rotates to allow relative movement between the plunger and barrel, the guide means may comprise a slot having at least an inclined portion for guiding rotation of the first part. In embodiments, the first part does not rotate further after reaching a position permitting relative axial movement of the first part and the barrel. In some embodiments, movement of the first part may then be guided by a linear slot. In these embodiments, the guide means may comprise a slot having a rear inclined portion for guiding rotation of the first part and a front linear portion for guiding linear movement of the first part.

In other embodiments the first part may indirectly cause the driving force to be selectively effective to drive the plunger into the barrel. In some embodiments, a driving force transmitted by the first part to the second part may also be transmitted to a third part of the drive coupling arrangement, and may be selectively effective to drive the plunger into the barrel depending upon the position of the third part. Such arrangements are particularly applicable to embodiments in which the second part is provided as part of the plunger. The first part may engage the third part to transmit the driving force thereto. For example, a front end of the first part may engage the third part.

In embodiments, the drive coupling arrangement comprises a third part, wherein the first part is configured to transmit a driving force to the third part, wherein the third part is configured to move under the action of the driving force between a first position in which the driving force is transmitted to the barrel of the syringe, and a second position in which the driving force is not transmitted to the barrel of the syringe. Preferably the third part rotates between the first and second positions, and the first and second positions are thus rotational positions. In some embodiments, the third part rotates from a position in which it may not move axially relative to the barrel to a position in which it may move axially relative to the barrel. In embodiments the third part engages a rear end of a syringe housing until it reaches the second position. The third part may rotate into alignment with an axially extending slot in the syringe housing in a similar manner to embodiments described above in which the first part is selectively coupled to the syringe housing while transmitting a force to the second part. Effectively the third part moves from a position in which it is coupled to the barrel to a position in which it is not coupled to the barrel. Preferably guide means is provided for influencing the movement of the third part. The movement of the third part may be influenced using appropriate guide means as discussed in relation to the other embodiments above, wherein the first part controls whether or not the driving force is effective to drive the plunger into the barrel. In embodiments the movement of the third part is determined by the travel of a pin in a slot.

As described above, in any of the aspects and embodiments of the invention, the distance that the needle is driven forward before the plunger is driven into the barrel should be sufficient to overcome any clearance between the end of the needle and the front end of the device, and cause the needle to extend beyond the end of the device, e.g. front housing a distance corresponding to an intended injection depth. It has been found that by providing clearer definition between the needle insertion and dispensing parts of the actuation cycle to be achieved, as a result of the use of the drive coupling arrangement to control these stages of the operation, the present invention may allow more precise control over injection depth to be achieved, as the distance that the needle moves axially before dispensing occurs may be predetermined, by arranging the first and second parts such that the force transmitted to the plunger is not effective for depressing the plunger until the needle has been advanced a desired distance. As the invention may provide greater confidence in the reliability of the distance the needle is advanced, it may be possible to increase the distance that the needle is retracted into e.g. the front housing of the device prior to actuation of the device without compromising the effectiveness of the device, or consistency of injection depth, thus providing increased safety, and reduced risk of needle stick injury.

It will be appreciated that the device in accordance with the invention may provide greater control over the quantity of liquid dispensed. This is possible due to the ability to avoid premature release of liquid, and also, in embodiments, as the distance of axial travel of the plunger may be readily controlled by setting the distance of axial travel of the second part while transmitting the driving force to the plunger. In embodiments, the rotation of the first and/or second parts to selectively transmit or not transmit the driving force to the plunger, or to selectively push the plunger into the barrel provides a clear start and end point to the insertion and/or dispensing portions of the cycle.

When viewed from another aspect the invention provides an automatic injection device comprising: a syringe having a needle, a barrel and a plunger; driving means for driving the plunger into the barrel; and a drive-coupling part between said driving means and said plunger, said drive coupling part selectively transmitting or not transmitting force from the driving means to the plunger depending upon the rotational position of the coupling part.

The present invention in accordance with this aspect may incorporate any or all of the features described in relation to the other aspects of the invention. Thus in some embodiments the drive coupling part is part of a drive coupling arrangement comprising first and second parts as in accordance with the previous aspect of the invention, the selective transmission being dependent on the relative rotational positions of the two parts.

In accordance with another aspect, the present invention provides an automatic injection device comprising: a syringe having a needle, a barrel and a plunger; driving means for driving the plunger into the barrel; and a drive coupling arrangement between said driving means and said plunger, said drive coupling arrangement comprising at least first and second parts which are configurable such that a driving force can be selectively transmitted or not transmitted between them in use.

In accordance with a further aspect the present invention provides an automatic injection device. In one aspect, the automatic injection device comprises a syringe having a needle, a barrel and a plunger. In another aspect, the automatic injection device comprises driving means for driving the plunger into the barrel. In a further aspect, the injection device is configured to perform an automatic actuation cycle in use comprising the stages of; advancing the needle of the syringe for insertion, driving the plunger into the barrel for dispensing a liquid contained in the barrel, and retracting the needle. In one aspect, the automatic injection device is configured such that during operation of the device, a driving force is transmitted from the driving means to the plunger during the dispensing stage, and such that a driving force is not transmitted to the plunger during the retraction stage to allow retraction of the needle. In an additional aspect, the automatic injection device comprises a drive coupling arrangement between said driving means and said plunger. In a further aspect, said drive coupling arrangement comprises at least first and second parts which are configurable such that a driving force can be selectively transmitted or not transmitted between them in use depending upon the relative rotational positions of the parts. In one aspect, the first and second parts are configured such that during operation of the device, a driving force is transmitted between the first and second parts during the dispensing stage for applying a driving force to the plunger, and such that a driving force is not transmitted between the first and second parts during the retraction stage to allow retraction of the needle. In a further aspect, the second part comprises a member adapted to engage a syringe plunger handle, wherein the second part is configured to rotate relative to the first part under the action of the driving force transmitted thereto by the first part in use, the second part being rotatable into a given rotational position relative to the first part in which the driving force is no longer transmitted between the first and second parts in use. In still a further aspect, the first part is initially not movable axially relative to the barrel of the syringe, and is rotatable under the action of the driving force to a position in which it is movable axially relative to the barrel of the syringe to drive the plunger into the barrel.

In accordance with a further aspect the present invention provides an automatic injection device. In one aspect, the automatic injection device comprises a syringe having a needle, a barrel and a plunger. In an additional aspect, the automatic injection device comprises driving means for driving the plunger into the barrel. In a further aspect, the injection device is configured to perform an automatic actuation cycle in use comprising the stages of; advancing the needle of the syringe for insertion, driving the plunger into the barrel for dispensing a liquid contained in the barrel, and retracting the needle. In one aspect, the device further comprises a drive coupling arrangement between said driving means and said syringe. In another aspect, said drive coupling arrangement comprises at least first and second parts which are configurable such that a driving force can be selectively transmitted or not transmitted between them in use. In a further aspect, the first and second parts are configured such that during operation of the device, a driving force is transmitted between the first and second parts during the dispensing stage for applying a driving force to the plunger, and such that a driving force is not transmitted between the first and second parts during the retraction stage to allow retraction of the needle. In one aspect, the first and second parts are configured such that the driving force is selectively transmitted or not transmitted between the first and second parts depending upon the relative rotational positions of the parts. In an additional aspect, the first part is configured to rotate relative to the second part under the action of the driving force to bring at least a portion of the first part into a given rotational alignment with at least a portion of the second part such that a driving force is no longer transmitted to the second part. In another aspect, the first part comprises an opening which rotates into alignment with said at least a portion of the second part. In a further aspect, said second part is provided as part of said plunger. In still a further aspect, the automatic injection device is configured such that, depending upon a configuration of the drive coupling arrangement, the syringe is driven forward during the needle advancement stage and the plunger is driven into the barrel during the dispensing stage for dispensing a liquid contained in the barrel.

The present invention in accordance with these further aspects and embodiments may include any or all of the features described with respect to the other aspects of the invention to the extent they are not mutually inconsistent therewith.

In accordance with the invention in any of its aspects and embodiments, the driving means may be of any suitable type capable of providing a force urging the first part in the axial direction, and may, for example comprise a source of compressed gas which may be controllably released to provide the driving force. However, in preferred embodiments, the driving means comprises spring means. The spring means may comprise any form of spring or springs, but preferably comprises a coil spring.

In a subset of embodiments, the driving means comprises a spring which contacts a rear end of the first part for driving the first part. In some embodiments, the spring is mounted over a rear end of the first part. Preferably the first part comprises resilient rear legs over which the spring is mounted. The spring may be seated against a non axially movable surface at the rear end of the device. In some embodiments in which the device comprises a guide member, the spring is seated against the rear end of the guide member. In accordance with the invention in any of its embodiments, the injection device may comprise an outer housing which is gripped by a user in use. The outer housing may comprise formations to facilitate gripping, especially by users whose dexterity is impaired. The outer housing may comprise a tactile surface material. The outer housing preferably is joined to the front housing of the device. Thus, the outer housing and front housing cooperate to provide the exterior of the unit as seen and handled by a user. The housings protect the mechanism and syringe from the environment, or tampering.

In preferred embodiments the device comprises a viewing window to enable the user to view the position of the plunger before and after actuation of the device. This is preferably configured to allow a user to see whether the contents of the syringe has been fully expelled or not. This is novel and inventive in its own right and thus when viewed from a further aspect, the invention provides an automatic injection device for a syringe comprising a needle, a plunger and a barrel, wherein the device comprises a viewing window allowing a user to see the position of the plunger in the barrel.

This aspect of the invention may incorporate any or all of the features of any other aspects or embodiments of the invention.

The presence of a viewing window may enable a user to check that a dose of liquid has been fully dispensed by looking at the position of the plunger in the barrel, and/or the amount of liquid visible in the barrel. The viewing window preferably extends axially along the syringe housing a distance sufficient to enable viewing of the plunger in its most fully retracted position expected prior to dispensing of a dose of liquid and its most fully extended position expected after dispensing of the dose of liquid. In other words, the viewing window preferably extends axially over the full intended distance of travel of at least the front end of the plunger. This is advantageous as the user may more easily see if the liquid has not been (fully) dispensed as expected, by observing the content of the barrel, and the position of the plunger after activation, rather than merely being able to see that the plunger has been depressed to some extent relative to an initial position as may be the case with a viewing window which does not extend a significant distance along the barrel. In preferred embodiments the viewing window has a length of at least 70%, and preferably at least 90% of the length of the barrel. In some embodiments the viewing window has a length to permit viewing of the full length of the barrel.

It will be appreciated that it is necessary to initiate the automatic injection delivery cycle in some manner. In embodiments, the device comprises activation means adapted to be operated by a user to trigger automatic injection delivery. For ease of operation it is desirable that the activation step be simple, for example involving a single action by the user, but resistant to accidental or inadvertent operation. The activation means may comprise a lever, button or the like, or any suitable arrangement. In embodiments the device is configured to be activated by pressing a front end of the device against the skin. In embodiments in which the device comprises an outer housing, the outer housing may be configured to be axially movable relative to a front housing of the device, to enable activation of the device by urging the outer housing toward the front housing of the device. The device may then be activated by grasping the outer housing, and pressing downward with the front end of the device held against the skin. In accordance with the invention, once the device has been initially triggered, the remainder of the injection cycle, i.e. needle advancement, dispensing and needle retraction, occurs automatically without further intervention by the user. The device is configured such that the transitions between the needle advancement, dispensing and retraction stages occur automatically.

In embodiments of the invention, the driving means is prevented from exerting a driving force prior to activation of the device. Thus in some embodiments, automatic injection delivery cycle is triggered by releasing the driving means to enable it to exert the driving force, and the activation step is operable to release the driving means to enable it to exert a driving force. This may be achieved in any suitable manner. The activation step may be operable to release a catch or detent which restrains a resilient force of the driving means. The activation step may be operable to release the driving means directly, or by releasing a component coupled thereto. In embodiments in which the driving means acts directly on a first part, the activation may release the first part to release the driving means.

In some embodiments in which the driving means acts on a first part, the first part is restrained against movement under the action of the driving means until an activation step is carried out. In embodiments the activation step may be operable to release the first part by releasing retaining means configured to prevent movement of the first part under the action of the driving means. The retaining means may be a part of the first part, and in some embodiments a rear end of the first part comprises the retaining means. The activation step may release the retaining means by disengaging the retaining means. In embodiments the activation step is operable to disengage the retaining means by engagement with a surface. In embodiments in which the activation step involves an axial movement of the outer housing of the device relative to the front housing, the outer housing may directly engage the retaining means to disengage the retaining means.

In embodiments the retaining means comprises one or more hooks which hook over a flange of the device—e.g. provided by a rim. In embodiments in which the first part comprises resilient rear legs, each leg may define a hook at its rear end. The flange may be provided by any part of the device. In embodiments, in which the device comprises guide means, the rim may be provided by an end of the guide means. In some sets of embodiments, the activation step is operable to disengage the retaining means by unhooking hooks of the retaining means from the rim. The hooks may be configured to be unhooked in any manner during activation. In embodiments the hooks are unhooked by engagement with a surface, preferably an end of the outer housing. Preferably the hooks define respective cam surfaces which cooperate with the surface to cause the hooks to unhook from the rim. The hooks may be configured such that they are moved radially inwardly to unhook them from the rim.

In accordance with the invention in any of its aspects and embodiments, the injection device preferably comprises an end cap. The end cap covers the front or needle end of the device. In embodiments the end cap may be fitted to a front housing or the outer housing of the device at its front end. Preferably the end cap fits over the front housing of the device. This may further help maintain sterile conditions. The end cap is preferably configured to fit, e.g. clip, to the front end of the device. The end cap is typically removed prior to activation of the device. In preferred embodiments the device is configured such that it cannot be activated until the end cap is removed. The end cap may act as a further guard against accidental needle stick injuries or premature activation. In some sets of embodiments in which activation is carried out by urging the outer housing towards the front housing, the end cap is configured to prevent activation of the device by preventing relative movement of the front housing and outer housing.

In most embodiments the needle is protected by a needle guard which must be removed prior to use of the device. The needle guard may comprise an outer rigid needle guard and an inner resilient tip cap. The tip cap can be attached to the rigid needle guard to enable removal of the rigid needle guard and tip cap as a unit. The tip cap may be separately formed and attached to the rigid needle guard, or may be integrally formed therewith. For example, the tip cap may be a lining of the rigid needle guard. Preferably the needle guard is located between a front housing of the device and the needle. The needle guard and the tip cap of a syringe are typically supplied with the syringe, and are subject to regulatory approval. Thus, as with the syringe barrel and plunger, it is important that an injection device should be configured to operate with standard tip cap and needle guard arrangements, without needing to modify them, as this would require further regulatory approval to be sought.

In some preferred embodiments, the end cap is configured such that it pulls the needle guard from the needle as it is removed. This enables removal of the outer rigid needle guard and the inner tip cap as a unit with the end cap. In some sets of embodiments the needle guard is attached to the front housing of the device, and the end cap comprises means for pulling the needle guard from the front housing of the device as it is removed. In preferred embodiments the needle guard pulling means is configured to engage a rear end of the needle guard to remove it from the front housing. The needle guard pulling means may comprise hooks, claws or catches which extend between the front housing and the needle guard to remove the needle guard.

Preferably the end cap is configured such that it may be replaced after actuation of the device. This has been found to be beneficial to users who tend to feel more comfortable replacing the cap after use even if it may not be strictly necessary to avoid accidental needle stick injuries because the needle will be retracted after use in the preferred embodiments. In embodiments, the end cap is configured such that it may be fitted, e.g. clipped, onto the end of the device both before and after activation of the device. Preferably the device comprises first and second means respectively cooperating with the end cap to enable the end cap to be clipped on to the end of the device both before and after activation of the device, the first and second means being located in different axial positions. This stems from an appreciation that the relative position of the front housing and outer housing of the device will have changed during activation of the device.

This is novel and inventive in its own right and thus when viewed from a further aspect the invention provides an automatic injection device comprising an end cap, wherein the device comprises first and second means respectively for cooperating with the end cap to enable the end cap to be clipped on to the end of the device both before and after activation of the device, the first and second means being located in different axial positions.

The present invention in accordance with these further aspects may comprise any or all of the features described with respect to the other aspects of the invention.

In embodiments the front housing comprises first means which cooperate with the end cap to retain the end cap in place before activation of the device, and second means for cooperating with the end cap to retain the end cap in place after operation of the device. The first and second means may be axially spaced from one another, preferably by at least 2 mm, and in embodiments by a distance in the range of from 2 mm to 5 mm.

In accordance with the invention in any of its aspects and embodiments, the device is preferably packaged in an outer package for supply to a user. The invention extends to a package containing the injection device in accordance with the invention in any of its aspects or embodiments for supply to a user.

The invention in accordance with this further aspect may comprise any or all of the features described with respect to the other aspects of the invention.

In these aspects and embodiments of the invention, the outer packaging preferably comprises a container for the device, and a releasable seal closing the container. The seal may be an end seal. The container is preferably formed of a flexible material, and is preferably a blister pack. The packaging may be transparent. Preferably the packaging is of plastics. The packaging may comprise a film material. The packaging may comprise a polymeric material. Preferably the packaging is a single layer packaging.

In some preferred embodiments the packaging cooperates with the device physically to disable the activation mechanism of the device so that it cannot be operated even with a substantial force or impact such as might be encountered if a package is dropped or knocked in transit. Preferably the packaging cooperates with the device to block the release means of the mechanism. It is believed that these arrangements are advantageous in their own right.

In accordance with a further aspect of the invention there is provided a package comprising an outer packaging receiving a device therein, said device having a pre-loaded operating mechanism, wherein the outer packaging cooperates with the device to disable the mechanism by preventing movement of a release means of the mechanism.

The present invention in these further aspects and embodiments of the invention may include any or all of the features described with respect to the other aspects and embodiments of the invention.

These aspects and embodiments of the invention may provide a further safety feature should the internal arrangements of the device to try to prevent premature activation fail. These aspects and embodiments of the invention may be applied to a device having any kind of mechanism. Preferably the mechanism comprises driving means, and the package blocks a release means of the driving means. The driving means may, for example, be a spring or a compressed gas. In preferred embodiments, the mechanism is a spring loaded mechanism. In these embodiments the package may block a release means of the spring.

In these aspects and embodiments of the invention, the packaging may cooperate with the device to prevent activation of the device before the device is removed from the packaging. The packaging may, for example, be configured to prevent release of a catch or detent restraining the resilient force of the driving means. For example, in preferred embodiments, the packaging may prevent hooks of a retaining means unhooking from a rim to release the resilient force of the driving means. The packaging may comprise means for blocking movement of the hooks. The disabling means in these aspects and embodiments of the invention is an integral part of the packaging.

The present invention extends to a method of operating an injection device in accordance with any of the aspects or embodiments of the invention comprising the steps of placing the device against the skin and activating the device.

The injection devices in accordance with the present invention in any of its aspects and embodiments may be used in conjunction with any type of syringe. The devices may be used with conventional approved types of syringe, and do not require any modification of the syringe package, avoiding the need to seek additional regulatory approval.

It will be appreciated that the device of the present invention can be configured to be used with a standard syringe. Thus, in embodiments of the invention, the needle is fixed relative to the barrel of the syringe. The syringe as a whole i.e. including the barrel and needle is driven forward or retracted to advance or retract the needle. References to advancing/driving forward the needle may then equally refer to driving forward the syringe and vice versa. In embodiments the plunger acts on a piston of the syringe, wherein the piston is non compressible.

The device may be used to deliver liquids to subcutaneous, intradermal, subdermal or intramuscular levels, for example. The present invention is particularly advantageous for use with syringes having a glass barrel. Such syringes are more susceptible to breakage in use due to forces exerted to drive the plunger into the barrel.

The present invention extends to an injection device in accordance with any of the aspects or embodiments of the invention comprising a liquid to be dispensed in the syringe barrel. The injection devices may be used in accordance with syringes to inject a range of different liquids, ranging from viscous, e.g. sustained release, to non viscous liquids. The liquid may be any such liquid. The liquid may comprise a medicament. It is envisaged that the device may be advantageously used to dispense newer biological drugs which are becoming available.

In accordance with a further aspect of the invention, there is provided a kit of parts for the injection device of the invention in accordance with any of its aspects and embodiments. The kit may or may not be supplied with a syringe for mounting therein. In accordance with some embodiments, the syringe may be located in a syringe housing, and assembled with a front housing. A rear assembly comprising the remaining components of the device may then be assembled as a unit with the front part of the assembly. Thus in some embodiments, the device may be supplied as a two part kit which is assembled with a syringe.

It will be seen that the various aspects and embodiments of the invention provide an injection device which may provide greater control over injection depth and the quantity of dose delivered, as well as reduced risk of breakage to the syringe. The device may be more easily manufactured. Preferably the device is formed from injection moulding techniques. It has been found that in embodiments the whole device may be formed using two splits.

It will be appreciated that references to the "forward" direction herein refer to the direction towards the person to be injected in use, and the forward end of the injection device is therefore the needle end nearest to the person's skin in use. Conversely references to the "rearward" direction refer to the direction which is away from the person to be injected, while the "rear" of the device refers to the end of the device furthest from the person's skin in use.

To the extent that it may not be explicitly mentioned, any of the features described with reference to one of the aspects of the invention may be used in conjunction with any of the other aspects of the invention to the extent they are not mutually inconsistent.

BRIEF DESCRIPTION OF THE FIGURES

These and other features of the preferred embodiments of the invention will become more apparent in the detailed description in which reference is made to the appended drawings wherein:

FIG. 2 is a cut away view along the longitudinal axis of the device shown in FIG. 1;

FIG. 3 illustrates the syringe prepack of the device of FIG. 1 in more detail;

FIG. 4 is a perspective view illustrating the way in which the syringe prepack of FIG. 3 is encased in a syringe housing in the embodiment of FIGS. 1 and 2, but with other components of the device omitted for clarity;

FIG. 5 is a vertical cross sectional view through the assembly of FIG. 4, but also showing the front housing assembled thereto;

FIG. 6 shows the interior of the left portion of the syringe housing in more detail;

FIG. 7 illustrates the features of the exterior of the right portion of the syringe housing in more detail;

FIG. 8 illustrates the assembly of the syringe and syringe housing of FIG. 4 with return springs for coupling to the front housing;

FIG. 9 illustrates the assembly of FIG. 8 assembled with the front housing;

FIG. 10 is a further view of the assembly shown in FIG. 9 being cutaway at the front end;

FIG. 11a is a vertical cross sectional view through the front end of the device shown in FIG. 1 with the end cap in place;

FIG. 12 is a perspective view showing the syringe housing, drive cylinder, spring, plunger cup and guide cylinder of the assembly;

FIG. 13 is an exploded view showing the assembly of the front housing with the guide cylinder, drive cylinder and spring in more detail;

FIG. 14 illustrates the assembly of the syringe, syringe housing and drive cylinder, being cutaway in the front region;

FIG. 15 is a perspective view of the drive cylinder of the device of FIG. 1;

FIG. 16 is a vertical cross sectional view of the plunger cup of the device of FIG. 1;

FIG. 17 illustrates the engagement of the plunger cup with the plunger;

FIG. 18 is a perspective view illustrating the relative position of the plunger cup and the drive cylinder before actuation of the device of FIG. 1;

FIG. 19 is a perspective view illustrating the relative positions of the plunger cup and drive cylinder after actuation of the device of FIG. 1;

FIG. 20 is a perspective view showing the assembly of the front housing and guide cylinder in the device of FIG. 1, and the relative positions of the lugs of the plunger cup and drive cylinder in the slots in their initial position prior to activation of the device;

FIG. 21 is a cut away view corresponding to FIG. 20, but illustrating the position of the drive cylinder relative to the guide cylinder more clearly;

FIG. 22 is a detail vertical cross sectional view taken through the rear end of the device of FIG. 1 illustrating the way in which the spring force is retained before activation of the device;

FIGS. 23 to 28 illustrate the device of FIG. 1 at various stages before and after activation;

FIG. 23 is a cut away view showing the device of FIG. 1 disposed in an outer packaging;

FIG. 24 is a cut away view showing the device of FIG. 1 after removal of the end cap, and before activation;

FIG. 25 is a cut away view corresponding to FIG. 24, but including a vertical section through the front end of the device;

FIG. 26 is a cut away view showing the device of FIG. 1 after activation, and once the needle has been advanced to insert it into the skin but before dispensing commences;

FIG. 27 is a cut away view showing the device of FIG. 1 after activation, and once dispensing of liquid is complete, but before retraction of the needle;

FIG. 28 is a cut away view showing the device of FIG. 1 after activation, and once the needle has been retracted once more following dispensing of liquid.

FIG. 31 is an exploded perspective view illustrating the mechanism of the device of FIG. 30 in more detail, but with certain components omitted for ease of reference;

FIG. 31a is an end on view of the plunger driver in accordance with the second embodiment showing the opening 318 in more detail;

DETAILED DESCRIPTION OF THE INVENTION

The present invention may be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

As used in the specification and the appended claims, the singular forms "a," "an" and "the" include plural referents unless the context clearly dictates otherwise. Thus, for example, reference to a "leaflet" can include two or more such leaflets unless the context indicates otherwise.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Without the use of such exclusive terminology, the term "comprising" in the claims shall allow for the inclusion of any additional element—irrespective of whether a given number of elements are enumerated in the claim, or the addition of a feature could be regarded as transforming the nature of an element set forth in the claims. Except as specifically defined herein, all technical and scientific terms used herein are to be given as broad a commonly understood meaning as possible while maintaining claim validity.

Figure 1:
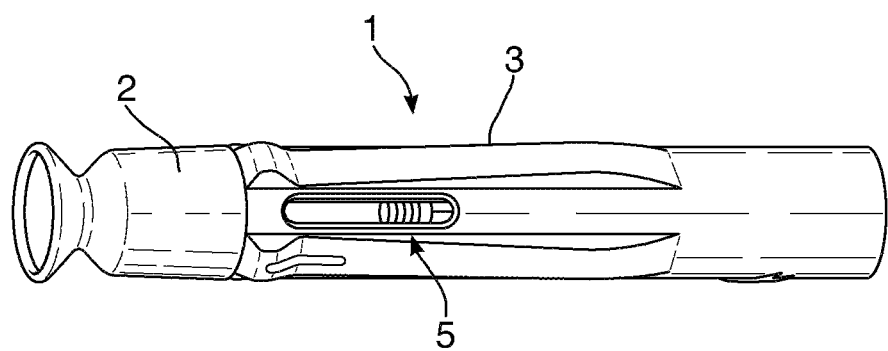
FIG. 1 is a perspective view showing a device in accordance with a first embodiment of the invention prior to use with the end cap in place and after removal of any outer packaging.

A first embodiment of the invention will be described with respect to FIGS. 1 to 29. FIG. 1 shows an automatic injection device in accordance with one embodiment of the invention. FIG. 1 shows the device after removal from any blister pack secondary packaging, and prior to use to administer an injection.

The device 1 has a rear end towards the right-hand side of the device in FIG. 1, and a front end towards the left-hand side of the device in FIG. 1. The device 1 includes an end cap 2 and a rear outer housing 3. The front end is the needle end of the device. In use, the end cap 2 is removed by a user to expose the front, needle end of the device. The rear outer housing 3 is gripped by the user during operation of the device to hold the front end against the skin. The rear housing 3 is provided with a tactile surface covering, and may includes ribs and other surface formations to facilitate gripping of the device, particularly if the device is intended for use with those with impaired manual dexterity. The end cap 2 is shaped to facilitate ease of gripping to enable a user to pull it away from the main rear section 2 of the outer housing prior to use even if they have difficulties in gripping objects.

The rear outer housing 3 includes a viewing window 5 through which the user may observe the position of the plunger before and after actuation of the device. In the view of FIG. 1, the plunger may be seen in its retracted position prior to use of the device to the right of the window. The user can compare the before and after positions of the plunger to check that the liquid in the barrel has been fully dispensed. To this end, the viewing window extends over the entire expected length of travel of the plunger in dispensing a full dose of liquid from the barrel.

FIG. 2 is a vertical cutaway view taken through the longitudinal axis of the device of FIG. 1 showing the internal mechanism of the device in its pre-activation state as supplied to the user, and after removal from any secondary packaging.

As may be seen with respect to FIG. 2, the device includes a syringe 7 disposed within a syringe housing 9, which is described in more detail below, and a front housing 11 which houses the needle of the syringe 7 when the end cap 2 is removed. The front housing 11 is the part of the device which is placed against the skin in use. During an injection cycle, the needle extends from the retracted position relative to the end of the front housing 11 as shown in FIG. 2 to an extended position to be inserted in the skin, before returning to a retracted position once more after delivery of the liquid.

The end cap 2 and outer housing 3 cooperate with one another such that the rear housing 3 may not be moved in the axial direction relative to the front housing 11 while the end cap 2 is in place. This may prevent premature activation of the device before the end cap 2 is removed.

The rear part of the device comprises a mechanism for automatically carrying out an injection cycle once activated in use, including the steps of; advancing the needle for insertion, depressing the plunger of the syringe for dispensing a dose of liquid from the barrel, and retracting the needle.

The mechanism includes a drive spring 13 which, once released, acts upon a drive cylinder 15 configured to selectively transmit a drive force to the plunger of the syringe via a plunger cup 17. The movement of the drive cylinder 15 and plunger cup 17 is guided by an outer guide cylinder 19 disposed between the drive cylinder 15 and the rear outer housing 3.

The components of the device will be described in more detail starting with the front portion of the device. The components of the front assembly are shown in more detail in FIGS. 3 to 11.

As shown in FIG. 3, the syringe 7 is a standard pre-filled syringe having a barrel 21, a needle 23 and a plunger 25 which acts on a piston 24. The syringe has a front shoulder 22. The barrel 21 is a glass barrel having a rear or "finger" flange 27. The finger or rear flange 27 is that part of the syringe against which a user would push during manual actuation of the syringe.

The needle is covered by a needle guard 29 which comprises a rigid outer needle shield 31 and an inner resilient rubber tip cap 33. The rigid needle shield 31 and the flexible tip cap 33 are attached to one another to enable them to be removed as a unit from the end of the needle. The rigid needle shield 31 may be a polyethylene shield.

Syringes of the type shown in FIG. 3 are subject to regulatory approval. Thus, in general most syringes conform to certain standard specifications. The syringe shown in FIG. 3 is, for example, a hipack BD staked needle with rubber tip cap and rigid needle shield which is one of the most commonly used syringe types. The standard syringe package of the type shown in FIG. 3 may be produced for dispensing different quantities of fluid. One of the most common devices is for dispensing a 1 ml dose of liquid. The embodiment shown is designed to cooperate with a standard syringe of the type shown in FIG. 3, or any other type of standard syringe to avoid the need to obtain further regulatory approval as would be required if the device required modification of the regulated parts of the syringe prepack in order to allow the device operate in conjunction with the prepack. Thus, the syringe prepack of the type shown in FIG. 3 is an example of a typical standard prepack which can simply be inserted into the device to enable automatic actuation. The plunger does not form part of the regulated pre-pack of the syringe. Thus, the plunger 25 may, if desired, be removed and replaced by a different plunger to actuate the piston 24 disposed in the barrel of the syringe without needing to seek reapproval of the modified pre-pack. The first embodiment of the invention does not require the use of a modified plunger, and a syringe pre-pack including the plunger as shown in FIG. 3 may be used directly in the device without modification, unless it is desired to replace the plunger for other reasons. However, in a further embodiment discussed below, in relation to FIG. 30 onwards, the plunger of the pre-pack is replaced with a modified plunger designed to interact with other components of the device to enable the mechanism to perform an automatic injection delivery cycle.

Figure 4:
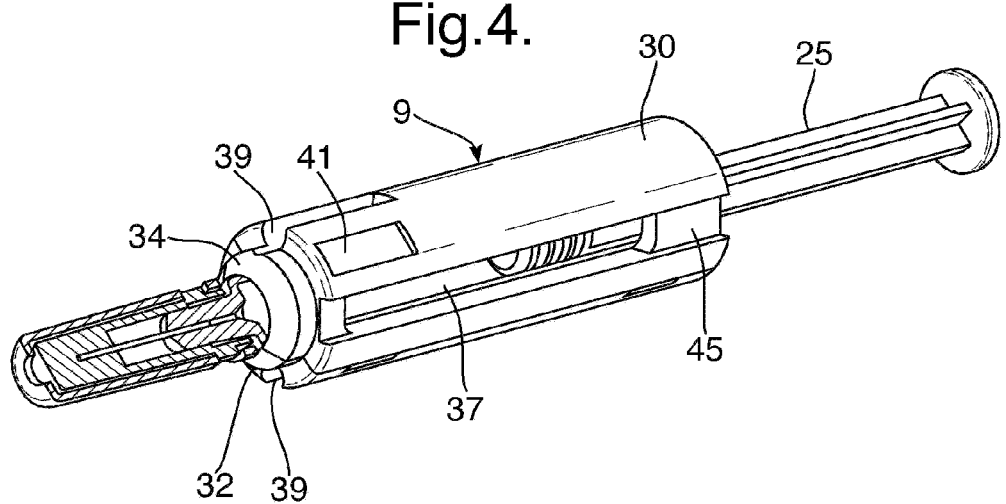
FIGS. 4 to 11 illustrate certain features of the front assembly of the device of FIG. 1 in more detail.
Figure 5:
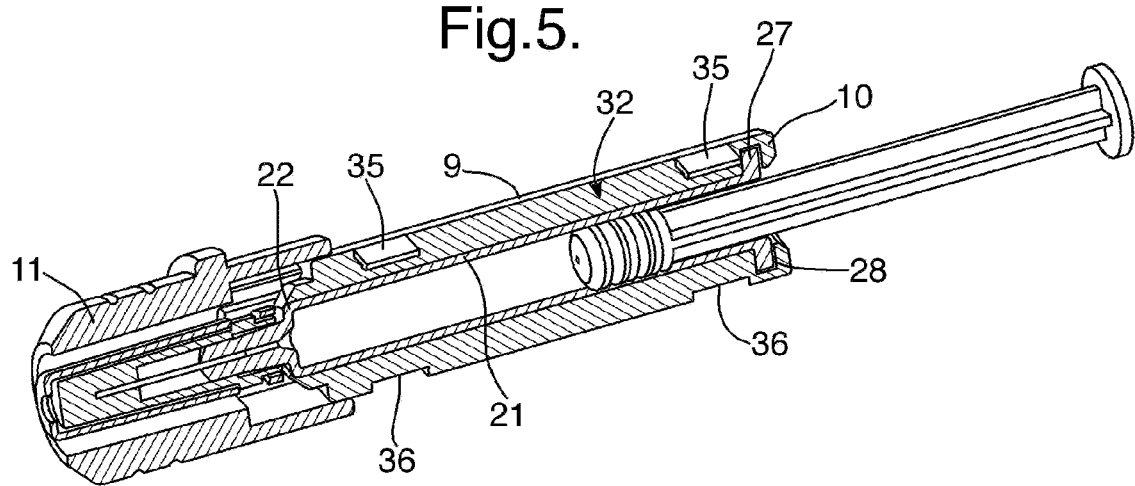
Figure 6:
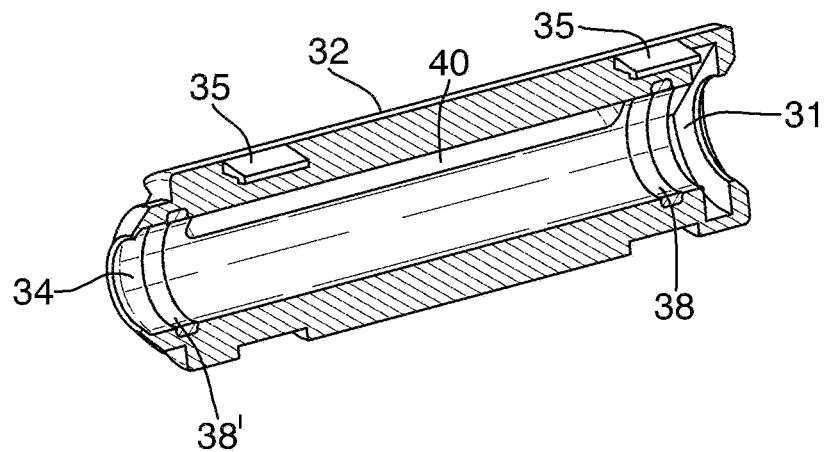
Figure 7:
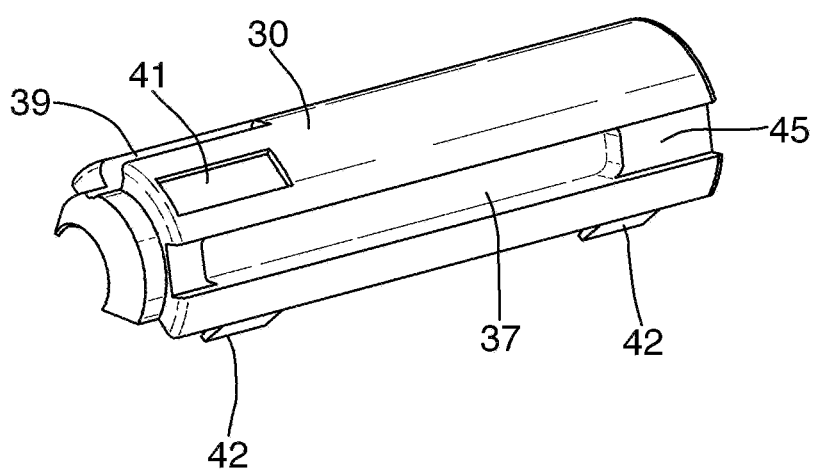
Figure 8:
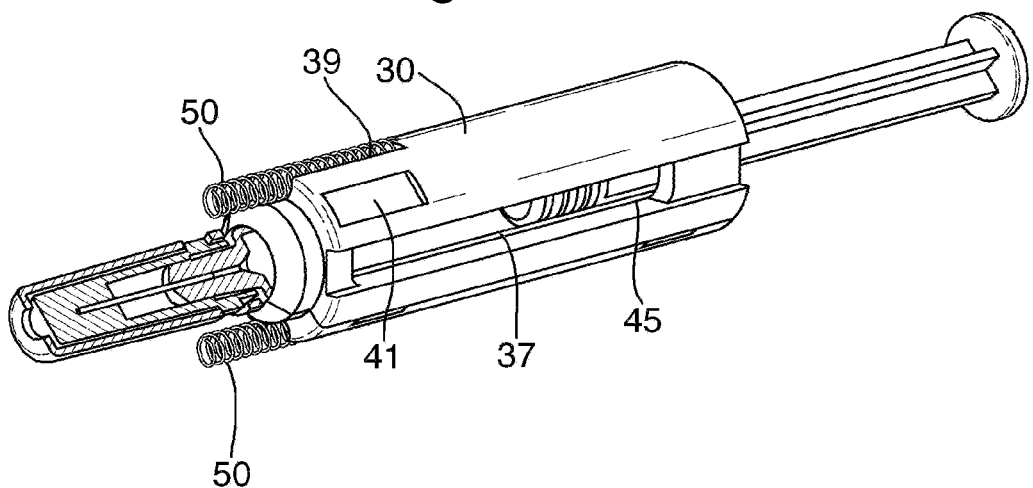
Figure 9:
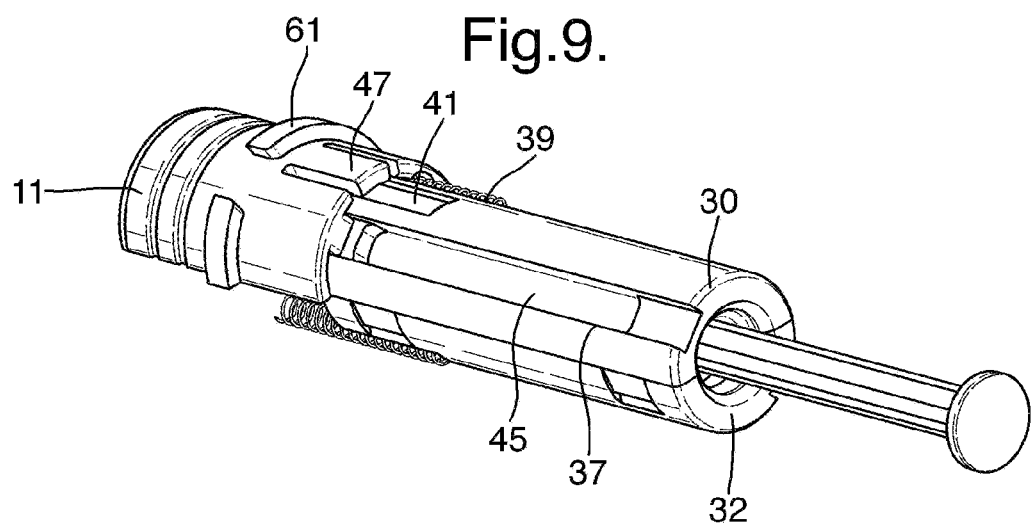

The syringe of FIG. 3 is encased in a syringe housing 9 which extends the entire length of the barrel 21. The syringe housing 9 is shown in more detail in FIGS. 4-10. FIG. 4 is a perspective view which illustrates the syringe housing 9 located over the syringe shown in FIG. 3. FIG. 5 is a vertical cross section along the longitudinal axis of the device showing the front housing, the syringe and left side of the syringe housing. FIG. 5 therefore illustrates the way in which the syringe housing engages the front housing 11. FIGS. 6 and 7 show the interior of the left half and the exterior of the right half of the syringe housing 9 respectively in more detail. FIG. 8 illustrates the insertion of return springs into bores in the syringe housing for coupling the syringe housing to the front housing 11, while FIG. 9 is a perspective view which illustrates the way in which the front housing 11 is coupled to the syringe housing 9 in more detail. Certain features of the front housing are shown in more detail in FIG. 10, which includes a vertical section through the front end of the device, showing the front housing, syringe and syringe housing, while FIG. 11 is a vertical cross sectional view through the front end of the device with the end cap in place over the front housing, showing how the front housing 11, end cap 2, and needle guard 29 cooperate with one another.

As may be seen more clearly with respect to FIGS. 4 and 5, at the front end, the syringe housing 9 engages the front shoulder 22 of the syringe, while the rear end 10 hooks over the rear flange 27 of the barrel 21. At the front end, the syringe housing 9 can slide into the front housing 11 as described in more detail below.

The syringe housing 9 is not movable relative to the syringe barrel, and therefore acts to immobilise the barrel in use. The barrel and needle will move as a unit with the syringe housing 9 in use. The syringe housing is formed from a rigid material e.g. polyethylene.

When the plunger 25 of a syringe is depressed in use, significant axial forces may normally be transferred to the barrel of the syringe. These may be transmitted from the plunger through the relative incompressible liquid disposed in the syringe barrel 21 to the body of the barrel, resulting in a significant risk of breakage, of the barrel, which is typically formed of a fragile glass material. Breakages are particularly common in the region of the rear flange 27 which is subject to some of the greatest levels of force in use, and may also be more susceptible to manufacturing flaws.

In embodiments, of the invention, the syringe housing 9 cooperates with the syringe barrel 21 to result in an arrangement in which no axial forces are applied to the rear flange 27 of the syringe barrel 9. This means that rather than applying axial forces which push against a fragile glass rear flange of the syringe as in conventional arrangements, in accordance with the present invention, the axial forces exerted through the plunger to depress it in use are applied to the rear end of the syringe housing 9 which may be of a plastic material, and designed to withstand such forces. The forces may be transferred to the main body of the barrel via the syringe housing without passing through the rear flange.

In embodiments of the invention, the syringe housing 9 encases the syringe barrel 21 including the rear flange 27, and immobilises the barrel. This enables the syringe housing 9 to distribute forces transmitted through the plunger in use more uniformly over the body of the syringe, and reduces the level of forces experienced by the barrel in use as the forces are shared by the housing. The syringe housing 9 provides a path via the rear portion 10 which enables axial forces to be transmitted to the body of the syringe via a path which bypasses the fragile rear flange 27 of the syringe.

The syringe housing 9 is defines two longitudinal sections 30,32, defining respectively a right half and a left half of the housing and which are joined together along their opposed longitudinal edges. The two sections may be seen, for example, in FIG. 9. The housing sections 30, 32 of similar construction resulting in a device which is symmetrical about the longitudinal axis. Thus, the interior of the right half 30 is of a similar construction to that of the half 32 shown in FIG. 6, and the exterior of the left half 32 is similar to the right half 30 shown in FIG. 7. The sections 30, 32 of the syringe housing may be formed via an injection moulding technique, and then the syringe may be located in place with respect to one of the sections, and the other closed around the syringe to securely immobilise it with respect to the housing 9.

In the embodiment illustrated, the syringe housing sections are configured to resiliently clip together. The cooperating clips 35 and clip retaining portions 36 of the left side of the housing may be seen in FIGS. 5 and 6. The clips 42 of the right hand side of the housing are visible in FIG. 7. In other embodiments not shown, the housing may alternatively formed from sections which are hingeably connected to one another by a living hinge to enable them to be located around a syringe. The sections may then clip together to close them around the syringe in the same manner as in the embodiments illustrated along their longitudinal edges. This enables the sections to be moulded together as a single piece in an injection moulding technique.

As shown in FIG. 6 with respect to the left housing half 32, the syringe housing includes a groove 31 at the rear end thereof for locating the rear flange 27 of the syringe barrel. At the front end, the housing includes a formation 34 for locating the front end of the syringe barrel 22.

The interior of the housing includes resilient gripping means. This may be seen in FIG. 6, which shows the resilient gripping means associated with the left half of the housing 32. The housing includes resilient gripping means in the form of resilient rubber O-ring 38 at the front end of the housing, and resilient rubber O-ring 38 at the rear end of the housing. The O-rings directly contact the main body of the barrel, and grip around the circumference of the syringe barrel. As may be seen in FIG. 5, a small air gap 28 is provided between the rear end of the rear flange 27 and the rear end 10 of the syringe housing. The gap 28 isolates the rear flange from forces in the plunger in use. A further circumferentially extending resilient rubber ring (not shown) may be disposed between the front end of the rear flange 27 and the syringe housing to protect the flange in use.

It will be appreciated that as the syringe housing 9 clamps around the syringe barrel 21, the syringe barrel is placed under compression rather than tension. As glass is stronger under compression than tension, this may further reduce the likelihood of breakage of the barrel in use.

The section 30 of the syringe housing 9 includes a viewing window 37 as may be seen in FIGS. 4, 7, 8 and 9. The viewing window 37 is designed to extend along the full expected length of travel of the end of the plunger 25 within the barrel between its initial position, and a final position after fully dispensing of the dose of liquid in the syringe barrel 21. The viewing window 37 cooperates with the viewing window 5 in the outer housing shown in FIG. 1. Further viewing windows may need to be included in any intermediate components which are not transparent to enable viewing of the plunger from the exterior of the device.

The syringe housing 9 includes blind ended slots 39 extending rearwardly from its front end in the axial direction for locating return springs 50 used in coupling the syringe housing to the front housing of the device as described in more detail below. The slot 39 of the right side 30 of the housing may be seen in FIGS. 7 and 10. The left hand housing section 32 includes a corresponding slot to provide a symmetric arrangement.

The right syringe housing 30 also includes a slot 45 which cooperates with a lug of the overlying drive cylinder 15, as described in more detail below. The slot 45 extends from the rear end of the housing in the region of the viewing window 37. The left hand syringe housing 32 includes a corresponding slot 45. The left hand syringe housing 32 may or may not include a viewing window 37.

The syringe housing 9 further comprises slots 41 for retaining the front housing 11 coupled thereto and limiting the relative axial movement of the front housing and syringe housing. The slots 41 associated with each half of the housing may be seen in FIGS. 9 and 10. Again, the arrangement is symmetrical with corresponding slots associated with each half of the housing.

The way in which the front housing 11 is coupled to the syringe housing 9 will now be described with respect to FIGS. 8-10. As shown in FIG. 8, return springs 50 are located in the guide slots 39 in each section of the housing. The springs 50 are mounted in the slots 39 with their rear ends abutting the rear ends of the respective slots 39. The front ends of the springs are mounted against the rear end of the front housing 11.

As seen in FIG. 9, the front housing 11 includes a rear claw 47 which is biased radially inwardly. The claw 47 cooperates with the retaining slot 41 in the right-hand section of the syringe housing as shown in FIG. 9 to permit limited relative axial movement possible between the syringe housing 9 and front housing 11. A similar arrangement is provided on the other side of the device, although this can not be seen in FIG. 9.

In this manner, the syringe housing may be moved between the retracted position as shown in FIG. 9, and an extended position in which the rear end of the claw engages the rear end of the retaining slot 41 with corresponding compression of the springs 50. The return springs 50 bias the syringe housing 9 towards the retracted position relative to the front housing, as shown in FIG. 9. In use, movement of the syringe housing 9 relative to the front housing 11 results in the syringe barrel and hence needle being retracted or advanced relative to the front housing 11 as the syringe is immobilised relative to the syringe housing 9, and therefore moves as a unit with the syringe housing.

The appropriate range of movement between the front housing and the syringe is dictated by the length of the slot 41 and the force and arrangement of the return springs 50, and may be chosen to provide the required level of movement for a given application.

Figure 10:
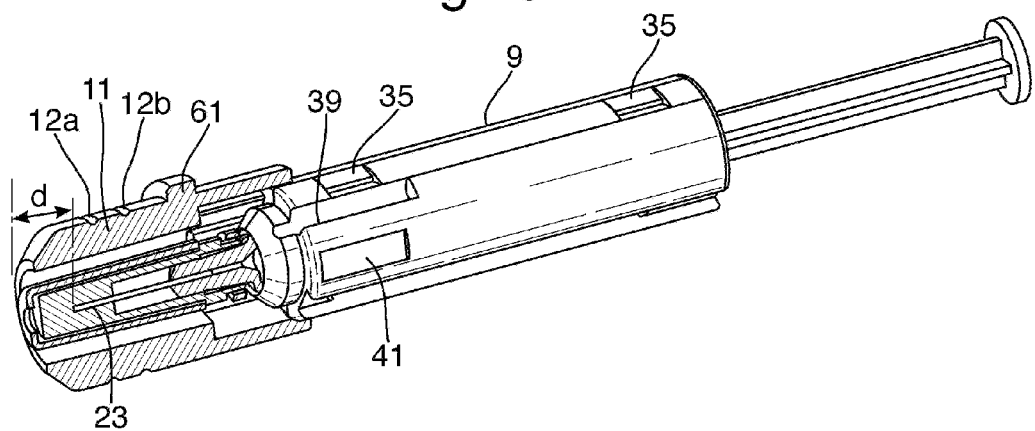
Figure 11:
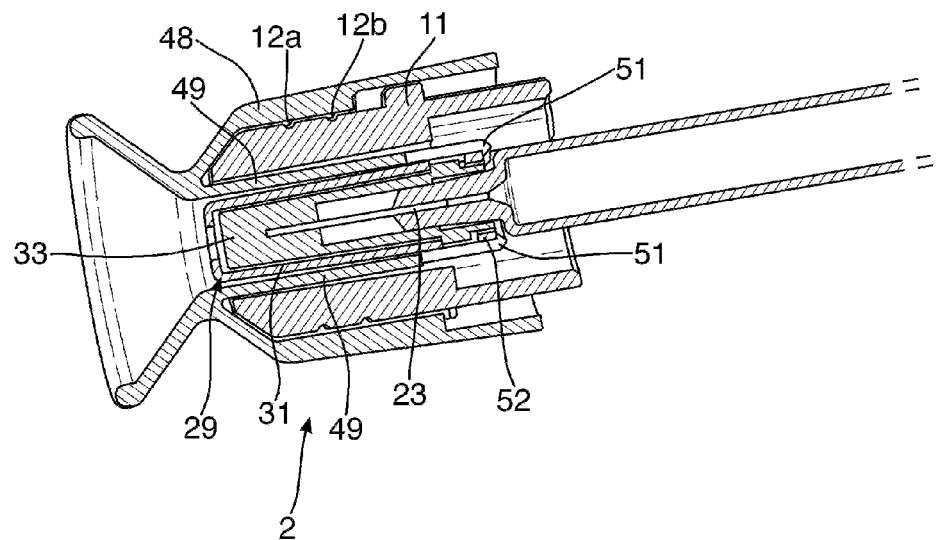

As shown in FIG. 10, when the syringe housing is in its retracted position relative to the front housing 11, the needle 23 is retracted by a distance d from the end of the front housing 11. This distance may be chosen as desired to ensure that the needle is retracted to a degree required to meet safety regulations with respect to needle stick injuries, and to provide security against accidental stabbing by the end of the needle before or after use of the device. It also necessary to take into account the force required to advance the needle from the retracted position to a desired insertion position for a particular syringe and/or liquid type. In some embodiments, the retracted distance of the needle d is 3 mm.

As the syringe housing 9 is moved forward to advance the needle 23 relative to the front housing 11, the needle 23 will protrude from the forward end of the front housing 11. The front housing 11 and syringe housing should cooperate to permit the needle to be advanced by the maximum amount anticipated, although the degree to which the needle is extended is also controlled by the mechanism of the device described below. For example in order to deliver a subcutaneous injection, it is typically necessary for the needle to extend 6 mm into the body of a user, and therefore to project 6 mm from the front end of the front housing 11. In these arrangements a total distance of travel of the needle may be chosen to be 9 mm. For an intramuscular injection the needle may extend by 9 mm into the body, and the total distance of travel of the needle may be 12 mm.

The way in which the end cap 2 cooperates with the front housing 11 and the needle guard 29 of the syringe is described in more detail with reference to FIG. 11.

The end cap 2 comprises an outer shroud 48 which fits loosely over the front housing 11 and an inner cylindrical portion 49 which extends into the bore of the front housing 11 so as to pass between the front housing 11 and the needle guard 29. The front housing has two axially spaced annular grooves 12a, 12b. Although not shown in the Figures, the inner surface of the outer shroud 48 has a lug which clips into the rearmost of these grooves 12b.

The inner portion 49 comprises rear claws 51 which grip behind a rear end 52 of the needle guard 29. In this way, when the end cap 2 is pulled away from the rear outer housing 3 by a user (unclipping the lug from the groove 12b on the front housing 11), it will also remove the needle guard 29. As the rigid needle shield 31 and flexible tip cap 33 of the needle guard are joined to one another, they may be pulled off with the end cap 2 as a single unit. By pulling the needle guard off from its rear in this manner, it has been found that the device is less subject to failure, particularly if the device is stored for some time before use. In use, when assembling the overall device, the components of the device described with respect to FIGS. 3 to 11 may be assembled together as a front assembly prior to attachment of the rear assembly described below.

The syringe may first be located in the syringe housing 9 to obtain the arrangement as shown in FIG. 4, and may then be combined with the front housing 11 as described with respect to FIGS. 5, 8, 9 and 10. Finally, the end cap 2 may be located over the front of the front housing 11 to obtain the arrangement shown in FIG. 11.

The rear part of the device will now be described.

Figure 12:
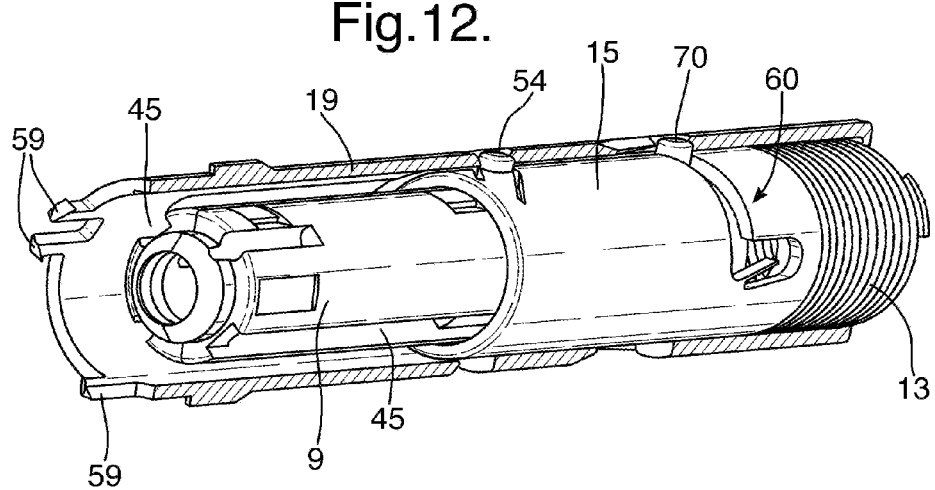
FIGS. 12 to 22 illustrate certain features of the rear assembly of the device of FIGS. 1 and 2 in more detail.
Figure 13:
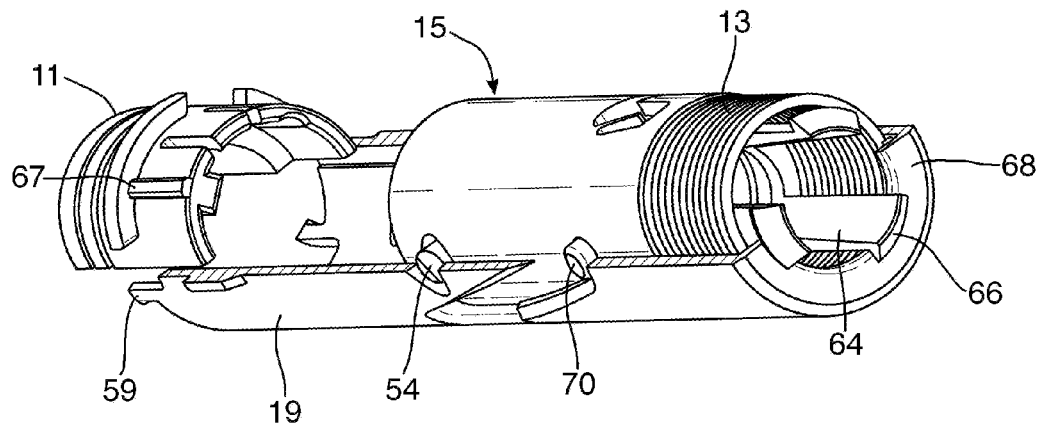
Figure 14:
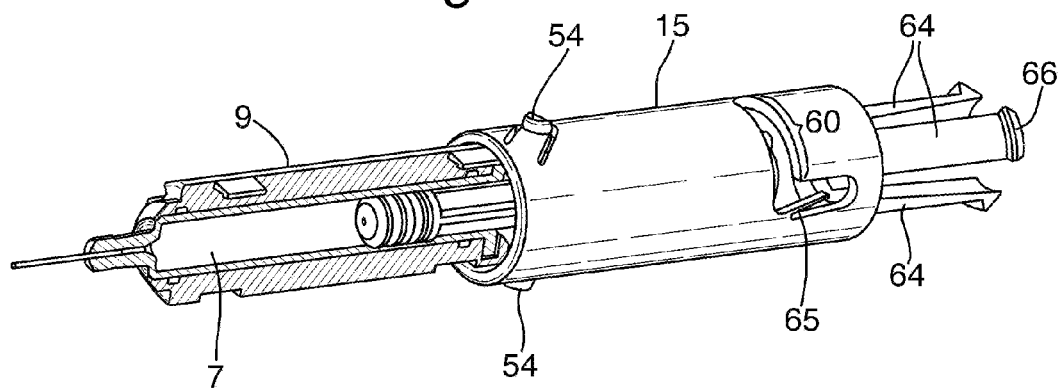

FIGS. 12 to 14 illustrate the way in which the components of the rear assembly are combined with one another in more detail. FIG. 12 illustrates the rear part of the assembly shown in FIG. 2. The front housing 11, rear outer housing 3, end cap 2 and syringe 7 are omitted for clarity. FIG. 13 is an exploded view showing the attachment of the front housing 11 to the guide cylinder 19 and drive cylinder 15, omitting the plunger cup 17, syringe 7 and syringe housing 9. Finally, FIG. 14 is a view showing the syringe 7 disposed in the syringe housing 9, and illustrating its relationship with the drive cylinder 15. The drive cylinder 15, guide cylinder 19, front housing 11, plunger cup 17, drive spring 13 and end cap 2 are not shown in FIG. 14.

As may be seen in FIGS. 12 to 14, the drive cylinder 15 is located over the rear end of the syringe housing 9. The syringe housing 9 and the drive cylinder 15 are retained together by means of a pair of radially inwardly projecting lugs 52 provided on diametrically opposite sides of the drive cylinder 15 (not shown in FIGS. 12 to 14, but shown in FIG. 15) which abut the rear end of the syringe housing 9 preventing relative axial movement between the syringe housing 9 and the drive cylinder 15 when the device is in its pre activation state as shown in FIGS. 1 and 2. As described in more detail below, when the drive cylinder rotates relative to the syringe housing 9 in use, the lugs 52 rotate into the axially extending slots 45 of the syringe housing 9 to permit relative axial movement between the syringe housing 9 and the drive cylinder 15.

It will be appreciated that the construction of the drive cylinder and guide cylinder is symmetric about a longitudinal axis, as with the syringe housing. Thus, although not necessarily visible in the sections shown, each side of the guide cylinder and drive cylinder will include identical slots, and, in the case of the drive cylinder, lugs.

As shown in FIG. 12, the front end of the drive cylinder 15 also includes an outwardly projecting lug 54 in the region of the inwardly projecting lug 52. A corresponding lug is found on the opposite diametrical side of the cylinder. This may be seen for example in FIG. 15. The lugs 54 cooperate with the guide cylinder 19 to guide relative movement of the guide cylinder 19 and drive cylinder 15 as described in more detail below.

Figure 20:
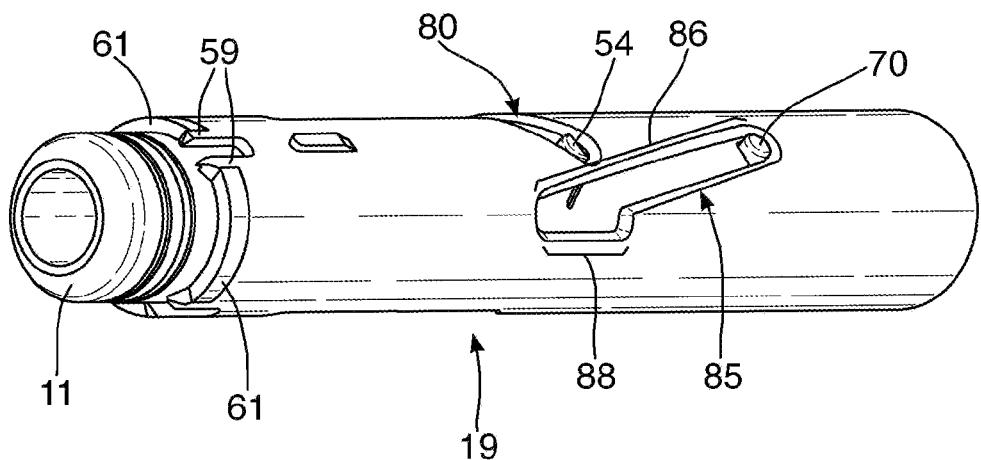
Figure 21:
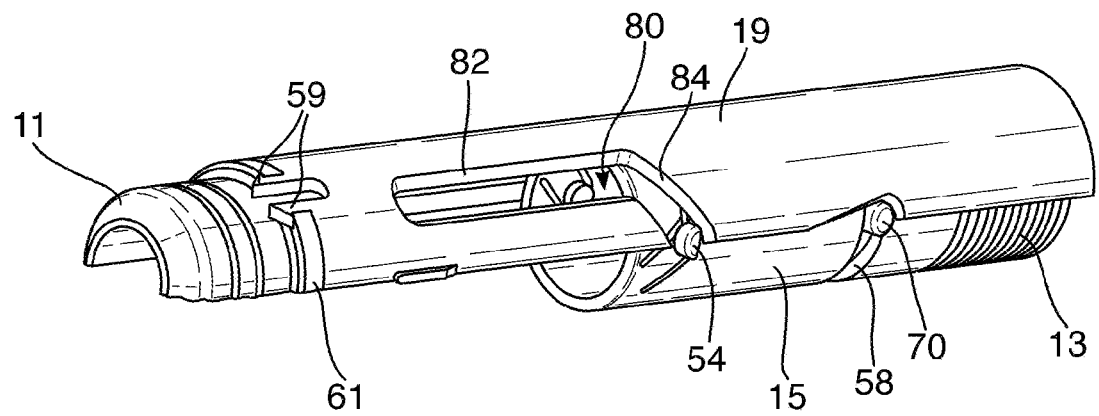

The guide cylinder 19 fits over the drive cylinder 15 and is mounted at its front end to the front housing 11 in a manner which does not permit relative movement between the guide cylinder 19 and the front housing 11. In the illustrated embodiment, this is achieved by clipping the front end of the guide cylinder 19 onto the front housing 11 using opposite pairs of resilient legs 59 which clip into respective circumferential gaps in an annular collar 61 around the front housing 11. The legs 59 may be seen in FIG. 12 and the assembled relationship is shown in FIGS. 20 and 21.

In use, when the spring 13 is released, it is operable to exert a force to drive the drive cylinder 15 axially over the syringe housing 9 in a direction to the left as shown in the Figures. As shown in FIG. 13, the front housing includes axially extending ribs 67 to act as assembly locators, and ensure the correct orientation of the guide cylinder 19 relative to the front housing 11 and syringe housing 9.

The connection of the guide cylinder 19 to the front housing 11, and the way in which it cooperates with the drive cylinder 15 and plunger cup 17 may be seen more clearly with reference to FIGS. 19-22. The rear end of the drive cylinder 15 includes a plurality of resilient legs 64 over which the driving coil spring 13 is mounted. In the pre-activation state of the device shown in FIGS. 1 and 2, hooks 66 at the rear end of each leg 64 hook over a rim 68 surrounding an aperture in the rear end of the guide cylinder 19 to retain the spring in the compressed position shown. The hooks 66 define ramped upper surfaces for reasons to be discussed below.

Figure 15:
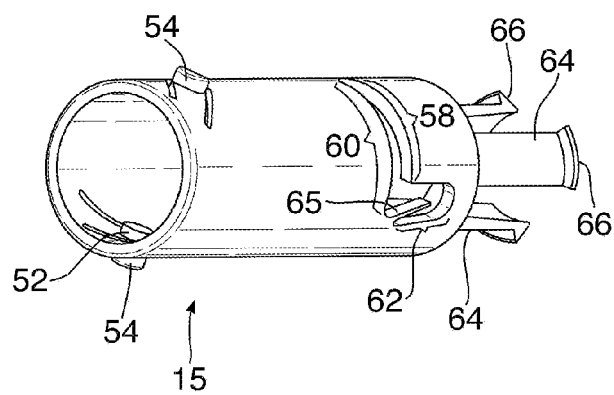
Figure 16:
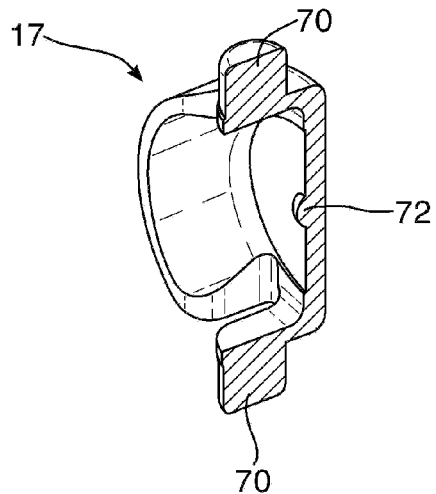
Figure 17:
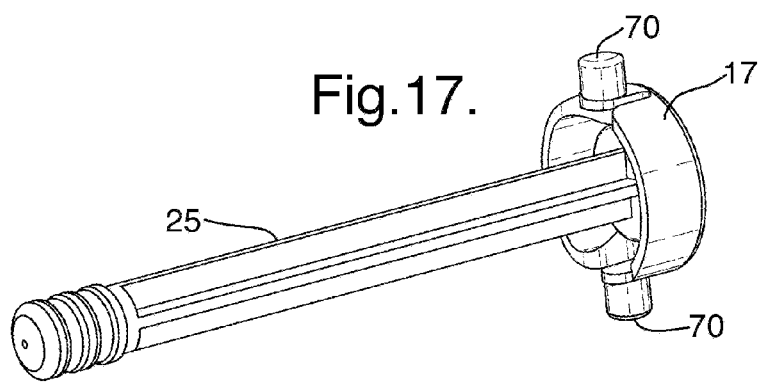
Figure 17A:
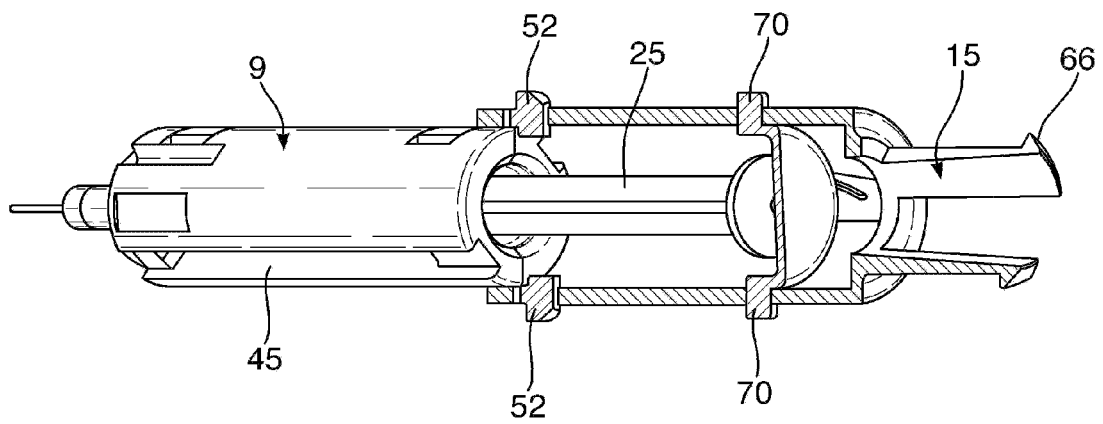
FIG. 17A illustrates the assembly of the plunger cup, drive cylinder and syringe housing in more detail.
Figure 18:
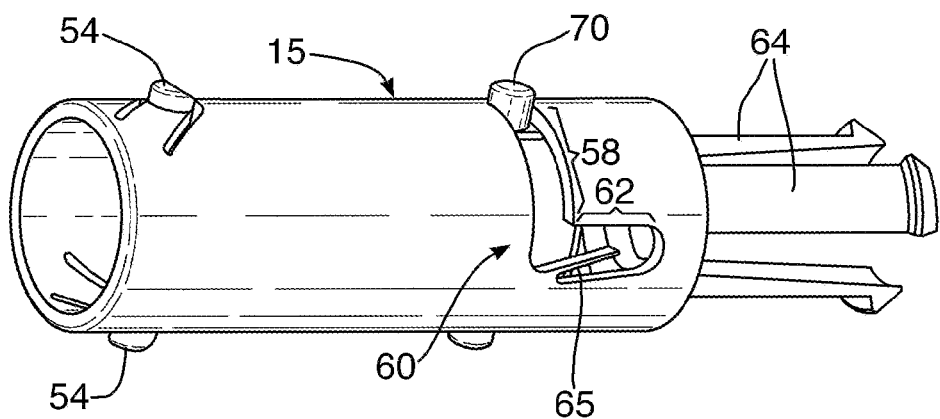
Figure 19:
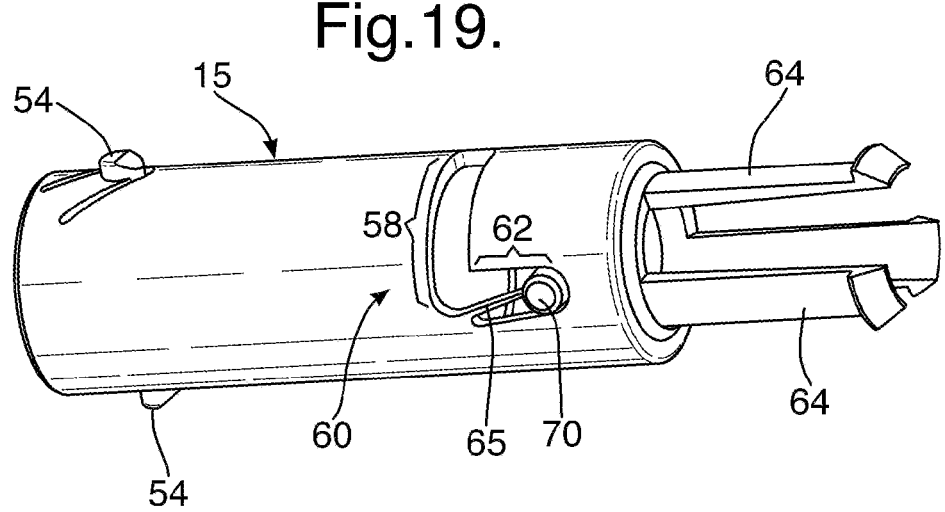

The construction of certain components of the rear assembly will be described in more detail with respect to FIGS. 15 to 22. FIG. 15 illustrates the guide cylinder 15 in more detail, while FIG. 16 is a vertical section through the plunger cup 17. FIG. 17 illustrates the plunger cup 17 fitted over the end of the plunger 25, and FIG. 17A illustrates the way in which the end of syringe housing 9 cooperates with the lugs 52 of the drive cylinder 15. FIGS. 18 and 19 illustrate the way in which the plunger cup 17 and drive cylinder 15 cooperate with one another. FIGS. 20 and 21 illustrate the connection between the front housing 11 and the guide cylinder 19, and the way in which the guide cylinder 19 may guide movement the plunger cup 17 and drive cylinder 15 in use.

With reference to FIG. 15, the drive cylinder 15 includes an L-shaped slot 60 towards its rear end. The slot 60 includes a first portion 58 which extends only in the circumferential direction, and a rearwardly extending back leg 62, which extends only in the axial direction. The rear leg 62 includes a hook 65 for purposes to be described below.

The plunger cup 17 is located within the drive cylinder 19, and engages the end of the plunger. The plunger cup 17 comprises a pair of outwardly projecting lugs 70 on each diametrical side, one of which rides in the L-shaped slot 60 of the drive cylinder 15. A corresponding L-shaped slot 60 is present on the other side of the cylinder (not visible in FIG. 15) for guiding the other lug 70 of the plunger cup. The slot also includes a hook. FIGS. 12, 17 and 18 show the plunger cup 17 in place within the drive cylinder 15, while it is omitted from FIGS. 13, 14 and 15 for ease of reference.

As FIG. 16 shows, the plunger cup 17 defines an inwardly projecting pip 72 on its plunger facing surface to facilitate rotation of the plunger cup 17 relative to the end of the plunger 25, and decrease the frictional forces opposing rotational movement of the plunger cup 17 relative to the plunger 25. As shown in FIG. 17 the plunger cup is fitted over the rear end of the plunger 25.

The movement of the plunger cup will be described with reference to the movement of the lug 70 in the slot 60 visible in the Figures. It will be appreciated that the other lug 70 on the other side of the plunger cup will similarly ride in a correspondingly shaped slot 60 on the other side of the device. When the device is in the pre-activated state of FIGS. 1 and 2, the lug 70 of the plunger cup 17 is disposed at the start of the circumferential portion 58 of the slot 60 in the drive cylinder 15 in the position shown in FIG. 18. The plunger cup 17 is therefore rotatably coupled to the drive cylinder 15 by means of the lug 70 riding in the circumferential portion 58 of the slot 60. In use, the plunger cup 17 is rotatable relative to the drive cylinder 15 until the lug 70 is able to reach the start of the rearward linear leg 62 of the slot 60. The plunger cup 19 may then move rearwardly relative to the drive cylinder 15 until the lug 70 is retained by the hook 64. FIG. 19 shows the drive cylinder 15 and the plunger cup 17 at the point in which the lug 70 of the plunger cup 17 has moved rearwardly through the leg 62 of the slot 60 and is retained in a retracted position by the hook 65 In exemplary embodiments, the circumferential portion 58 of the slot 60 extends a distance such that the plunger cup rotates by 90° relative to the drive cylinder 15 when moving from its initial position to reach the linear portion 62 of the slot.

It will be appreciated that when the lug 70 of the plunger cup 17 enters the rear leg 62 of the drive cylinder slot 60, the plunger cup 17 may move linearly relative to the drive cylinder 15 in the rearward direction. However, once it has passed over the resilient hook 65, it may no longer move forward in the linear direction relative to the drive cylinder 19 in the slot 62 beyond the hook 65. The hook 65 therefore retains the plunger cup 17 in a retracted position relative to the drive cylinder 15.

As shown with particular reference to FIGS. 20 and 21, the outwardly directed lug 54 at the front end of the drive cylinder 15 rides in a first slot 80 in the guide cylinder 19. As shown in FIG. 21, the slot 80 includes a front portion 82 which extends only linearly in the axial direction, and a rear portion 84, which is inclined relative to the front portion 82, extending in a direction having both linear and circumferential components. When the device is in the pre-activation state of FIG. 1, the lug 54 is disposed at the rear end of the slot as shown in FIGS. 20 and 21. In exemplary embodiments, the rear portion 84 extends at about 45° to the front portion 82. The inclined portion 84 is designed such that the linear distance travelled by the drive cylinder 15 with the lug 54 travelling in the inclined portion 84 corresponds to the total distance required to drive the syringe and needle forward to extend from the front housing 11 and enter the skin of a user to a required dispensing depth.

In use, when the drive cylinder 15 moves axially under the action of the spring 13 to the left of FIGS. 20 and 21, the lug 54 moves through the inclined portion 84 of the slot 80 in the guide cylinder 19. The lug 54 on the other side of the drive cylinder 15 similarly moves in a respective slot 80 of the same construction. The arrangement will be described with respect to the movement of the lug 54 visible in the Figures, but the other lug will move similarly in its slot. As the guide cylinder 19 is attached in a fixed position to the front housing 11, this causes the drive cylinder 15 to rotate relative to the guide cylinder 19 and front housing 11. The drive cylinder therefore also rotates relative to the syringe housing 9. Over this first part of the movement of the drive cylinder 15 relative to the syringe housing 9, the drive cylinder 15 engages the end of the syringe housing 9 and may not move axially relative thereto, thereby causing the syringe housing 9 to advance axially relative to the front housing 11 with the drive cylinder 15. This is shown in FIG. 17 A. Once the lug 54 of the drive cylinder 15 reaches the linear portion 82 of the slot, the drive cylinder 15 has rotated such that the inner lugs 52 are in alignment with the guide slot 45 of the syringe housing 9. Thus, at this point, the drive cylinder may start to move axially relative to the syringe housing 9 with the lug 54 riding in the linear portion 82 of the slot 80 of the guide cylinder 19, and the lugs 52 disposed in the guide slot 45 of the syringe housing 9. In this further part of the movement of the drive cylinder 15 relative to the syringe housing 9, the drive cylinder 15 may move only axially with respect to the syringe housing 9.

The guide cylinder 19 also includes a second slot 85 at its rear end having a rear helical portion 86 and a linear front portion 88. The lug 70 of the plunger cup 17 is guided by this slot. Another slot 85 is present on the other side of the guide cylinder 19 for guiding the other lug 70 of the plunger cup, and is of the same construction as the slot 85 shown in the drawings. The movement of the plunger cup will be described with reference to movement of the lug 70 in the second slot 85 visible in the drawings. However the other lug 70 will similarly ride in its own slot at the same time. When the device is in its pre-activation state as shown in FIGS. 1 and 2, the lug 70 is disposed at the rear end of the helical portion 86 of the slot as shown in FIGS. 20 and 21. In this way, during a first part of the motion of the drive cylinder 15 axially under the action of the spring 13 in use, the plunger cup 17 is rotatably coupled to the drive cylinder 15 by the engagement of the lug 70 with the slot 60, and will be caused to rotate in the opposite sense to the drive cylinder 19 by virtue of the engagement of the lug 70 with the helical portion 86 of the slot 85. This causes the plunger cup 17 to rotate relative to the drive cylinder 15, with the lug 70 travelling through the circumferential portion 58 of the slot 60. The helical portion 86 of the slot 85 has a length such that when the drive cylinder 15 is no longer rotating, but is free to move linearly relative to the syringe housing 9 with the lug 54 riding in the linear portion 82 of the slot 80, the lug 70 of the plunger cup 17 will continue to ride in the helical portion 86 of the slot 85, such that it will continue to rotate relative to the drive cylinder 15. The plunger cup 17 will continue to rotate until the lug 70 has reached the bottom end of the slot 85. The lug 70 may then move rearwardly into the linear portion 88 of the slot, allowing the plunger cup 17 to decouple from the drive cylinder 15, and retract and move axially through the rear leg 62 of the slot 60 in the drive cylinder 15 relative to the drive cylinder 15.

It will be seen that in use, when the spring force is released, the spring 13 will urge the drive cylinder 15 axially in the forward direction towards the front housing 11. While the plunger cup 17 rides in the circumferentially extending portion of the slot 60, it will be rotatably coupled to the drive cylinder 15, and will move axially therewith to transmit the driving force to the plunger 25. As the inwardly directed lugs 52 of the drive cylinder 15 engage the rear end of the syringe housing 9 in the initial rotational position of the drive cylinder 15 relative to the syringe housing 9, the initial forward axial movement of the drive cylinder 15 under the action of the coil spring 13 will drive the syringe housing and hence the syringe and needle forwards to extend the needle relative to the front housing for insertion into a body. The engagement of the lugs 52 with the end of the syringe housing 9 during this stage in the operation of the device is shown in FIG. 17A. The force transmitted from the drive cylinder 15 to the plunger cup 17 is not effective in causing the plunger cup to advance the plunger relative to the barrel. Once the drive cylinder 15 has rotated to enable it to move axially relative to the syringe housing 9, it may travel further forward in the axial direction relative to the barrel of the syringe and the syringe housing 9. The plunger cup 17 is coupled to the drive cylinder 15 thereby causing the plunger to be forced into the barrel to dispense liquid. This may continue until the plunger cup 17 has rotated relative to the drive cylinder 15 to the extent necessary for the lug 70 to reach the linear portion of the slot 60 and the corresponding linear portion 88 of the guide cylinder slot 85, enabling the plunger cup 17 to move linearly relative to the drive cylinder 15 thereby decoupling therefrom.

In this way, the drive timer 15 and plunger cup 17 cooperate so that a drive force applied to the drive cylinder is selectively transmitted to the plunger, depending upon whether the plunger cup 17 is coupled to the drive cylinder 15, i.e. when its lugs 70 ride in the circumferentially extending portion 58 of the slot 60, or whether it is decoupled therefrom, and able to move linearly relative thereto in the axial direction, by virtue of the lug 70 riding in the linear portion 62 of the slot 60.

Figure 22:
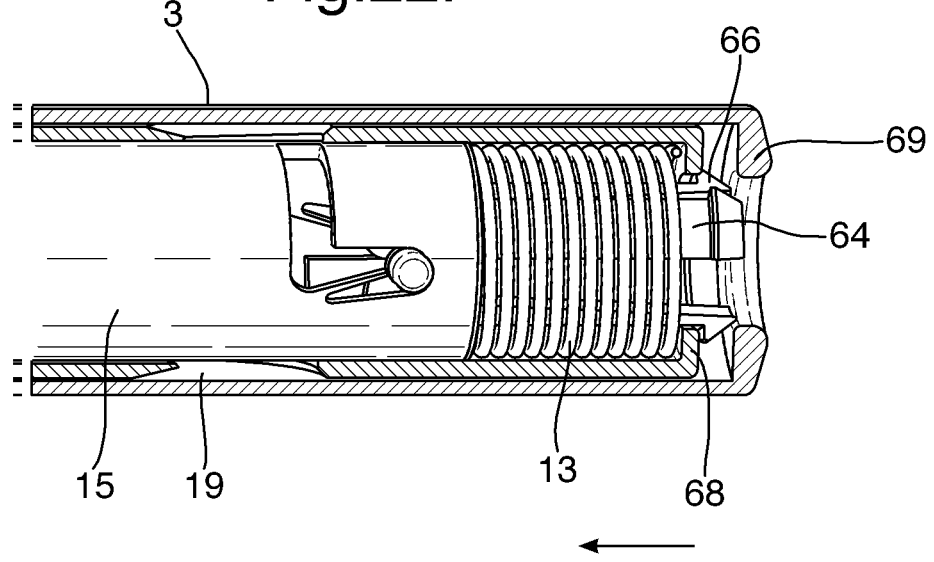

Prior to use, it is necessary to activate the device 1 to release the spring force. The device is configured such that relative axial movement of the rear housing 3 and the front housing 11 results in activation of the device by releasing the spring force. The way in which this is achieved is shown in the view of FIG. 22. In its pre-activated state, as described above, the hooks 66 at the rear end of the resilient legs 64 which mount the spring 13 to the drive cylinder 15 hook over a rim 68 surrounding an aperture at the rear end of the guide cylinder 19. The legs 64 are biased radially outwardly. When the rear end 69 of the rear housing is moved in the direction of the arrow in FIG. 22 relative to the guide cylinder 19, the end 69 engages the ramped cam surfaces at the top of the hooks 66, urging the legs 64 radially inwardly. This enables the hooks 66 to unhook from the rim 68 and pass through the opening at the end of the guide cylinder 68 thereby releasing the force of the spring 13. The spring will then exert a driving force causing the drive cylinder 15 to travel axially forwardly to the left of FIG. 22. The ramp angle of the inclined surface at the top of each hook 66 may be selected as appropriate to set the force with which the end 69 of the outer housing 3 must engage the hooks 66 to cause them to move inwardly sufficiently to disengage from the ends of the guide cylinder, enabling the spring to be released. In some exemplary embodiments, the distance that the outer housing 3 must move axially in order for the end 69 of the outer housing to engage the tapered lugs 66 is around 45 mm. In exemplary embodiments, the spring 13 will have been released before the outer housing makes contact with the end of the guide cylinder 19.

Figure 23:
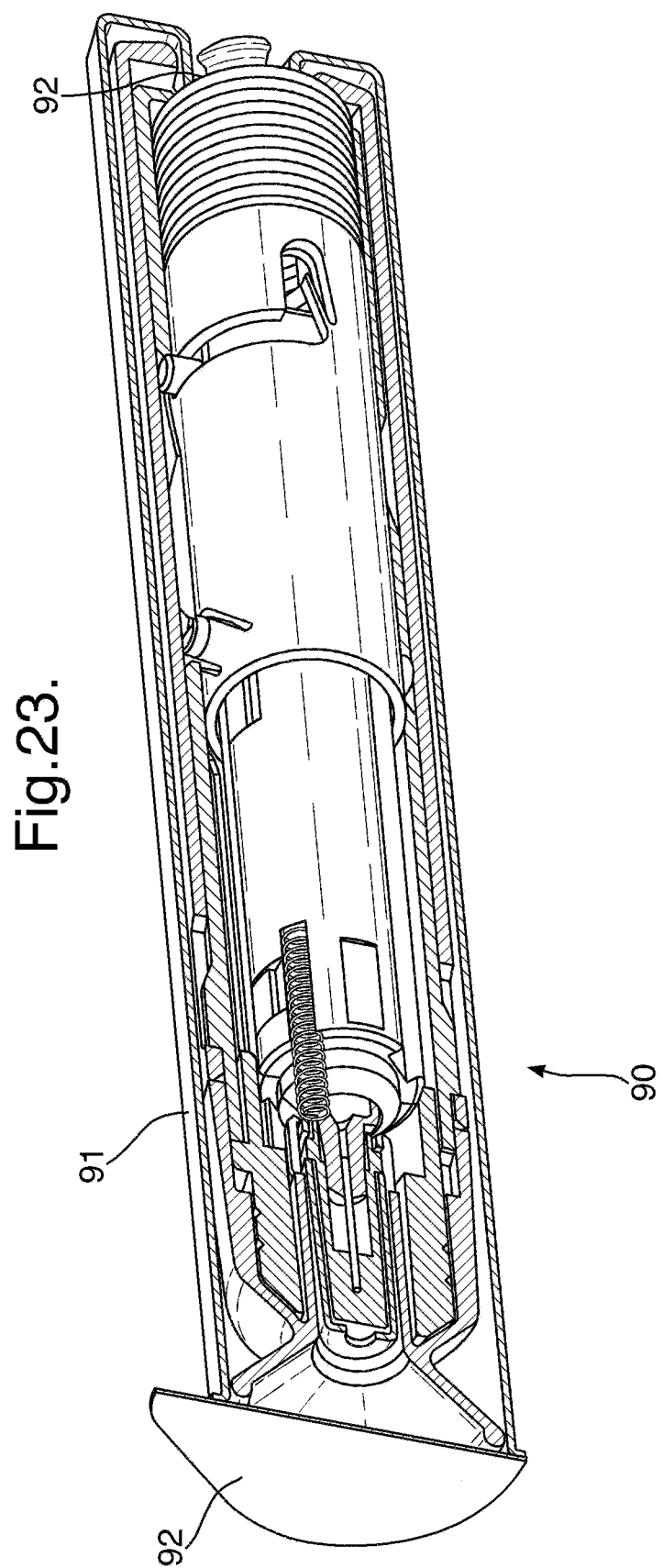

FIG. 23 illustrates the device 1 of FIG. 1 before activation when it is disposed in a disposable secondary packaging 90. The secondary packaging 90 is in the form of a blister pack defining a container for the device 1, and having a main body 91 sealed by an end tab 92 which may be removed from the main body 91 to allow removal of the device from the packaging 90. The blister pack defines a detent 92 at its rear end which extends axially into the aperture at the centre of the rim 68 in the outer housing 3 to engage between the resilient legs 64 at the rear of the drive cylinder 15. The outer packaging 90 therefore cooperates via the detent 92 with the mechanism of the device to prevent the spring force being released prematurely before the device is removed from the packaging, by preventing the inward movement of the legs 64 required to release the spring 13. The packaging also maintains a sterility of the pack, although sterility is already provided by the conventional needle shield of the syringe shown in FIG. 3.

Operation of the first embodiment of the invention will now be described with respect to FIGS. 23 to 28.

First the user removes the device shown in FIG. 23 from the secondary blister pack by ripping off the end seal 92 and removing the device from the container 90. The resulting device is as shown in FIGS. 1 and 2. The device 1 still cannot be actuated until the user removes the end cap 2 as the rear outer housing 3 may not be moved forward axially relative to the front housing 11 to disengage the hooks 66 retaining the resilient force of the spring 13. The user next removes the end cap 2, which pulls with it the attached needle guard 29, including the rigid needle shield 31 and inner tip cap 33. This results in a device as shown in FIG. 24. FIG. 25 is a cut away view of the device shown in FIG. 24 illustrating the position of the needle retracted relative to the front end in more detail.

The user then places the front end of the front housing 11 against the skin. At this point the needle is in the retracted position shown in FIG. 25 relative to the front end of the front housing. In exemplary embodiments, the needle is retracted by a distance I=3 mm from the end of the housing to protect against accidental needle stab injuries.

The user then pushes down against the front housing 11 in the axial direction while gripping the rear part of the outer housing 3. This causes the outer housing 3 to move in an axial direction relative to the front housing 11 from the position shown in FIG. 22 such that rear end 69 of the outer housing 3 engages the ramped upper surface of the hooks 66 at the rear end of the resilient legs 64 retaining the drive cylinder 15 hooked over the rim 68 at the rear end of the guide cylinder 19. The resilient legs 64 are urged radially inwardly under the action of the outer housing until they are unhooked from the rim 68 and start to pass through the opening at the rear end of the guide cylinder 68. At this point the force of the spring 13 is released and pulls the hooks 66 the rest of the way through the aperture in the guide cylinder 19, and starts to drive the drive cylinder forwards axially in the forward direction to the left of FIGS. 24 and 25.

Once the drive cylinder 15 starts to move forwards axially under the action of the drive spring 13, it initially cannot move axially relative to the syringe housing as a result of the engagement of the inner lugs 52 with the rear end of the syringe housing 9. Thus, it acts to drive forward the syringe body and hence the needle relative to the front housing 11 towards the exposed position shown in FIG. 26. As the drive cylinder moves forward relative to the front housing 11 against the bias of the return springs 50, the return springs 50 are compressed. As the drive cylinder 15 moves forward axially it is forced to rotate through 45° as a result of the engagement of the lugs 54 with the inclined portions 84 of the slots 80 in the guide cylinder 19. While the drive cylinder 15 moves forward axially and rotates with the lugs 54 riding in the inclined portions 84 of the slots 80, the plunger cup 17 will rotate in the opposite direction with the lugs 70 riding in the circumferential portions 58 of the drive cylinder slots 60, as the lugs 70 move through the helical portions 86 of the slots 85 in the guide cylinder 19. During this part of the motion of the drive cylinder, there is no relative movement between the plunger and barrel. Thus, the plunger cup 17 is not effective in driving the plunger into the barrel of the syringe.

Figure 26:
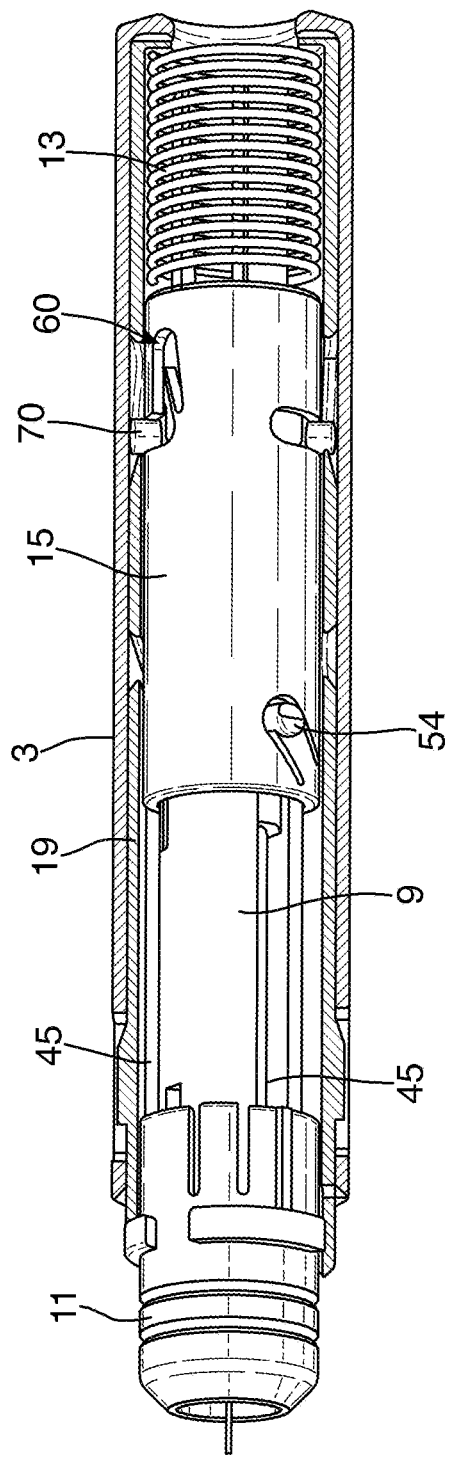

Once drive cylinder 15 and its lugs 54 have been driven forwards sufficiently to reach the linear portion 82 of the slot, the drive cylinder has rotated such that the inner lugs 52 engage the axial slots 45 on each side of the syringe housing, permitting relative axial movement of the drive cylinder 15 and syringe housing 9. The drive cylinder 15 and its lugs 52 have rotated from the position shown in FIG. 25 to the position shown in FIG. 26. At this point, the syringe housing 9 will have reached its most extended position relative to the front housing 11 as shown in FIG. 26 causing the needle to project beyond the front end of the front housing by the dispensing depth. The distance that the drive cylinder moves forward axially while rotating in order to enter the slots in the syringe housing may be used to control the distance that the needle is driven forward to reach a desired dispensing depth.

Once the lugs 52 of the drive cylinder 15 have entered the slots 45 in the syringe housing 9, the drive cylinder 15 moves axially from the position shown in FIG. 26 relative to the syringe housing 9 and hence the barrel of the syringe with the drive cylinder lugs 54 riding in the linear portions 82 of the guide cylinder slots 80. The plunger cup 17 moves forward axially with the drive cylinder being coupled thereto by movement of the lugs 70 in the circumferential portions 58 of the drive cylinder slots 60. The rotation of the plunger cup 17 is guided by virtue of the engagement of the lugs 70 in the helical portions 86 of the guide cylinder slots 85. The plunger cup 17 therefore continues to rotate as it acts to drive the plunger in the barrel under the action of the drive cylinder 15 moving linearly in the axial direction relative to the syringe housing 9 under the spring force. During this part of the cycle, the plunger cup 17 therefore acts to depress the plunger 25 and cause liquid to be dispensed through the needle.

Figure 27:
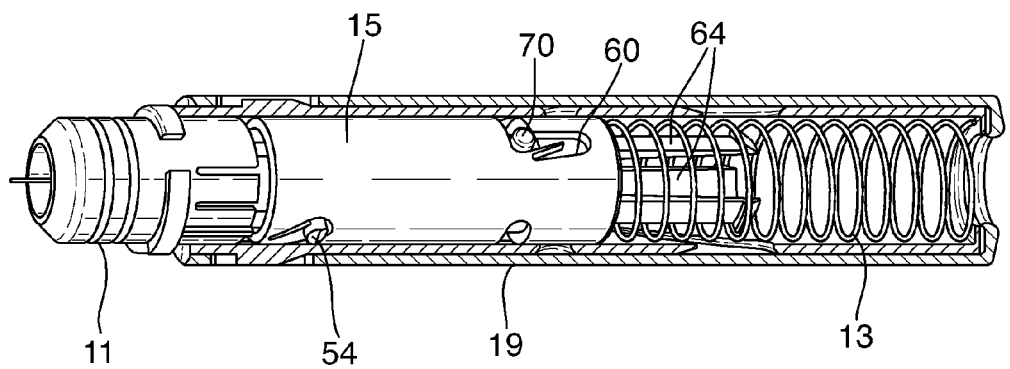
Figure 28:
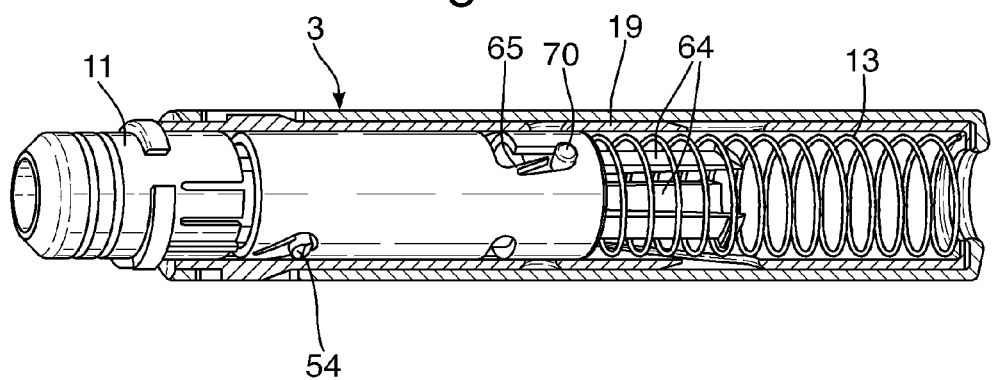

Dispensing of liquid in this manner continues until the plunger cup lugs 70 reach the end of the circumferential portions 58 of the slots 60 in the drive cylinder as shown in FIG. 27. This coincides with the point at which the drive cylinder 15 reaches the front end of the slots 45 in the syringe housing 9, and can no longer travel further axially forward in the slots 45 relative to the syringe housing 9. While the spring 13 continues to exert an axial driving force on the drive cylinder 15, the drive force is no longer effective in driving the drive cylinder 15 forward. The lugs 70 of the plunger cup 17 are free to decouple from the driving cylinder 15 by moving rearwardly in the rear legs 62 of the slots 60 in the drive cylinder 15 under the action of the return springs 50 which urge the syringe housing 9 and plunger rearwardly to retract the needle now that there is no effective forward driving force being exerted on the syringe. The linear portions 88 of the guide cylinder slots 85 enable the lugs 70 to move rearwardly in the linear portions 62 of the slots 60 in the drive cylinder 15. The decoupling of the plunger cup 17 and driving cylinder 15 means that a drive force is no longer transmitted between the drive cylinder and the plunger cup. The plunger cup 17 retracts relative to the drive cylinder with the lugs 70 moving into the rear legs 62 of the drive cylinder slots 60 from the position shown in FIG. 27, passing over resilient hooks 65 to the position shown in FIG. 28. In this way, once the lugs 70 have reached the position shown in FIG. 28, they may not move forward axially in the linear portions 62 of the slots 60, preventing the plunger cup 17 from urging the needle forward again.

It has been found that the device may be used to deliver a viscous drug over an actuation cycle which takes around 8 to 10 seconds.

Figure 29:
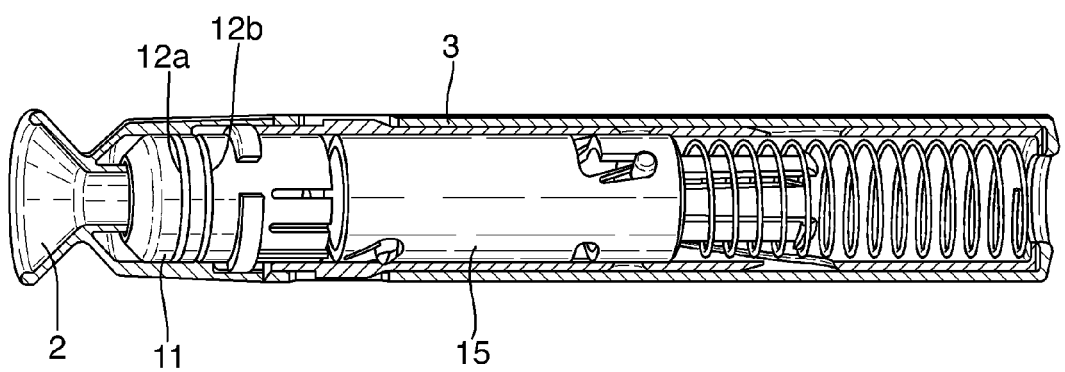
FIG. 29 is a cut away view of the device after the end cap has been replaced following completion of dispensing.

Although once the actuation cycle has finished the needle 23 is safely and permanently retracted, the user can nonetheless replace the end cap 2 for disposal of the entire device. This is shown in FIG. 29. It will be appreciated that in the post activation device shown here the position of the outer housing 3 relative to the front housing 11 has changed in comparison to that in the preactivated device (see e.g. FIG. 2) as a result of the outer housing 3 being moved forward relative to the front housing 11 in the activation step. This prevents the lug (not shown) inside the end cap 2 being fitted into the rearmost groove 12b in the front housing, but it can instead be fitted over the foremost groove 12a instead.

Before and after use of the device, the user may check the viewing window 5 in the outer housing 3 to observe whether the plunger has moved forward in the barrel to fully dispense the liquid therein.

In embodiments shown, when the plunger is depressed, the forces acting on the plunger do not pass directly through the rear flange to the main body of the barrel of the syringe, but instead bypass the rear flange by passing through the syringe housing as described above. The syringe housing acts generally to more uniformly distribute and share the forces transmitted to the barrel, reducing the stress to which it is exposed in use. This has been found to significantly decrease the likelihood of breakage or damage to the syringe barrel in use, and enables conventional unmodified syringes to be used to dispense liquids in situations where large forces need to be applied to the plunger to force the liquid out of the barrel through the needle, e.g. where greater injection depths are involved, and/or relatively more viscous liquids.

The present invention may provide a particularly effective arrangement in which minimal frictional forces are generated opposing the movement of the mechanism in depressing the plunger. For example, during use of the device, the only frictional forces generated may be those generated as a result of the movement of the lugs 70 and 54 associated with the plunger cup and drive cylinder in the respective tracks of the drive cylinder and guide cylinder. In turn, this means that lesser forces need be applied to dispense a liquid as compared to a conventional device in which significant frictional forces may be generated as a result of contact between radially extending projections and the moving parts of the device and the walls of the housing.

A further embodiment of the invention will now be described by reference to FIGS. 30-40b.

Figure 30:
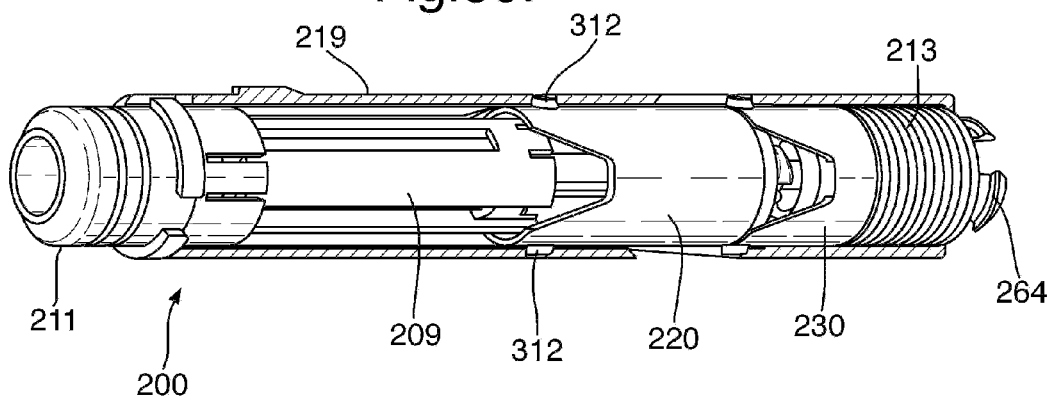
FIG. 30 is a cut away view of a device in accordance with a second embodiment of the present invention, but omitting the end cap and needle sheath for ease of reference.

The embodiment of FIG. 30 is similar in operation to the embodiment described with respect to FIGS. 1-29, other than in relation to the drive coupling arrangement which selectively transmits the driving force to the plunger, and the construction of the syringe housing. Rather than acting on the plunger via a separate plunger cup, a driven part of the drive coupling arrangement acts directly on the end of an appropriately modified plunger which forms the second part of a drive coupling arrangement between the driving means and plunger. Rather than comprising two parts that clamp around the syringe barrel, the syringe housing comprises a sleeve with an end plate that retains the syringe within the housing.

With reference to FIG. 30, the device of the second embodiment of the invention is shown. FIG. 30 omits the rear outer housing and end cap which would be provided in the same manner as with the embodiment of FIG. 1.

Figure 30A:
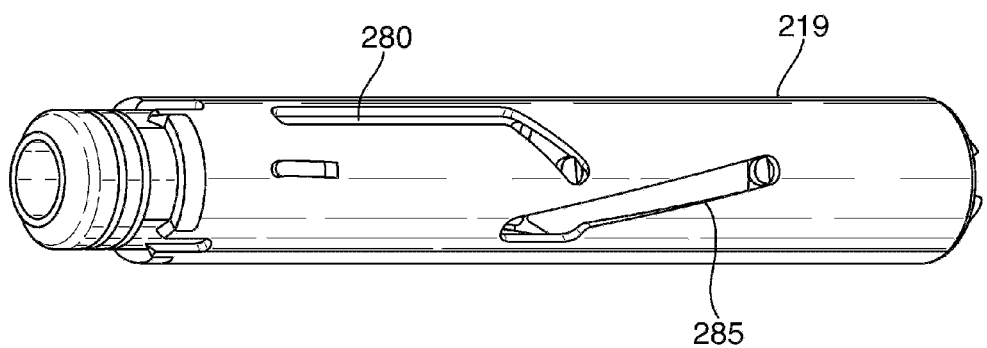
FIG. 30a is a view of the guide sleeve used in accordance with the second embodiment of the invention.

The embodiment of FIG. 30 still includes a guide cylinder 219 over which the rear outer housing will extend in the complete device. The guide cylinder 219 is shown in FIG. 30a. It may be seen that the guide cylinder 219 includes slots 285, 280 of the same configuration used in the earlier embodiment, and shown for example in FIG. 20, which cooperate with lugs 314, 312 respectively disposed on the plunger driving part 230 and syringe advancing part 220 in a similar manner to the way in which the lugs of the drive cylinder and plunger cup of the earlier embodiment interact with the guide cylinder 19. The device includes a front housing 211 connected to the guide cylinder 219.

The syringe is located in a syringe housing 209 which is of a different construction to the syringe housing of the embodiment of FIGS. 1-29. As shown in more detail in FIGS. 35 and 36, the syringe housing is formed from two parts which are assembled together to provide the housing for a syringe having a plunger of the configuration illustrated in FIG. 37.

Figure 32:
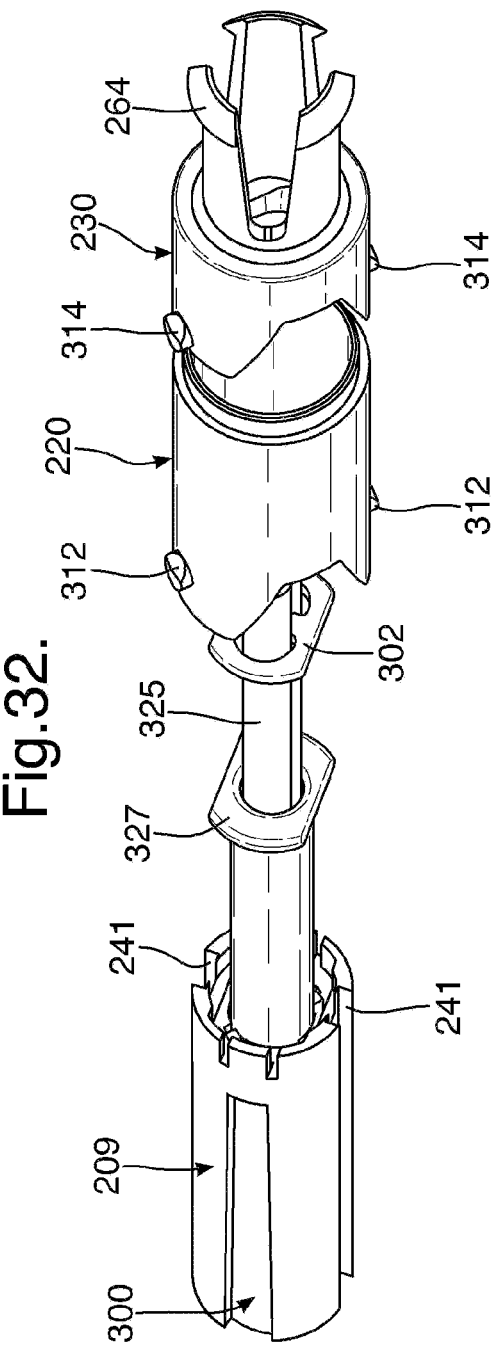
FIG. 32 is a view similar to that of FIG. 31, but taken from a different perspective relative to the device.
Figure 35:
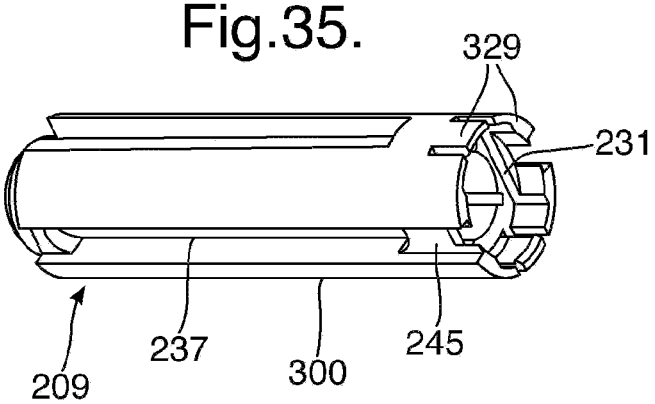
FIG. 35 illustrates the sleeve portion of the syringe housing used in the embodiment of FIG. 30, and which may also be used in accordance with the device of the first embodiment described above.
Figure 36:
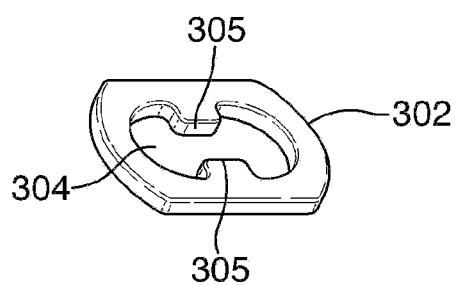
FIG. 36 illustrates the end plate used to retain the syringe in the sleeve of the syringe housing of the embodiment of FIG. 35.

The syringe housing includes a sleeve portion 300 shown in FIG. 35 and an end plate 302 shown in FIG. 36. This construction enables the syringe to be inserted in the sleeve by pushing it in from the open rear end, and then retained in place by fitting the end plate 302 over free rear end 327 of the plunger on to the rear flange 227 as shown in FIGS. 31 and 32. In order to enable the rear end plate 302 to be fitted over the rear end of the plunger 327, the rear end plate 302 defines an opening 304 of a corresponding cross sectional shape to the transverse cross sectional shape of the plunger and an appropriate dimension to enable it to be fitted over the end 327 of the plunger.

Once the plunger 325 is assembled to the sleeve and end plate forming the syringe housing, the rear flange 227 of the syringe will be sandwiched between the end plate 302 and a locating groove 231 at the rear end of the sleeve. Once the device front and rear sections are assembled together, the end plate 302 is held securely in place. In this manner, the sleeve and end plate portions of the syringe housing of this further embodiment may together provide a syringe housing which snugly fits around the syringe barrel, immobilising the syringe, and isolates the rear flange of the syringe from axial forces in the manner described above in relation to the earlier embodiment. The sleeve portion 300 of the syringe housing includes compressible material extending at least axially to enable the sleeve to snugly engage around the syringe barrel once inserted into the sleeve. The rear end of the sleeve includes slots defining resilient tabs 329 therebetween to enable the end plate 302 to be fitted through the rear end of the sleeve, but such that the end plate is retained securely in place once the front and rear sections are assembled together.

It will be appreciated that the syringe housing of this alternative construction, comprising a sleeve portion and end plate may be used in conjunction with the earlier embodiments of FIGS. 1-29, rather than using a housing comprising first and second longitudinally extending sections which are clamp around the syringe barrel, provided that an end plate with an appropriately shaped opening is used to cooperate with the shape of the end of the plunger to enable the rear plate to be fitted thereover. Both arrangements may provide immobilisation of the syringe and prevent transmission of axial forces to the barrel through the rear flange when the plunger is driven into the barrel in use. In embodiments where the syringe housing includes a sleeve and rear end plate it may be more appropriate to use a needle guard that does not include a rigid needle shield.

The embodiment of FIGS. 1-29 is particularly useful when it is desired to incorporate a standard syringe pre-pack including a plunger into the device, avoiding the need to interfere with the pre-pack. The syringe housing of the type shown in relation to the FIG. 30 embodiment could equally be used without interfering with the pre-pack, including the plunger, if used with the drive coupling arrangement disclosed in relation to the embodiment of FIGS. 1-29. However, as mentioned above, the plunger is not one of the regulated components of a syringe, and a standard syringe may be modified to add (if no plunger is provided) or otherwise substitute the plunger with an alternative plunger without needing to seek further regulatory approval. Thus, the device of the embodiment of FIG. 30 onwards, despite needing to use a customised plunger, still has the advantage that it does not interfere with the regulated part of the syringe pre-pack.

The syringe housing 209 is moveable relative to the front housing 211 in use to advance and retract the needle as in the earlier embodiment. Rather than including a pair of axially extending return springs biasing the syringe housing to a retracted position relative to the front housing, in the embodiment shown a single coil spring may be disposed between the front housing and the seat 239 defined at the front of the syringe housing sleeve 300 for biasing the syringe housing toward a retracted position. The spring will extend around the front end of the sleeve 300. It will be appreciated that such an arrangement may equally be used in accordance with the first embodiment, and equally the arrangement using a pair of axially extending springs shown in the first embodiment could alternatively be used in the second embodiment, or any other suitable arrangement may be used.

The sleeve 300 also includes a viewing window 237 as in the earlier embodiment. Axially extending slots 245 extend from the rear end of the syringe housing on each side and cooperate with lugs 310 extending from the inner surface of the syringe advancing part 230 of the drive coupling arrangement in a similar manner to the way in which lugs 54 of the drive cylinder 15 cooperate with the slots 45 of the syringe housing 9 in the earlier embodiment. A similar slot 245 is provided on the other side of the syringe housing sleeve.

Figure 37:
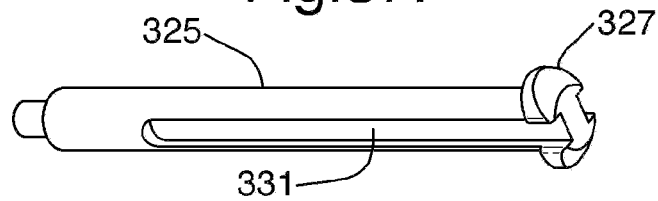
FIG. 37 illustrates the modified plunger used in the embodiment of FIG. 30.
Figure 38:
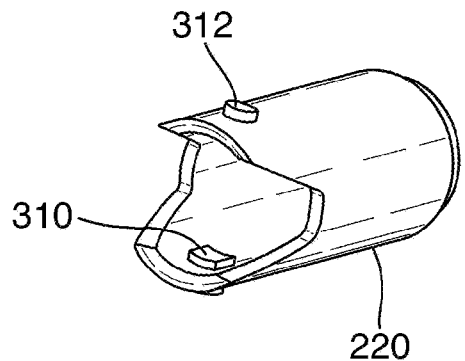
FIG. 38 illustrates a syringe advancing drive part used in the embodiment of FIG. 30.
Figure 39:
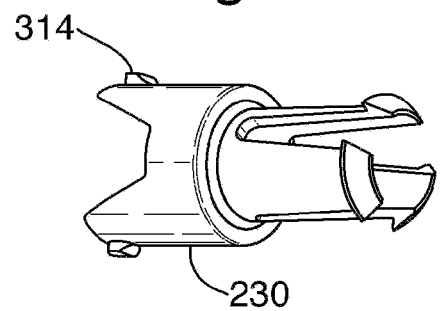
FIG. 39 illustrates the plunger driving part in the embodiment of FIG. 30.

As mentioned previously, in the further embodiment of FIGS. 30-39, the syringe used has a modified plunger to enable it to interact with the drive coupling arrangement. The plunger 325 is shown in FIG. 37. The plunger has a free end 327 which forms a part of the drive coupling arrangement as described in more detail below. The transverse cross section of the plunger is of a shape which corresponds to the cross sectional shape of the opening 304 in the end plate 302 to enable the front end of the plunger extend through the end plate 302 as described above.

It will be appreciated that the end plate 302 interacts with the plunger to constrain the plunger against rotation relative to the syringe housing. This is achieved by virtue of cooperation between the edges of the opening 304 and the shape of the plunger in transverse cross section. The end plate 302 acts as a rotational alignment plate, constraining the plunger against twisting as it moves axially into the barrel of the syringe. This is important in this further embodiment, as the drive coupling arrangement relies upon the syringe plunger maintaining a given rotational alignment in order to interact properly with the other part of the drive coupling arrangement to ensure that the driving force is transmitted or not transmitted appropriately to the plunger. In the illustrated embodiment, the inwardly projecting tabs 305 extending from the edge of opening 304 engage a slot 331 in the plunger for axially guiding the plunger as it enters the barrel.

Figure 33:
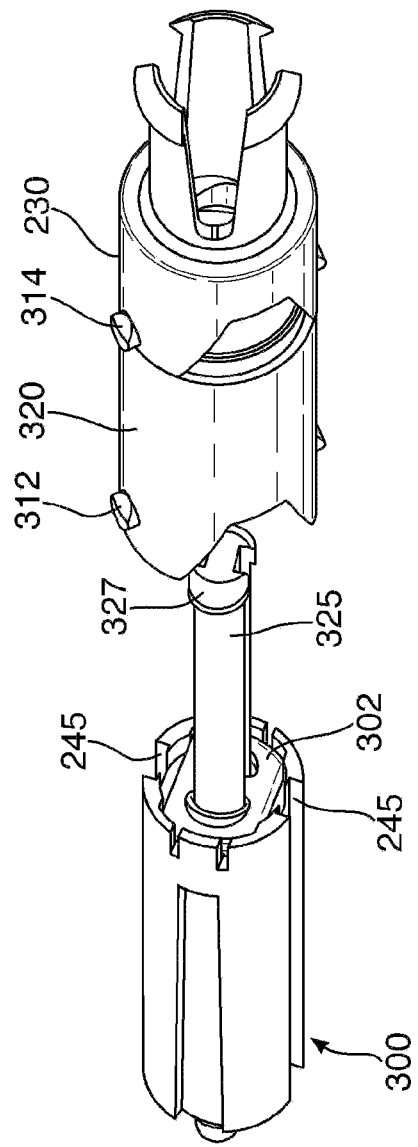
FIG. 33 is a view similar to that of FIG. 32, but showing the components of the front assembly assembled to one another.
Figure 34:
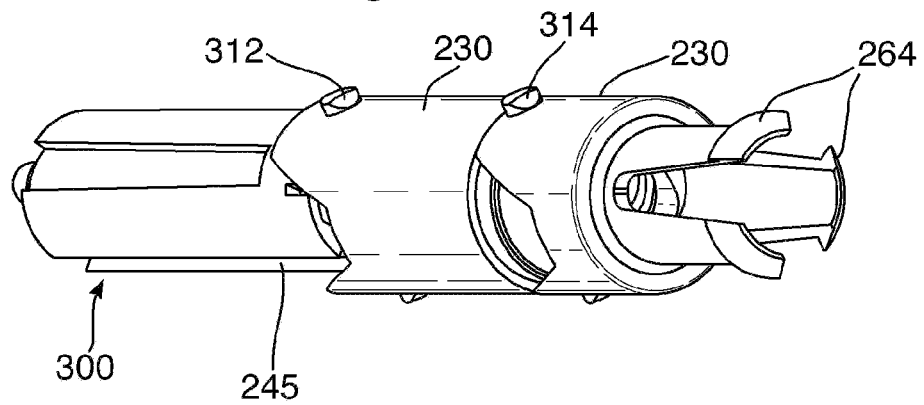
FIG. 34 is a view similar to that of FIG. 33 but with the rear assembly components assembled together.

The way in which the front part of the device is assembled may be seen by comparing FIGS. 31-33.

Once the syringe has been assembled to the syringe housing and front housing, the rear part of the device is assembled. The components of the rear part of the device will be described by reference to FIGS. 30-34, 38 and 39.

The rear part of the device comprises a driving spring 213 which provides the main driving force for propelling the syringe and driving the plunger into the barrel during the needle advancing and dispensing stages as in the earlier embodiment of FIGS. 1-29. The drive spring 213 is mounted over rear legs 264 of a plunger driving part 230 of the drive coupling arrangement. The plunger driving part 230 includes outwardly directed lugs 314 which engage a slot 285 in the guide cylinder which overlies the plunger driving part in use. The slot 285 has a profile similar to that of slot 85 in the embodiment of FIGS. 1-29, for example as illustrated in FIG. 20. Thus, when the plunger driving part 230 is driven axially under the action of the driving spring 213, it will be forced to also rotate.

Figure 40A:
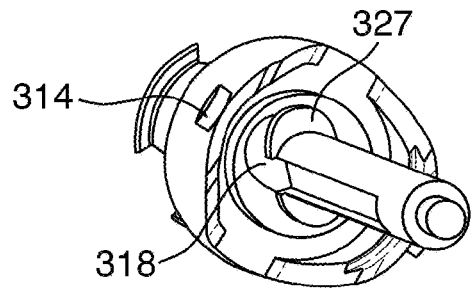
FIG. 40a illustrates the position of the plunger relative to the plunger driving part when the plunger driving part engages the plunger rear flange to exert a driving force on the plunger showing the way in which the opening in the plunger driving part interacts with the plunger rear flange.

The plunger driving part 230 includes a slot 318 having a shape which will allow the free end 327 of the plunger 325 to pass therethrough only when the slot is in a particular rotational alignment with the free end of the plunger. The slot 318 is best seen in FIGS. 31 and 31*a*. When the device is assembled, the plunger driving part 318 is located over the rear end 327 of the plunger such that the slot 318 is not rotationally aligned with the end 327 of the plunger. In this manner, the plunger driving part 318 will bear against and transmit a driving force to the end of the plunger when the main driving spring 213 is released. The initial relative rotational positions of the slot 318 and the plunger end 327 are illustrated in FIG. 40*a*.

Figure 40B:
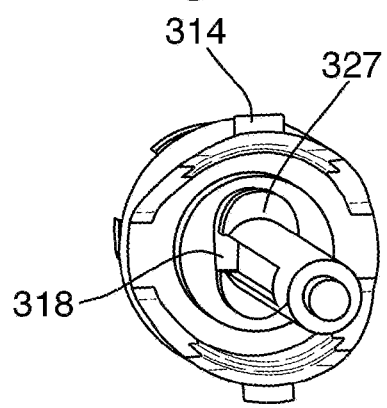
FIG. 40b illustrates the position of the plunger relative to the plunger driving part after the plunger driving part has moved out of axial engagement with the plunger rear flange, showing the way in which the opening in the plunger driving part interacts with the plunger rear flange.

In use, the plunger driving part 230 is configured to rotate as a result of the interaction between the lugs 314 with the slot of the overlying guide cylinder as it is driven by the spring 213 in use. This results in the slot 318 rotating relative to the end of the plunger 327 until it reaches a position of rotational alignment with the shaped free end 327 of the plunger, allowing the end of the plunger to pass through the slot 318. The relative positions of the plunger end 327 and the slot 318 at this stage are shown in FIG. 40*b*.

A further drive coupling part, the syringe advancing drive part 220, is located between the plunger drive part 230 and the syringe housing 209. In use, the plunger driving part 230 transmits the driving force additionally to this further part. The syringe advancing drive part 220 is used to control the transition between the needle advancing and dispensing stages. The syringe advancing drive part 220 includes outwardly directed lugs 312 which engage a slot 280 in the overlying guide cylinder. This slot has a configuration similar to slot 80 in the earlier embodiment e.g. as shown in FIG. 21.

Initially the front end of the syringe advancing drive part 220 engages the rear end of the syringe housing 209. Thus the plunger driving part 230 will initially transmit a driving force exerted by the spring 213 to the plunger and syringe advancing part 220, and the syringe advancing part 220 will act on the syringe housing to advance it with the plunger. As a result of engagement with the lugs 312 and the inclined slot 280 in the guide cylinder 219, the syringe advancing drive part 220 will be constrained to rotate during an initial part of its axial travel under the action of the drive force transmitted to it by the plunger drive part 230. This enables the syringe advancing drive part 220 to rotate to bring internal lugs 310 into alignment with axially extending slots in the syringe housing i.e. slots 245. The syringe advancing drive part will then continue to move axially relative to the syringe housing as the lugs 310 travel in slots 245.

Operation of the further embodiment of FIGS. 30-40*b* will now be described.

Once the force of the driving spring 213 is released, which may be achieved using a triggering arrangement as described in respect of the embodiment of FIGS. 1-29, the plunger driving part 230 is driven forwards axially. The slot 318 and plunger rear end 327 are initially in the relative positions shown in FIG. 40*a*. In this position the surface of the plunger driving part 230 surrounding the slot 318 bears against the end of the plunger 327, driving it forward. The plunger driving part 230 also engages against the rear end of the syringe advancing part 220 driving it forward axially. The syringe advancing part 220 bears against the rear end of the syringe housing 209 driving it, and hence the syringe including the needle forward axially to advance the needle for penetration. During this stage, as the syringe advancing part 220 is coupled to the syringe housing, there is no resultant axial force on the plunger.

As the plunger driving part 230 and the syringe advancing part 220 move forward axially, they are also constrained to rotate. Plunger driving part 230 rotates due to engagement of lugs 314 with the slot 285 in the guide cylinder 219. The syringe advancing part 220 rotates due to engagement of lugs 312 with slot 280 in guide cylinder 219. Once the syringe advancing drive part 220 has rotated to a given position relative to the front housing under the action of the drive force, at the point where the lugs 312 engage the slot 345, it is free to move axially relative to the syringe housing, such that the drive force transmitted to the plunger end via the plunger driving part 230 will be effective to drive the plunger into the barrel to dispense liquid. Thus the syringe advancing drive part 220 decouples from the syringe housing. During this dispensing stage the lugs 312 ride in slot 280 of the guide cylinder 219.

Dispensing continues until the plunger driving part 230 has rotated to the position shown in FIG. 40*b* relative to the rear end of the plunger 327. In this position the slot 318 is rotationally aligned with the end of the plunger 327. The plunger driving part 230 may no longer transmit the driving force to the plunger, and the plunger is free to retract relative to the plunger driving part 230. The syringe housing 209, and hence the syringe and plunger then retract under the action of the return spring located between the front housing and the syringe housing which biases the syringe housing toward a retracted position. In this way, the needle retraction stage is provided. During retraction the plunger end retracts through the slot 318 in the plunger drive part 230. The plunger driving part 230 cannot then come back into engagement with the end of the plunger, preventing inadvertent further actuation of the device.

The initial rotational position of the slot 318 of the plunger driving part relative to the free end of the plunger 327 may be chosen appropriately to ensure that a position of alignment between the plunger end and slot is achieved at a desired point corresponding to the end of the dispensing stage, and the start of the needle retraction stage. The initial position may depend upon the length of travel of the plunger driving part 230 in the axial direction, the inclination of the guide slot etc. It will be appreciated that any suitable angle of rotation between the plunger driving part 230 and the plunger end 327 may be used, and the illustrated arrangement is only exemplary.

It has been found that embodiments of the present invention are particularly effective when used to dispense more viscous liquids, and may be used to dispense more viscous drugs than could be achieved using prior art devices without unacceptable risk of breakage of the device. This is particularly effective, as viscous drugs are increasingly used to provide sustained release formations. Relatively large forces are needed to push a viscous drug out of the syringe through the needle, and the risk of breakage of the syringe is accordingly higher. It is thought that the device may be particularly beneficial in the context of neurobiological drugs which are becoming available, and which are relatively viscous, causing difficulties when it is attempted to dispense them using conventional devices.

The present invention also provides the ability to more precisely control the depth of delivery of a drug, by providing greater control over the start and finish of the needle advancement and dispensing parts of the actuation cycle, as well as the distance by which the needle advances in the insertion part of the cycle. The device may readily be adapted to provide a range of different needle depth selections with minimal or no modification, allowing the use of the device to deliver subcutaneous, intradermal, subdermal or intramuscular drugs. For example, this may be achieved by suitable adaption of the lengths of the slots guiding movement of the drive cylinder and plunger cup, or plunger and syringe driving parts during the different parts of the cycle.

The device is configured such that it may be used without modification to the standard regulated syringe prepack which has already received regulatory approval.

The present invention may provide an automatic injection device which has a range of different safety features to guard against needle stick injuries, and which may comply with increasing regulation in this area. For example, the device may include multiple features to safeguard against premature activation, and may also enable the needle to start from a more retracted position due to the greater ability to reliably advance the needle to a desired insertion depth in use.

It is believed that the device is particularly simple to use, and may be used by people with manual dexterity difficulties. The ability to use for a user to self administer drugs is advantageous, enabling the user to self-inject at home, avoiding the need for professional staff to be involved in the treatment of patients, leading to corresponding cost savings and benefits in increasing the penetration of drug delivery.

The present invention in its preferred embodiments reduces the number of moving parts which are required to complete the auto injection cycle, including the needle insertion, drug dispensing and needle withdrawal stages. It has been found that the device may be produced using injection moulding techniques, with a process involving few splits. For example, it has been found that a device in accordance with the first embodiment may be made with as few as two splits.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is therefore understood that the invention is not limited to the specific embodiments disclosed herein, and that many modifications and other embodiments of the invention are intended to be included within the scope of the invention. Moreover, although specific terms are employed herein, they are used only in a generic and descriptive sense, and not for the purposes of limiting the described invention.

Various publications are referenced in this document. These publications in their entireties are hereby incorporated by reference into this application in order to more fully describe the state of the art to which the disclosed system and method pertains. The references disclosed are also individually and specifically incorporated by reference herein for the material contained in them that is discussed in the sentence in which the reference is relied upon.

The invention claimed is:

1. An automatic injection device, comprising:
a syringe having a needle, a barrel and a plunger; and
driving means for driving the plunger into the barrel;
wherein the injection device is configured to perform an automatic actuation cycle in use comprising the stages of advancing the needle of the syringe for insertion, driving the plunger into the barrel for dispensing a liquid contained in the barrel, and retracting the needle;
wherein the device is configured such that during operation of the device, a driving force is transmitted from the driving means to the plunger during the dispensing stage, and such that a driving force is not transmitted to the plunger during the refraction stage to allow retraction of the needle;
wherein the automatic injection device comprises a drive coupling arrangement between said driving means and said syringe;
wherein said drive coupling arrangement comprises a drive coupling part selectively transmitting or not transmitting force from the driving means to the plunger depending upon the rotational position of the coupling part;
wherein the device is configured such that, depending upon a configuration of the drive coupling arrangement, the syringe is driven forward during the needle advancement stage and the plunger is driven into the barrel during the dispensing stage for dispensing a liquid contained in the barrel, and
wherein a transition between said needle advancement and dispensing stages is controlled by the rotation of a part of said drive coupling arrangement.

2. The automatic injection device of claim 1, wherein said drive coupling arrangement is configured to transmit a driving force to the syringe barrel during said needle advancement stage, and to transmit a driving force to the plunger and not the syringe barrel during said dispensing stage for driving the plunger into the barrel.

3. The automatic injection device of claim 1, wherein said drive coupling arrangement comprises at least first and second parts which are configurable such that a driving force can be selectively transmitted or not transmitted between them in use depending upon the relative rotational positions of the parts, and wherein the first and second parts are configured such that during operation of the device, a driving force is transmitted between the first and second parts during the dispensing stage for applying a driving force to the plunger, and such that a driving force is not transmitted between the first and second parts during the retraction stage to allow retraction of the needle.

4. The automatic injection device of claim 3, wherein the device is configured such that a driving force transmitted from the first part to the second part is selectively effective to drive the plunger into the barrel of the syringe depending upon the rotational position of the first part.

5. The automatic injection device of claim 3, wherein the second part is provided as a separate part from said plunger, and is movable relative to said plunger.

6. The automatic injection device of claim 3, wherein the second part comprises a member adapted to engage a syringe plunger handle.

7. The automatic injection device of claim 3, wherein the second part is configured to rotate relative to the plunger in use, wherein the second part comprises a bearing surface for contacting the end of the plunger.

8. The automatic injection device of claim 3, wherein the second part is configured to rotate relative to the first part under the action of the driving force transmitted thereto by the first part in use, the second part being rotatable into a given rotational position relative to the first part in which the driving force is no longer transmitted between the first and second parts in use.

9. The automatic injection device of claim 3, wherein the first part is initially not movable axially relative to the barrel of the syringe, and is rotatable under the action of the driving force to a position in which it is movable axially relative to the barrel of the syringe to drive the plunger into the barrel.

10. The automatic injection device of claim 3, wherein the second part is configured to be rotatable under the action of the driving force transmitted thereto, and the first part is configured to rotate in an opposite sense to the second part under the action of the driving force.

11. The automatic injection device of claim 3, further comprising means for disabling the device after operation, wherein said disabling means comprises means for retaining the second part in a position relative to the first part in which the first part may not transmit a driving force thereto.

12. The automatic injection device of claim 3, wherein the first part is configured to rotate relative to the second part under the action of the driving force to bring at least a portion of the first part into a given rotational alignment with at least a portion of the second part such that a driving force is no longer transmitted to the second part.

13. The automatic injection device of claim 12, wherein the first part rotates into a rotational alignment with the second part such that a surface of the first part no longer bears against the surface of the second part to transmit a driving force thereto.

14. The automatic injection device of claim 12, wherein the portion of the first part rotates into a rotational alignment with the portion of the second part to enable the second part to retract through the portion of the first part when the driving force is no longer transmitted to the second part.

15. The automatic injection device of claim 12, wherein the first part comprises an opening which rotates into alignment with the at least a portion of the second part.

16. The automatic injection device of claim 15, wherein said opening and said second part are configured such that said second part may pass through said opening only when the opening has rotated into rotational alignment with the portion of the second part.

17. The automatic injection device of claim 12, wherein the drive coupling arrangement comprises a third part, wherein the first part is configured to transmit a driving force to the third part, wherein the third part is configured to move under the action of the driving force between a first position in which the driving force is transmitted to the barrel of the syringe, and a second position in which the driving force is not transmitted to the barrel of the syringe.

18. The automatic injection device of claim 12, comprising means for constraining the plunger and the second part against rotation relative to the syringe barrel as the plunger is driven into the syringe barrel in use.

19. The automatic injection device of claim 12, wherein said second part is provided as part of said plunger, preferably by a rear flange of the plunger.

20. The automatic injection device of claim 3, wherein the device is configured such that once the driving force is no longer transmitted from the first part to the second part in use, the driving force continues to be applied to the first part but is no longer effective in driving the first part axially.

21. The automatic injection device of claim 3, wherein the device is configured such that once the driving force ceases to be transmitted from the first part to the second part in use, the barrel and plunger are free to move rearwardly thereby retracting the needle.

22. The automatic injection device of claim 3, wherein the second part is configured to retract relative to the first part when the first part ceases to transmit a driving force thereto in use.

23. The automatic injection device of claim 3, further comprising guide means for influencing the movement of the first part and/or the second part under the action of the driving force.

24. The automatic injection device of claim 3, wherein the movement of the first part and/or the second part under the action of the driving force is guided by the travel of a pin in a slot.

25. The automatic injection device of claim 3, wherein the first and second parts are configured such that in use, the first part is acted upon by the driving means, and the second part acts on the plunger.

26. The automatic injection device of claim 1, wherein the syringe is received in a syringe housing, wherein said syringe housing is configured such that the barrel and the rear flange are immobilised in the syringe housing such that they can be moved within the device by a force applied to the syringe housing.

27. The automatic injection device of claim 26, wherein the syringe housing clamps on to the syringe barrel.

28. The automatic injection device of claim 26, wherein the syringe housing is configured such that when the plunger is driven into the barrel in use, no axial force is transmitted to the barrel of the syringe through the rear flange.

29. The automatic injection device of claim 1, wherein the front end of the syringe housing is coupled to a front housing for protecting the needle, the front housing being intended to be located against the skin of a user in use, wherein the syringe housing is axially movable relative to the front housing between a first retracted position and a second extended position corresponding to concealed and exposed positions of the needle.

30. The automatic injection device of claim 1, wherein the device comprises activation means adapted to be operated by a user to trigger automatic injection delivery, wherein the device comprises an outer housing, the outer housing configured to be axially movable relative to a front housing of the device to enable activation of the device by urging the outer housing toward the front housing of the device.

31. The automatic injection device of claim 1 further comprising an end cap which covers the front needle end of the device, wherein the end cap is configured such that it may be replaced after actuation of the device, the device comprising first and second means respectively cooperating with the end cap to enable the end cap to be clipped onto the end of the device both before and after actuation of the device, the first and second means being located in different axial positions.

32. A method of operating an automatic injection device in accordance with claim 1, comprising the steps of placing the device against the skin of a user and activating the device.

33. An automatic injection device in accordance with claim 1, further comprising a liquid to be dispensed in the syringe barrel.

34. A kit of parts for the automatic injection device in accordance with claim 1.

35. The automatic injection device of claim 1, wherein the driving force transmitted to the plunger is not effective to drive the plunger into the barrel when said drive coupling part is in a first rotational position, and wherein the driving force transmitted to the plunger is effective to drive the plunger into the barrel when the drive coupling part has rotated into a second rotational position.

36. The automatic injection device of claim 1, wherein the device is configured such that there is no resultant axial force on the plunger during the needle advancement stage.

* * * * *